US007910586B2

(12) United States Patent
Netzer et al.

(10) Patent No.: US 7,910,586 B2
(45) Date of Patent: Mar. 22, 2011

(54) COMPOSITIONS AND METHODS FOR PREVENTION AND TREATMENT OF AMYLOID-β PEPTIDE-RELATED DISORDERS

(75) Inventors: William Netzer, New York, NY (US); Paul Greengard, New York, NY (US); Huaxi Xu, New York, NY (US)

(73) Assignee: The Rockefeller University, New York, NY (US)

( * ) Notice: Subject to any disclaimer, the term of this patent is extended or adjusted under 35 U.S.C. 154(b) by 1487 days.

(21) Appl. No.: 10/337,261

(22) Filed: Jan. 6, 2003

(65) Prior Publication Data

US 2004/0028673 A1      Feb. 12, 2004

Related U.S. Application Data

(60) Provisional application No. 60/345,009, filed on Jan. 4, 2002.

(51) Int. Cl.
| | |
|---|---|
| *A01N 43/58* | (2006.01) |
| *A01N 43/54* | (2006.01) |
| *A01N 43/40* | (2006.01) |
| *A01N 43/42* | (2006.01) |
| *A61K 31/50* | (2006.01) |
| *A61K 31/435* | (2006.01) |
| *A61K 31/44* | (2006.01) |
| *C07D 239/42* | (2006.01) |
| *C07D 401/04* | (2006.01) |
| *C07D 471/04* | (2006.01) |
| *C07D 471/22* | (2006.01) |
| *C07D 487/04* | (2006.01) |

(52) U.S. Cl. ........ 514/247; 514/256; 514/257; 514/277; 514/279

(58) Field of Classification Search ............... 514/49, 514/247, 256, 257, 277, 279; 536/28.4; 538/28.4
See application file for complete search history.

(56) References Cited

U.S. PATENT DOCUMENTS

| | | | | |
|---|---|---|---|---|
| 5,272,055 | A * | 12/1993 | Haley | ............... 435/6 |
| 5,385,915 | A | 1/1995 | Buxbaum et al. | |
| 5,521,184 | A | 5/1996 | Zimmermann | |
| 5,543,520 | A * | 8/1996 | Zimmermann | ............... 544/331 |
| 5,733,914 | A | 3/1998 | Blankley et al. | |
| 6,107,301 | A | 8/2000 | Aldrich et al. | |
| 6,147,073 | A | 11/2000 | Battistini et al. | |
| 6,451,838 | B1 | 9/2002 | Moon et al. | |
| 2002/0025540 | A1 | 2/2002 | Roberts et al. | |
| 2002/0128319 | A1 | 9/2002 | Koo et al. | |
| 2002/0147197 | A1* | 10/2002 | Newman et al. | ......... 514/235.8 |

FOREIGN PATENT DOCUMENTS

| | | |
|---|---|---|
| EP | 0949242 | 10/1999 |
| WO | WO 96/34867 | 11/1996 |
| WO | WO 99/01439 | 1/1999 |
| WO | WO 99/19305 | 4/1999 |
| WO | WO 01/64200 | 9/2001 |
| WO | WO 01/77086 | 10/2001 |
| WO | WO 01/78721 | 10/2001 |
| WO | WO 01/85924 | 11/2001 |
| WO | PCT/US03/00249 | 1/2003 |

OTHER PUBLICATIONS

Borchelt, et al., "Familial Alzheimer's Disease-Linked Presenilin 1 Variants Elevate Aβ1-42/1-40 Ratio in Vitro and in Vivo," *Neuron.* (1996) 17: 1005-1013.
DeMattos, et al, "Peripheral anti-Aβ Antibody Alters CNS and Plasma Aβ Clearance and Decreases Brain Aβ Burden in a Mosue Model of Alzheimer's Disease," *PNAS* (2001) 98(15): 8850-8855.
Dou, et al., "Chaperones Increase Association of the Tau Protein with Microtubules," *Proc. Natl Acad Sci* USA (2003) 100(2): 721-726-12449.
Durkin, et al., "Rank-Order of Potencies for Inhibition of the Secretion of Aβ40 and Aβ42 Suggests That Both Are Generated by a Single γ-Secretase," *The Journal of Biochemistry* (1999) 274(29): 20499-20504.
De Strooper, et al., "A Presenilin-l-Depenedent γ-Secretase-Like Protease Mediates Release of Notch Intracelllular Domain," *Nature* (1999) 398: 518-522.
Esler, et al., "Transition-State Analogue Inhibitors of γ-Secretase Bind Directly to Presenilin-1," *Nature Cell Biology* (2000) 2: 428-434.
Gasparini, et al., "Stimulation of β-Amyloid Precursor Protein Trafficking by Insulin Reduces Intraneuronal β-Amyloid and Requires Mitogen-Activated Protein Kinase Signaling," *The Journal of Neuroscience* (2001) 21(8): 2561-2570.
Moasser, et al., "Inhibition of Src Kinases by a Selective Tyrosine Kinase Inhibitor Causes Mitotic Arrest," *Cancer Research* (1999) 59: 6145-6152.
Nagar, et al., "Crystal Structures of the Kinase Domain of c-Abl in Complex with the Small Molecule Inhibitors PD173955 and Imatinib (STI-571)," *Cancer Research* (2002) 62: 4236-4243.
Netzer, et al., "Gleevec Inhibits Beta-Amyloid Production but not Notch Cleavage.," *Proc. Natl Acad Sci USA* (2003) 100(21): 12444-12449.
Petanceska, et al., "The Phosphatidylinositol 3-Kinase Inhibitor Wortmannin Alters the Metabolism of the Alzheimer's Amyloid Precursor Protein," *Journal of Neurochemistry* (1999) 73(6): 2316-2320.
Schindler, et al., "Structural Mechanism for STI-571 Inhibition of Abelson Tyrosine Kinase," *Journal of Neurochemistry* (2000) 289: 1938-1942.

(Continued)

*Primary Examiner* — Yong S Chong
(74) *Attorney, Agent, or Firm* — Hoxie & Associates LLC

(57) ABSTRACT

The present invention provides methods and compositions for modulating levels of amyloid-β peptide (Aβ) exhibited by cells or tissues. The invention also provides pharmaceutical compositions and methods of screening for compounds that modulate Aβ levels. The invention also provides modulation of Aβ levels via selective modulation (e.g., inhibition) of ATP-dependent γ-secretase activity. The invention also provides methods of preventing, treating or ameliorating the symptoms of a disorder, including but not limited to an Aβ-related disorder, by administering a modulator of γ-secretase, including, but not limited to, a selective inhibitor of ATP-dependent γ-secretase activity or an agent that decreases the formation of active (or optimally active) γ-secretase. The invention also provides the use of inhibitors of ATP-dependent γ-secretase activity to prevent, treat or ameliorate the symptoms of Alzheimer's disease.

12 Claims, 20 Drawing Sheets

OTHER PUBLICATIONS

Selkoe, Dennis J., "Deciphering the Genesis and Fate of Amyloid β-Protein Yields Novel Therapies fro Alzheimer Disease," *Journal of Neurochemistry* (1999) 73(6): 2316-2320.

Vandermeeren, et al., "The Functional γ-Secretase Inhibitor Prevents Production of Amyloid β 1-34 in Human and Murine Cell Lines," *Neuroscience Letters*.(2001) 315: 145-148.

Wolfe, Michael S., "Secretase Targets for Alzheimer's Disease: Identification and Therapeutic Potential," *Journal of Medicinal Chemistry* (2001) 44(13): 2039-2060.

Xu, et al., "Generation of Alzheimer β-Amyloid Protein in the Trans-Golgi Network in the Apparent Absence of Vesicle Formation," *Proc. Natl. Acad. Sci* (1997) 94: 3748-3752.

Zhang, et al., "Biochemical Characterization of the γ-Secretase Activity That Produces β-Amyloid Peptides," *Biochemistry* (2001) 40: 5049-5055.

Esler, W.P., et al. *A Portrait of Alzheimer Secretases—New Features and Familiar Faces*, Science, 2001, pp. 1449-1454, vol. 293.

Selkoe, D.J. *Alzheimer's Disease: Genotypes, Phenotype, and Treatments*, Science, 1997, p. 630, vol. 275.

Vassar, R., et al. β-*Secretase Cleavage of Alzheimer's Amyloid Precursor Protein by the Transmembrane Aspartic Protease BACE*, Science, 1999, pp. 735-741, vol. 286.

Schenk, D., et al. *Immunization with Amyloid-β Attenuates Alzheimer-Disease-Like Pathology in the PDAPP Mouse*, Nature, 1999, pp. 173-177, vol. 400.

Netzer, W.J., et al. *Gleevec Inhibits β-Amyloid Production But Not Notch Cleavage*, PNAS, 2003, pp. 12444-12449, vol. 100.

Gilman, S., et al. *Clinical effects of Aβ Immunization (AN1792) in Patients with AD in an Interrupted Trial*, Neurology, 2005, pp. 1553-1562, vol. 64.

Dominguez et al., Secretase as therapeutic targets for the treatment of Alzheimer's disease, Amyloid: J. Protein Folding Disord. 8, 124-142(2001).

Dumont et al., Synthesis and Study of the Anti-Leukaemic Activity of N,N'-Substituted Amidines and Bis-Amidines, J. Pharm. Belg., 40:6, 373-386 (1985).

Goodwin, et al., P3-215: Inhibition of gamma-secretase activity induces cell cycle defects and chromosome missegregation, Alzheimer's & Dementia, vol. 4, No. 1, p. T614 Jul. 1, 2008.

Kraker et al., Biochemical and Cellular Effects of c-Src Kinase-Selective Pyrido[2,3-d]pyrimidine Tyrosine Kinase Inhibitors, Biochemical Pharmacology, vol. 60, pp. 885-898 (2000).

Williamson et al., Rapid Tyrosine Phosphorylation of Neuronal Proteins Including Tau and Focal Adhesion Kinase in Response to Amyloid-B Peptide Exposure: Involvement of Src Family Protein Kinases, J. of Neuroscience, 22(1):10-20 (Jan. 1, 2002).

Wolfe, M., γ-Secretase Inhibitors as Molecular Probes of Presenilin Function, J. Mol. Neuroscience, vol. 17, pp. 199-204 (2001).

* cited by examiner

COMPOSITIONS AND METHODS FOR PREVENTION AND TREATMENT OF AMYLOID-β PEPTIDE-RELATED DISORDERS

RELATED APPLICATIONS

This application claims benefit, under 35 U.S.C. §119(e), of U.S. provisional application No. 60/345,009, filed on Jan. 4, 2002, which is incorporated herein by reference in its entirety.

This invention was made with Government support under grant number 5P01AG009464-07 awarded by the National Institutes of Health. The United States Government may have certain rights in the invention.

1. TECHNICAL FIELD

The present invention relates to methods and compositions for modulating levels of amyloid-β peptide (Aβ) exhibited by cells or tissues. The invention also relates to pharmaceutical compositions and methods of screening for compounds that modulate Aβ levels. The invention also relates to modulation of Aβ levels via selective modulation (e.g., inhibition) of ATP-dependent γ-secretase activity. The invention also relates to methods of preventing, treating or ameliorating the symptoms of a disorder, including but not limited to an Aβ-related disorder, by administering a modulator of γ-secretase, including, but not limited to, a selective inhibitor of ATP-dependent γ-secretase activity or an agent that decreases the formation of active (or optimally active) γ-secretase. The invention also relates to the use of inhibitors of ATP-dependent γ-secretase activity to prevent, treat or ameliorate the symptoms of Alzheimer's disease.

2. BACKGROUND OF THE INVENTION

Amyloid-β (Aβ) peptides are metabolites of the Alzheimer's disease-associated precursor protein, β-amyloid precursor protein (APP), and are believed to be the major pathological determinants of Alzheimer's disease (AD). These peptides consist mainly of 40 to 42 amino acids, Aβ1-40 ("Aβ40") and Aβ1-42 ("Aβ42"), respectively. Aβ40 and Aβ42 are generated by two enzymatic cleavages occurring close to the C-terminus of APP. The enzymes responsible for the cleavage, β-secretase and γ-secretase, generate the – and C-termini of Aβ, respectively. The amino terminus of Aβ is formed by β-secretase cleavage between methionine residue 596 and aspartate residue 597 of APP (APP 695 isoform numbering) (see, e.g., U.S. Pat. No. 6,440,698; and U.S. Pat. No. 5,744,346).

γ-secretase activity cleaves at varying positions 38-, 40- or 43-residues C-terminal of this β-secretase cleavage to release Aβ peptides (for a review of γ-secretase and γ-secretase activity, see, e.g., U.S. Patent Application 20020025540). The complete molecular identity of γ-secretase enzyme is still unknown. Presenilin 1, or the closely related presenilin 2, is needed for γ-secretase activity. γ-secretase activity is reduced 80% in cultured cells derived from embryos genetically deleted for presenilin 1. All γ-secretase activity is lost in cells lacking both presenilin 1 and presenilin 2. Peptidomimetic inhibitors of γ-secretase activity can be crosslinked to presenilins 1 and 2, suggesting that these proteins are catalytic subunits for the cleavage. However, γ-secretase activity isolated from cells chromatographs as a large complex>1 M daltons. Recent genetic studies have identified three more proteins required for γ-secretase activity; nicastrin, aph-1 and pen-1. (Francis et al., 2002, Developmental Cell 3(1): 85-97; Steiner et al., 2002, J. Biol. Chemistry: 277(42): 39062-39065; and Li et al., 2002, J. Neurochem. 82(6): 1540-1548). Accumulation of presenilin into high molecular weight complexes is altered in cells lacking these proteins.

A third enzyme, α-secretase, cleaves the precursor protein between the β- and γ-cleavage sites, thus precluding Aβ production and releasing an approximately 3 kDa peptide known as P3, which is non-pathological. Both β- and α-secretase cleavage also result in soluble, secreted—terminal fragments of APP, known as sAPPβ and sAPPα, respectively. The sAPPα fragment has been suggested to be neuroprotective.

In normal individuals, the Aβ peptide is found in two predominant forms, the majority Aβ-40 (also known as Aβ1-40) form and the minority Aβ42 (also known as Aβ1-42) form, each having a distinct COOH-terminus. The major histological lesions of AD are neuritic plaques and neurofibrillary tangles occurring in affected brain regions. Neuritic plaques consist of Aβ peptides, primarily Aβ40 and Aβ42. Although healthy neurons produce at least ten times more Aβ40 compared to Aβ42, plaques contain a larger proportion of the less soluble Aβ42. Patients with the most common form of familial Alzheimer's disease show an increase in the amount of the Aβ42 form. The Aβ40 form is not associated with early deposits of amyloid plaques. In contrast, the Aβ42 form accumulates early and predominantly in the parenchymal plaques and there is strong evidence that Aβ42 plays a major role in amyloid plaque deposits in familial Alzheimer's disease patients (Roher et al., 1993, Proc. Natl. Acad. Sci. USA 90:10836; Iwatasubo, T., et al., 1994 Neuron 13:45; Yamaguchi et al, 1995, Amyloid Int. J. Clin. Invest. 2:7-16; and Mann et al., 1996 Am. J. Pathol. 148:1257).

Neurofibrillary tangles consist of aggregated tau protein and their role in AD pathology is less clear. AD symptoms are most closely correlated with total brain Aβ rather than plaques. About 10% of AD cases result from autosomal dominant inheritance of mutations in either the APP or the presenilin 1 and presenilin 2 genes. In both cases, increased production of total Aβ or Aβ42 versus Aβ40 results. There is strong evidence that Aβ peptides are critical in the pathogenesis of Alzheimer's disease. Therefore, compositions which modulate the activity and/or levels of these peptides are desired.

For example, U.S. Patent Application 20020128319 A1 states that certain non-steroidal anti-inflammatory drugs (NSAIDS) lower production and/or levels of Aβ42 in cell cultures expressing Aβ40 and Aβ42 derived from the cleavage of APP. Since there is good evidence that high Aβ42 levels are a major risk factor for AD, such drugs may be useful in preventing, delaying or reversing the progression of AD. The drawback of the use of such drugs, however, is that large doses of NSAIDS are required for significant lowering of Aβ42, and significant gastrointestinal side effects, including bleeding ulcers, are associated with prolonged use of NSAIDS at high doses (Langman et al., 1994, Lancet 343: 1075-1078). In addition, there remains an unknown risk for Alzheimer's disease due to amyloid formation from Aβ40 and other forms unaffected by Aβ42 lowering agents.

There is, therefore, a need in the art to develop treatments for diseases or disorders related to the regulation of Aβ production. Furthermore, there is a need to develop methods of screening that can be used to identify compounds to treat such diseases or disorders.

Citation or identification of any reference in Section 2, or in any other section of this application, shall not be considered an admission that such reference is available as prior art to the present invention.

3. SUMMARY OF THE INVENTION

The present invention is based, in part, on Applicants' surprising discoveries that γ-secretase activity in cells requires adenosine triphosphate (ATP) in order to optimally produce amyloid-β peptide ("Aβ") from APP and that selective competitors of ATP reduce Aβ levels, in particular, levels of secreted Aβ.

The present invention, therefore, relates, generally, to methods and compositions for preventing or treating an Aβ-related disorder such as Alzheimer's disease via administration of compounds that modulate, e.g., inhibit, ATP-dependent enzymatic activity such as γ-secretase activity.

The invention provides a method for modulating amyloid-β peptide (Aβ) levels exhibited by a cell or tissue comprising contacting said cell or tissue with an amount of a compound sufficient to modulate said Aβ levels, wherein said compound modulates an ATP-dependent enzymatic activity.

In one embodiment, the Aβ levels are lowered. In another embodiment, the Aβ levels are raised. In another embodiment, the Aβ is Aβ40. In another embodiment, the Aβ is Aβ42.

In another embodiment, the modulating results in an increase in the ratio of Aβ40 to Aβ42. In another embodiment, the modulating results in an increase in C99.

In another embodiment, the compound binds an enzyme that exhibits an ATP-dependent enzymatic activity. In another embodiment, the compound binds a molecule that regulates the ATP-enzymatic activity.

In another embodiment, the compounds binds a molecule present in a complex with an enzyme that exhibits the ATP-dependent enzymatic activity, e.g., γ-secretase activity.

In another embodiment, the molecule is a molecule that is allosterically regulated by ATP.

In another embodiment, the compound is an ATP modulator. In another embodiment, the the ATP modulator is a selective modulator.

In another embodiment, the ATP modulator competes with ATP for binding to an ATP-binding site. In another embodiment, the ATP-binding site is present on an enzyme that exhibits an ATP-dependent enzymatic activity. In another embodiment, the ATP-binding site is present on a molecule that regulates the ATP-dependent enzymatic activity.

In another embodiment, the compound does not affect total cellular levels of β-amyloid precursor product (APP). In another embodiment, the compound does not decrease levels of secreted APP (sAPP). In another embodiment, the compound increases levels of sAPPα. In another embodiment, levels of secreted Aβ are modulated. In another embodiment, the compound does not inhibit Notch-1 cleavage. In another embodiment, the compound does not inhibit tau phosphorylation.

In another embodiment, the compound crosses the blood-brain barrier.

In another embodiment, the enzymatic activity is a γ-secretase activity. In another embodiment, the compound inhibits γ-secretase activity. In another embodiment, the compound is an ATP modulator. In another embodiment, the ATP modulator is a selective modulator.

In another embodiment, the compound binds a γ-secretase enzyme exhibiting an ATP-dependent enzymatic activity. In another embodiment, the ATP modulator competes with ATP for binding to an ATP binding site.

In another embodiment, the compound is STI-571 or a blood-brain barrier permeable variant thereof, or a pharmaceutically acceptable salt thereof. In another embodiment, the compound is a mesylate salt of STI-571. In another embodiment, the compound is WGB-BC-15 or a blood-brain barrier permeable variant thereof, or a pharmaceutically acceptable salt thereof. In another embodiment, the compound is Compound 1 or a blood-brain barrier permeable variant thereof, or a pharmaceutically acceptable salt thereof. In another embodiment, the compound is Compound 2 or a blood-brain barrier permeable variant thereof, or a pharmaceutically acceptable salt thereof. In another embodiment, the compound is Compound 3 or a blood-brain barrier permeable variant thereof, or a pharmaceutically acceptable salt thereof. In another embodiment, the compound is Compound 4 or a blood-brain barrier permeable variant thereof, or a pharmaceutically acceptable salt thereof. In another embodiment, the compound is Compound 5 or a blood-brain barrier permeable variant thereof, or a pharmaceutically acceptable salt thereof.

In another embodiment, the enzymatic activity is a kinase activity. In another embodiment, the compound binds to a kinase enzyme exhibiting an ATP-dependent enzymatic activity. In another embodiment, the compound competes with ATP for binding to an ATP-binding site on the kinase. In another embodiment, the compound binds to a site other than an ATP-binding site on the kinase. In another embodiment, the kinase is a tyrosine kinase. In another embodiment, the tyrosine kinase is Abl kinase, BCR-Abl kinase, ARG kinase, src kinase, c-kit or platelet-derived growth factor receptor. In another embodiment, the kinase is a serine/threonine kinase, a carbohydrate kinase or a lipid kinase.

In another aspect, the invention provides a method for modulating Aβ levels exhibited by a cell or tissue comprising contacting said cell or tissue with an amount of an ATP modulator sufficient to modulate said Aβ levels.

In one embodiment, the Aβ levels are lowered. In another embodiment, the Aβ levels are raised. In another embodiment, the Aβ is Aβ40. In another embodiment, the Aβ is Aβ42.

In another embodiment, the modulating results in an increase in the ratio of Aβ40 to Aβ42. In another embodiment, the modulating results in an increase in C99. In another embodiment, the ATP modulator competes with ATP for binding to an ATP-binding site.

In another embodiment, the ATP-binding site is present on an enzyme that exhibits an ATP-dependent enzymatic activity. In another embodiment, the ATP-binding site is present on a molecule that regulates the ATP-dependent enzymatic activity. In another embodiment, the compound does not affect total cellular levels of β-amyloid precursor product (APP). In another embodiment, the compound does not decrease levels of secreted APP (sAPP). In another embodiment, the compound increases levels of sAPPα.

In another embodiment, levels of secreted Aβ are modulated.

In another embodiment, the compound does not inhibit Notch-1 cleavage. In another embodiment, the compound does not inhibit tau phosphorylation. In another embodiment, the compound crosses the blood-brain barrier. In another embodiment, the enzymatic activity is a γ-secretase activity. In another embodiment, the compound inhibits γ-secretase activity.

In another embodiment, the the compound is an ATP modulator. In another embodiment, the ATP modulator is a selective modulator. In another embodiment, the compound binds a γ-secretase enzyme exhibiting an ATP-dependent enzymatic activity.

In another embodiment, the compound is STI-571 or a blood-brain barrier permeable variant thereof, or a pharmaceutically acceptable salt thereof. In another embodiment, the compound is a mesylate salt of STI-571. In another embodiment, the compound is WGB-BC-15 or a blood-brain barrier permeable variant thereof, or a pharmaceutically acceptable salt thereof. In another embodiment, the compound is any of Compounds 1-5 or a blood-brain barrier permeable variant thereof, or a pharmaceutically acceptable salt thereof.

In another embodiment, the enzymatic activity is a kinase activity. In another embodiment, the compound binds to a kinase enzyme exhibiting an ATP-dependent enzymatic activity. In another embodiment, the compound competes with ATP for binding to an ATP-binding site on the kinase. In another embodiment, the compound binds to a site other than an ATP-binding site on the kinase. In another embodiment, the kinase is a tyrosine kinase. In another embodiment, the tyrosine kinase is Abl kinase, BCR-Abl kinase, ARG kinase, src kinase, c-kit or platelet-derived growth factor receptor. In another embodiment, the kinase is a serine/threonine kinase, a carbohydrate kinase or a lipid kinase. In another embodiment, the kinase is a serine/threonine kinase, a carbohydrate kinase or a lipid kinase.

In another embodiment, the compound competes with ATP for binding to a target other than γ-secretase in the metabolic pathway that regulates the cleavage of APP to Aβ by γ-secretase. In specific embodiments, the target is a kinase (or kinase domain), a protease (e.g., an AAA protease of the kind localized to the inner mitochondrial membrane), a phosphatase, or a molecular chaperone molecule (e.g., hsp 60, hsp70, hsp90).

In one aspect in the invention provides a method for modulating Aβ levels in a cell or tissue comprising contacting said cell or tissue with an amount of a compound sufficient to modulate said Aβ levels, wherein said compound contains the following pharmacophore:
wherein X is CH—, O, NH or N—CO—.

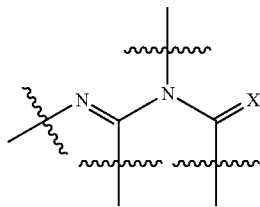

In one embodiment, said pharmacophore containing compound comprises a compound of Figure I or a pharmaceutically acceptable salt thereof:
Figure I

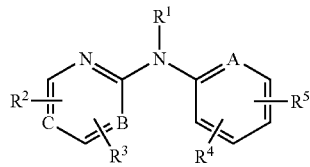

A is CH or N;
B and C are independently CH, N or N$^+$—O—;
R$^1$ is H, SO$_2$R$^a$, (C=O)$_r$O$_s$R$^a$;
R$^2$, R$^3$, R$^4$ and R$^5$ are independently H, OH, CHO, CN, halogen, (C=O)$_r$O$_s$(C$_1$-C$_{10}$)alkyl, (C=O)$_r$O$_s$(C$_2$-C$_{10}$)alkyl, (C=O)$_r$O$_s$(C$_2$-C$_{10}$)alkynyl, (C=O)$_r$O$_s$cycloalkyl, (C=O)$_r$O$_s$cycloalkenyl, (C=O)$_r$O$_s$cycloalkynyl, (C=O)$_r$O$_s$heterocycyl, (C=O)$_r$O$_s$aryl, (C=O)$_r$O$_s$heteroaryl, (C=O)$_r$O$_s$perfluoroalkyl or (C$_0$-C$_6$)alkyl-NR$^b$R$^c$, wherein said alkykl, alkenyl, alkynyl, cycyloalkyl, cycloalkenyl, cycloalkynyl, heterocycyl, aryl, heteroaryl and perfluoroalkyl is optionally substituted with one or more substituents selected from R$^6$;
R$^6$ is (C=O)$_r$O$_s$NR$^a$R$^b$, (C=O)$_r$O$_s$aryl, (C=O)$_r$O$_s$heterocycyl, halogen, OH, oxo, (C=O)$_r$O$_s$(C$_1$-C$_3$)perfluoroalkyl, (C=O)$_r$O$_s$(C$_1$-C$_6$)alkyl, CHO, CO$_2$H, CN, (C$_0$-C$_6$)alkyl-NR$^b$R$^c$ or (C$_1$-C$_6$)alkyl-heterocycyl,
wherein said alkyl-heterocycyl is optionally substituted with OH;
R$^a$ is (C$_1$-C$_6$)alkyl, aryl or heterocycyl; and
R$^b$ and R$^c$ independently are H, (C=O)$_r$O$_s$(C$_1$-C$_{10}$)alkyl, SO$_2$R$^a$, (C=O)$_r$O$_s$heterocycyl, (C=O)$_r$O$_s$aryl, (C=O)$_r$O$_s$heteroaryl or CO$_2$R$^a$,
wherein r and s independently are 0 or 1 and said alkyl, heterocycyl, aryl or heteroaryl is optionally substituted with one or more substituents selected from R$^6$.

In another embodiment, A is CH, B is N and C is CH.
In another embodiment, R$^1$ is H.
In another embodiment, R$^2$ is H and R$^3$ is heteroaryl.
In another embodiment, R$^4$ is (C=O)$_r$O$_s$(C$_1$-C$_{10}$)alkyl and R$^5$ is (C$_0$-C$_6$)alkyl-NR$^b$R$^c$.
In another embodiment, R$^3$ is 3-pyridinyl.
In another embodiment, r is 0, s is 0 and (C$_1$-C$_{10}$)alkyl is methyl.
In another embodiment, (C$_0$-C$_6$)alkyl is a direct bond (C$_0$), R$^b$ is H and R$^c$ is (C=O)$_r$O$_s$heteroaryl or (C=O)$_r$O$_s$heterocycyl.
In another embodiment, (C=O)$_r$O$_s$heterocycyl is 4-hydroxy-1-piperazino, as illustrated below or a pharmaceutically acceptable salt thereof

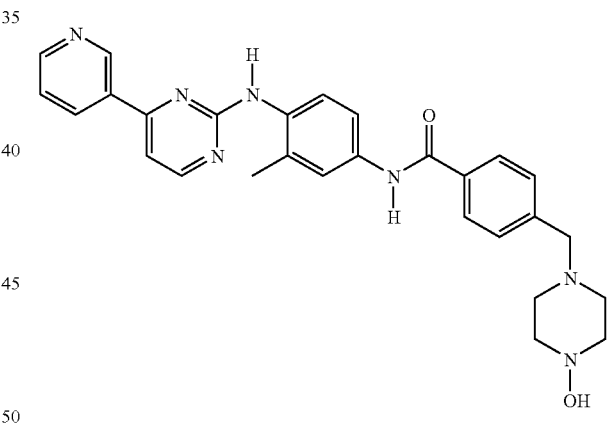

In another embodiment, (C=O)$_r$O$_s$heteroaryl is 3-pyrindinyl, as illustrated below or a pharmaceutically acceptable salt thereof.

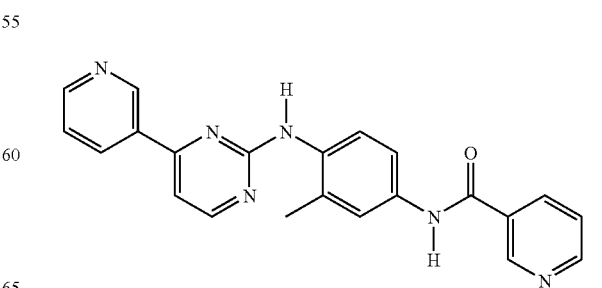

In another embodiment, said pharmacophore containing compound, comprises a compound of Figure II or a pharmaceutically acceptable salt thereof:

Figure II

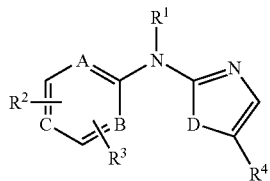

A, B and C are independently CH, N or N⁺—O—;
D is O, S or N—R⁵;
R¹ is H, SO₂Rᵃ, (C=O)ᵣRᵃ or CO₂Rᵃ;
R², R³ and R⁴ are independently H, OH, CHO, CN, halogen, (C=O)ᵣOₛ(C₁-C₁₀)alkyl, (C=O)ᵣOₛ(C₂-C₁₀)alkenyl, (C=O)ᵣOₛ(C₂-C₁₀)alkynyl, (C=O)ᵣOₛcycloalkyl, (C=O)ᵣOₛcycloalkenyl, (C=O)ᵣOₛcycloalkynyl, (C=O)ᵣOₛheterocycyl, (C=O)ᵣOₛaryl, (C=O)ᵣOₛheteroaryl, (C=O)ᵣOₛperfluoroalkyl or (C₀-C₆)alkyl-NRᵇRᶜ, wherein said alkykl, alkenyl, alkynyl, cycyloalkyl, cycloalkenyl, cycloalkynyl, heterocycyl, aryl, heteroaryl and perfluoroalkyl is optionally substituted with one or more substituents selected from R⁶;

R⁵ is H, aryl or (C₁-C₆)alkyl;
R⁶ is (C=O)ᵣOₛNRᵃRᵇ, (C=O)ᵣOₛaryl, (C=O)ᵣOₛheterocycyl, halogen, OH, oxo, (C=O)ᵣOₛ(C₁-C₃)perfluoroalkyl, (C=O)ᵣOₛ(C₁-C₆)alkyl, CHO, CO₂H, CN, (C₀-C₆)alkyl-NRᵇRᶜ or (C₁-C₆)alkyl-heterocycyl;
Rᵃ is (C₁-C₆)alkyl, aryl or heterocycyl; and
Rᵇ and Rᶜ independently are H, (C=O)ᵣOₛ(C₁-C₁₀)alkyl, SO₂Rᵃ, (C=O)ᵣOₛheterocycyl, (C=O)ᵣOₛaryl, (C=O)ᵣOₛheteroaryl or CO₂Rᵃ, wherein r and s independently are 0 or 1 and said alkyl, heterocycyl, aryl or heteroaryl is optionally substituted with one or more substituents selected from R⁶.

In another embodiment, R¹ is H.
In another embodiment, R² is H and R³ is (C₀-C₆)alkyl-NRᵇRᶜ.
In another embodiment, R⁴ is heteroaryl.
In another embodiment, said pharmacophore containing compound, comprises a compound of Figure III or a pharmaceutically acceptable salt thereof:

Figure III

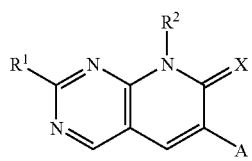

A is aryl or heteroaryl,
wherein said aryl or heteroaryl is optionally substituted with one or more substituents selected from R³;
X is NH, N-acyl, O or S;
R¹ and R² are independently H, OH, CHO, CN, halogen, (C=O)ᵣOₛ(C₁-C₁₀)alkyl, (C=O)ᵣOₛ(C₂-C₁₀)alkenyl, (C=O)ᵣOₛ(C₂-C₁₀)alkynyl, (C=O)ᵣOₛcycloalkyl, (C=O)ᵣOₛcycloalkenyl, (C=O)ᵣOₛcycloalkynyl, (C=O)ᵣOₛheterocycyl, (C=O)ᵣOₛaryl, (C=O)ᵣOₛheteroaryl, (C=O)ᵣOₛperfluoroalkyl or (C₀-C₆)alkyl-NRᵃRᵇ, wherein said alkykl, alkenyl, alkynyl, cycyloalkyl, cycloalkenyl, cycloalkynyl, heterocycyl, aryl, heteroaryl and perfluoroalkyl is optionally substituted with one or more substituents selected from R³;

R³ is (C=O)ᵣOₛNRᵃRᵇ, (C=O)ᵣOₛaryl, (C=O)ᵣOₛheterocycyl, halogen, OH, oxo, (C=O)ᵣOₛ(C₁-C₃)perfluoroalkyl, (C=O)ᵣOₛ(C₁-C₆)alkyl, CHO, CO₂H, CN, (C₀-C₆)alkyl-NRᵃRᵇ or (C₁-C₆)alkyl-heterocycyl;
Rᵃ and Rᵇ independently are H, (C=O)ᵣOₛ(C₁-C₁₀)alkyl, SO₂R¹, (C=O)ᵣOₛheterocycyl, (C=O)ᵣOₛaryl, (C=O)ᵣOₛheteroaryl or CO₂R¹, wherein r, s and t independently are 0 or 1 and said alkyl, heterocycyl, aryl or heteroaryl is optionally substituted with one or more substituents selected from R³.

In another embodiment, A is aryl.
In another embodiment, the aryl is 2,5-dichlorophenyl.
In another embodiment, R¹ is (C₀-C₆)alkyl-NRᵃRᵇ and R² is (C=O)ᵣOₛ(C₁-C₁₀)alkyl.
In another embodiment, (C=O)ᵣOₛ(C₁-C₁₀)alkyl is methyl.
In another embodiment, (C₀-C₆)alkyl-NRᵃRᵇ is

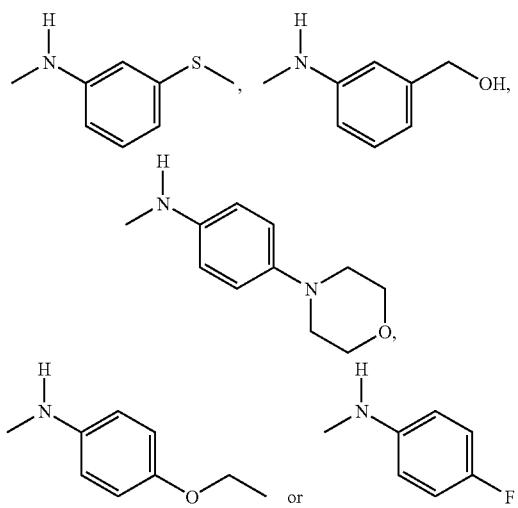

or a pharmaceutically acceptable salt thereof.

In another aspect, the invention provides a pharmaceutical composition useful for modulating Aβ level in a cell or tissue, comprising:
an amount of a compound described in any one of claims 1 to 21 sufficient to modulate said Aβ level; and
a pharmaceutically acceptable excipient or carrier.

In one embodiment, the pharmaceutical composition is useful for modulating Aβ levels exhibited by a cell or tissue.

In another embodiment, the compound is present in an amount sufficient to modulate said Aβ levels.

Compounds according to Figure I may be prepared by various processes known to one of skill in the art. In particular, compounds according to Figure I, wherein A is CH, B is N, C is CH and R$^1$ is H may be prepared by the following process:

a) a compound according to Figure IV

Figure IV

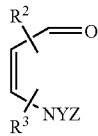

wherein Y and Z constitute (C$_1$-C$_6$)alkyl groups and R$^2$ and R$^3$ are as above-defined is reacted with a compound according to Figure V

Figure V

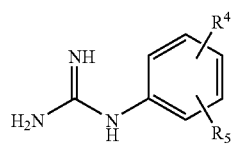

wherein R$^4$ and R$^5$ are as above-defined.

In one embodiment, a compound utilized by the methods of the invention contains the following pharmacophore:

wherein X is CH—, O, NH or N—CO—.

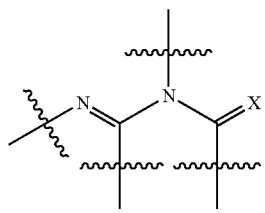

In one embodiment, said pharmacophore containing compound comprises a compound of Figure I or a pharmaceutically acceptable salt thereof:

Figure I

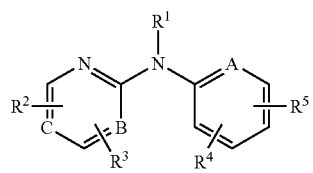

A is CH or N;

B and C are independently CH, N or N$^+$—O—;

R$^1$ is H, SO$_2$R$^a$, (C=O)$_r$O$_s$R$^a$;

R$^2$, R$^3$, R$^4$ and R$^5$ are independently H, OH, CHO, CN, halogen, (C=O)$_r$O$_s$(C$_1$-C$_{10}$)alkyl, (C=O)$_r$O$_s$(C$_2$-C$_{10}$)alkenyl, (C=O)$_r$O$_s$(C$_2$-C$_{10}$)alkynyl, (C=O)$_r$O$_s$cycloalkyl, (C=O)$_r$O$_s$cycloalkenyl, (C=O)$_r$O$_s$cycloalkynyl, (C=O)$_r$O$_s$heterocycyl, (C=O)$_r$O$_s$aryl, (C=O)$_r$O$_s$heteroaryl, (C=O)$_r$O$_s$perfluoroalkyl or (C$_0$-C$_6$)alkyl-NR$^b$R$^c$, wherein said alkykl, alkenyl, alkynyl, cycyloalkyl, cycloalkenyl, cycloalkynyl, heterocycyl, aryl, heteroaryl and perfluoroalkyl is optionally substituted with one or more substituents selected from R$^6$;

R$^6$ is (C=O)$_r$O$_s$NR$^a$R$^b$, (C=O)$_r$O$_s$aryl, (C=O)$_r$O$_s$heterocycyl, halogen, OH, oxo, (C=O)$_r$O$_s$(C$_1$-C$_3$)perfluoroalkyl, (C=O)$_r$O$_s$(C$_1$-C$_6$)alkyl, CHO, CO$_2$H, CN, (C$_0$-C$_6$)alkyl-NR$^b$R$^c$ or (C$_1$-C$_6$)alkyl-heterocycyl, wherein said alkyl-heterocycyl is optionally substituted with OH;

R$^a$ is (C$_1$-C$_6$)alkyl, aryl or heterocycyl; and

R$^b$ and R$^c$ independently are H, (C=O)$_r$O$_s$(C$_1$-C$_{10}$)alkyl, SO$_2$R$^a$, (C=O)$_r$O$_s$heterocycyl, (C=O)$_r$O$_s$aryl, (C=O)$_r$O$_s$heteroaryl or CO$_2$R$^a$, wherein r and s independently are 0 or 1 and said alkyl, heterocycyl, aryl or heteroaryl is optionally substituted with one or more substituents selected from R$^6$.

In another embodiment, A is CH, B is N and C is CH.

In another embodiment, R$^1$ is H.

In another embodiment, R$^2$ is H and R$^3$ is heteroaryl.

In another embodiment, R$^4$ is (C=O)$_r$O$_s$(C$_1$-C$_{10}$)alkyl and R$^5$ is (C$_0$-C$_6$)alkyl-NR$^b$R$^c$.

In another embodiment, R$^3$ is 3-pyridinyl.

In another embodiment, r is 0, s is 0 and (C$_1$-C$_{10}$)alkyl is methyl.

In another embodiment, (C$_0$-C$_6$)alkyl is a direct bond (C$_0$), R$^b$ is H and R$^c$ is (C=O)$_r$O$_s$heteroaryl or (C=O)$_r$O$_s$heterocycyl.

In another embodiment, (C=O)$_r$O$_s$heterocycyl is 4-hydroxy-1-piperazino, as illustrated below or a pharmaceutically acceptable salt thereof.

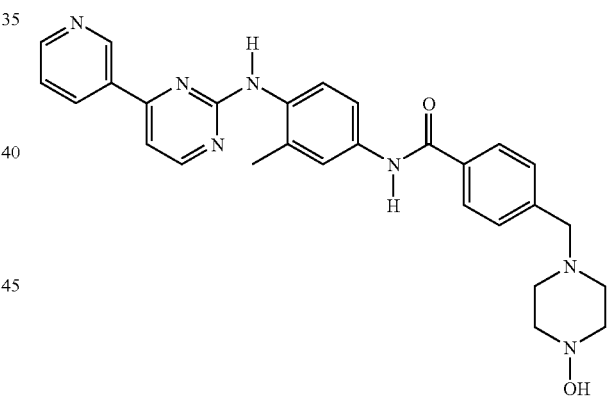

In another embodiment, (C=O)$_r$O$_s$heteroaryl is 3-pyrindinyl, as illustrated below or a pharmaceutically acceptable salt thereof.

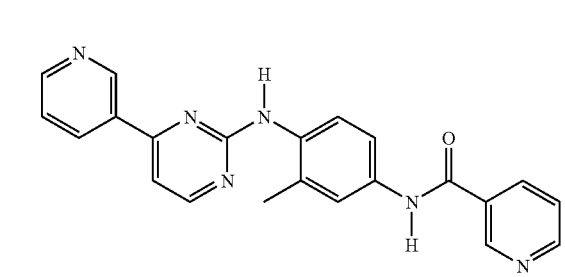

In another embodiment, said pharmacophore containing compound, comprises a compound of Figure II or a pharmaceutically acceptable salt thereof:

Figure II

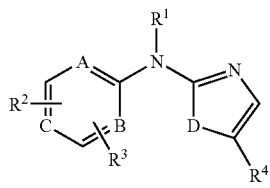

A, B and C are independently CH, N or N⁺—O—;

D is O, S or N—$R^5$;

$R^1$ is H, $SO_2R^a$, $(C=O)_rR^a$ or $CO_2R^a$;

$R^2$, $R^3$ and $R^4$ are independently H, OH, CHO, CN, halogen, $(C=O)_rO_s(C_1-C_{10})$alkyl, $(C=O)_rO_s(C_2-C_{10})$alkenyl, $(C=O)_rO_s(C_2-C_{10})$alkynyl, $(C=O)_rO_s$cycloalkyl, $(C=O)_rO_s$cycloalkenyl, $(C=O)_rO_s$cycloalkynyl, $(C=O)_rO_s$heterocycyl, $(C=O)_rO_s$aryl, $(C=O)_rO_s$heteroaryl, $(C=O)_rO_s$perfluoroalkyl or $(C_0-C_6)$alkyl-$NR^bR^c$, wherein said alkykl, alkenyl, alkynyl, cycyloalkyl, cycloalkenyl, cycloalkynyl, heterocycyl, aryl, heteroaryl and perfluoroalkyl is optionally substituted with one or more substituents selected from $R^6$;

$R^5$ is H, aryl or $(C_1-C_6)$alkyl;

$R^6$ is $(C=O)_rO_sNR^aR^b$, $(C=O)_rO_s$aryl, $(C=O)_rO_s$heterocycyl, halogen, OH, oxo, $(C=O)_rO_s(C_1-C_3)$perfluoroalkyl, $(C=O)_rO_s(C_1-C_6)$alkyl, CHO, $CO_2H$, CN, $(C_0-C_6)$alkyl-$NR^bR^c$ or $(C_1-C_6)$alkyl-heterocycyl;

$R^a$ is $(C_1-C_6)$alkyl, aryl or heterocycyl; and $R^b$ and $R^c$ independently are H, $(C=O)_rO_s(C_1-C_{10})$alkyl, $SO_2R^a$, $(C=O)_rO_s$heterocycyl, $(C=O)_rO_s$aryl, $(C=O)_rO_s$heteroaryl or $CO_2R^a$ wherein r and s independently are 0 or 1 and said alkyl, heterocycyl, aryl or heteroaryl is optionally substituted with one or more substituents selected from $R^6$.

In another embodiment, $R^1$ is H.

In another embodiment, $R^2$ is H and $R^3$ is $(C_0-C_6)$alkyl-$NR^bR^c$.

In another embodiment, $R^4$ is heteroaryl.

In another embodiment, said pharmacophore containing compound, comprises a compound of Figure III or a pharmaceutically acceptable salt thereof:

Figure III

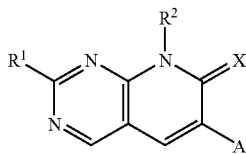

A is aryl or heteroaryl, wherein said aryl or heteroaryl is optionally substituted with one or more substituents selected from $R^3$;

X is NH, N-acyl, O or S;

$R^1$ and $R^2$ are independently H, OH, CHO, CN, halogen, $(C=O)_rO_s(C_1-C_{10})$alkyl, $(C=O)_rO_s(C_2-C_{10})$alkenyl, $(C=O)_rO_s(C_2-C_{10})$alkynyl, $(C=O)_rO_s$cycloalkyl, $(C=O)_rO_s$cycloalkenyl, $(C=O)_rO_s$cycloalkynyl, $(C=O)_rO_s$heterocycyl, $(C=O)_rO_s$aryl, $(C=O)_rO_s$heteroaryl, $(C=O)_rO_s$perfluoroalkyl or $(C_0-C_6)$alkyl-$NR^aR^b$, wherein said alkykl, alkenyl, alkynyl, cycyloalkyl, cycloalkenyl, cycloalkynyl, heterocycyl, aryl, heteroaryl and perfluoroalkyl is optionally substituted with one or more substituents selected from $R^3$;

$R^3$ is $(C=O)_rO_sNR^aR^b$, $(C=O)_rO_s$aryl, $(C=O)_rO_s$heterocycyl, halogen, OH, oxo, $(C=O)_rO_s(C_1-C_3)$perfluoroalkyl, $(C=O)_rO_sS_t(C_1-C_6)$alkyl, CHO, $CO_2H$, CN, $(C_0-C_6)$alkyl-$NR^aR^b$ or $(C_1-C_6)$alkyl-heterocycyl;

$R^a$ and $R^b$ independently are H, $(C=O)_rO_s(C_1-C_{10})$alkyl, $SO_2R^1$, $(C=O)_rO_s$heterocycyl, $(C=O)_rO_s$aryl, $(C=O)_rO_s$heteroaryl or $CO_2R^1$, wherein r, s and t independently are 0 or 1 and said alkyl, heterocycyl, aryl or heteroaryl is optionally substituted with one or more substituents selected from $R^3$.

In another embodiment, A is aryl.

In another embodiment, the aryl is 2,5-dichlorophenyl.

In another embodiment, $R^1$ is $(C_0-C_6)$alkyl-$NR^aR^1$ and $R^2$ is $(C=O)_rO_s(C_1-C_{10})$alkyl.

In another embodiment, $(C=O)_rO_s(C_1-C_{10})$alkyl is methyl.

In another embodiment, $(C_0-C_6)$alkyl-$NR^aR^b$ is

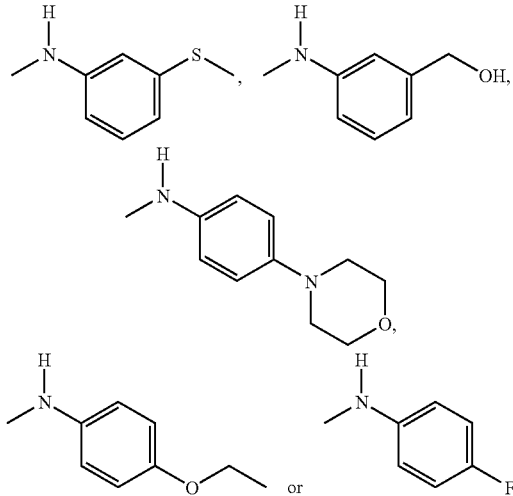

or a pharmaceutically acceptable salt thereof.

The invention also provides an article of manufacture comprising packaging material and a pharmaceutical composition comprising a compound that lowers ATP-dependent Aβ levels, and a pharmaceutically acceptable carrier contained within the packaging material, said pharmaceutical composition in a form suitable for administration to a subject. In one embodiment, the article of manufacture further comprises printed instructions regarding the use or administration of the pharmaceutical composition. In one embodiment, the instructions suggest a dosing regimen for the prevention, treatment, or amelioration of a symptom of an Aβ-related disorder. In another embodiment, the instructions suggest a dosing regimen for the prevention, treatment, or amelioration of a symptom of Alzheimer's disease.

In another embodiment, the article of manufacture further comprises a label regarding the use or administration of the pharmaceutical composition. In another embodiment, the label suggests a dosing regimen for the prevention, treatment, or amelioration of a symptom of an Aβ-related disorder. In another embodiment, the label suggests a dosing regimen for the prevention, treatment, or amelioration of a symptom of Alzheimer's disease.

In another embodiment, the article of manufacture further comprises an antioxidant, a non-selective COX inhibitor or an acetylcholinesterase inhibitor. In another embodiment, the pharmaceutical composition further comprises an antioxidant, a non-selective COX inhibitor or an acetylcholinesterase inhibitor.

The invention also provides method of identifying a compound that modulates Aβ levels exhibited by a cell or tissue comprising:
 (a) determining a first level of γ-secretase activity in said cell or tissue;
 (b) contacting said cell or tissue with a test compound; and
 (c) determining a second level of γ-secretase activity in said cell or tissue,
wherein a difference in said first level and said second level of γ-secretase activity is indicative of the ability of said test compound to modulate Aβ levels.

In one embodiment, the difference in γ-secretase activity is indicative of the ability of said test compound to modulate the Aβ levels. In another embodiment, Aβ levels are modulated. In another embodiment, the γ-secretase activity is an ATP-dependent enzymatic activity. In another embodiment, the γ-secretase activity is production of Aβ.

The invention also provides a method of identifying a compound that modulates Aβ levels exhibited by a cell or tissue comprising:
 (a) contacting said cell or tissue with a test compound; and
 (b) determining a level of activity of γ-secretase in said cell or tissue;
wherein a difference in said level and a control level of γ-secretase activity in a comparable cell or tissue not contacted with the test compound is indicative of the ability of said test compound to modulate Aβ levels.

In one embodiment, the difference in γ-secretase activity is indicative of the ability of said test compound to modulate the Aβ levels. In another embodiment, Aβ levels are modulated. In another embodiment, the γ-secretase activity is an ATP-dependent enzymatic activity. In another embodiment, the γ-secretase activity is production of Aβ.

The invention also provides a method for identifying an agent to be tested for an ability to treat an Aβ-related disorder in a patient in need of such treatment comprising:
 (a) contacting in a cell or tissue γ-secretase with a potential agent; and
 (b) detecting the amount of γ-secretase activity
wherein the agent is identified if a decrease in γ-secretase activity is detected in the presence of the potential agent and wherein the agent modulates Aβ levels.

In one embodiment, the ability to treat the Aβ-related disorder is tested. In another embodiment, the γ-secretase activity is an ATP-dependent enzymatic activity. In another embodiment, the γ-secretase activity is production of Aβ.

In another aspect, the invention provides a method for identifying an agent to be tested for an ability to modulate Aβ levels exhibited by a cell or tissue comprising:
 (a) determining a first level of γ-secretase activity in said cell or tissue;
 (b) contacting said cell or tissue with a potential agent; and
 (c) determining a second level of γ-secretase activity in said cell or tissue, wherein a difference in said first level and said second level of γ-secretase activity is indicative of the ability of said potential agent to modulate Aβ levels.

In one embodiment, the method comprises the additional step of:
 (d) determining whether the Aβ levels are modulated.

In another embodiment, the γ-secretase activity is an ATP-dependent enzymatic activity. In another embodiment, the γ-secretase activity is production of Aβ.

The invention also provides a method for identifying an agent to be tested for an ability to modulate Aβ levels exhibited by a cell or tissue comprising:
 (a) contacting said cell or tissue with a potential agent; and
 (b) determining a level of γ-secretase activity in said cell or tissue;
wherein a difference in said level and a control level of γ-secretase activity in a comparable cell or tissue not contacted with the test compound is indicative of the ability of said potential agent to modulate Aβ levels.

In one embodiment, the method comprises the additional step of:
 (c) determining whether the Aβ levels are modulated.

In another embodiment, the γ-secretase activity is an ATP-dependent enzymatic activity.

In another embodiment, the γ-secretase activity is production of Aβ.

The invention also provides a method for selecting a potential therapeutic agent for use in the treatment of an Aβ-related disorder comprising:
 (a) administering a potential therapeutic agent to an animal;
 (b) measuring the response of said animal to said potential therapeutic agent;
 (c) comparing the response of said animal with that of a control animal to which the potential therapeutic agent has not been administered; and
 (d) selecting a potential therapeutic agent based on the difference in responses observed between said animal and said control animal,
wherein the potential therapeutic agent modulates ATP-dependent γ-secretase activity.

In one embodiment, the animal is a guinea pig. In another embodiment, the disorder is Alzheimer's disease.

The invention also provides a method for selecting a potential therapeutic agent for use in the treatment of an Aβ-related disorder comprising:
 (a) administering a potential therapeutic agent to an animal;
 (b) measuring the response of said animal to administration of an agent that modulates activity of γ-secretase;
 (c) comparing the response of said animal with that of a control animal to which the potential therapeutic agent has not been administered; and
 (d) selecting a potential therapeutic agent based on the difference in responses observed between said animal and said control animal,
wherein the potential therapeutic agent modulates ATP-dependent γ-secretase activity.

In one embodiment, the animal is a guinea pig. In another embodiment, the disorder is Alzheimer's disease.

The invention also provides a method for selecting a potential therapeutic agent for use in the treatment of an Aβ-related disorder comprising:
 (a) administering a potential therapeutic agent to an animal;
 (b) measuring the response of said animal, wherein the response is selected from the group consisting of:
  (i) exhibition of behavior in a Morris water maze; and
  (i) exhibition of behavior in a Y-maze (c) comparing the response of said animal with that of a control animal to which the potential therapeutic agent has not been administered; and (d) selecting a potential therapeutic agent based on the difference in responses observed between said animal and said control animal, wherein the potential therapeutic agent modulates Aβ levels.

In one embodiment, the animal is a guinea pig. In another embodiment, the disorder is Alzheimer's disease.

The invention also provides a method for preventing, delaying or reversing the progression of an Aβ-related disorder comprising:

(a) identifying a mammal in need of prevention, delay, or reversal of the progression of the disorder; and (b) administering to said mammal an amount of an agent sufficient to modulate ATP-dependent γ-secretase activity, wherein Aβ levels are modulated.

In one embodiment, the agent inhibits or decreases ATP-dependent γ-secretase activity.

In another embodiment, the mammal is human. In another embodiment, the disorder is Alzheimer's disease.

In another embodiment, the agent promotes or increases ATP-dependent γ-secretase activity.

In another embodiment, the agent is administered orally.

In another embodiment, the agent is administered with a NSAID. In specific embodiment, the NSAID is sulindac sulfide, flufenamic acid, ibuprofen, flurbiprofen, fenoprofen, mefenamic acid, indomethacin, carprofen, meclofenamic acid.

In another embodiment, the agent is administered with an antioxidant. In another embodiment, the antioxidant is selected from the group consisting of vitamin E, vitamin C, curcumin, and Gingko biloba.

In another embodiment, the agent the agent is administered with an acetylcholinesterase inhibitor.

The invention also provides a method of treating, or ameliorating a symptom of, an Aβ-related disorder comprising administering to a subject in need of such treating or ameliorating an amount of a compound sufficient to reduce Aβ levels in the subject, wherein the compound modulates an ATP-dependent enzymatic activity, such that the Aβ-related disorder is treated or a symptom of the Aβ related disorder is ameliorated.

In one embodiment, the Aβ related disorder is Alzheimer's disease. In another embodiment, progression of the Aβ related disorder is slowed. In another embodiment, progression of the Aβ related disorder is reversed.

In another embodiment, the subject is a human subject. In a specific embodiment, the subject is a subject at risk for a familial form of Alzheimer's disease.

In another embodiment, the ATP-dependent enzymatic activity is lowered. In another embodiment, the compound crosses the blood-brain barrier. In another embodiment, the compound is administered orally.

In another embodiment, the compound is administered with a NSAID. In a specific embodiment, the NSAID is sulindac sulfide, flufenamic acid, ibuprofen, flurbiprofen, fenoprofen, mefenamic acid, indomethacin, carprofen, meclofenamic acid.

In another embodiment, the compound is administered with an antioxidant. In a specific embodiment, the antioxidant is selected from the group consisting of vitamin E, vitamin C, curcumin, and Gingko biloba.

In another embodiment, the compound is administered with an acetylcholinesterase inhibitor.

In another embodiment, the compound is an ATP modulator. In another embodiment, the compound is ATP modulator is a selective modulator.

In another embodiment, the enzymatic activity is a γ-secretase activity. In another embodiment, the compound binds a γ-secretase enzyme exhibiting an ATP-dependent enzymatic activity.

In another embodiment, the ATP modulator competes with ATP for binding to an ATP binding site.

In one embodiment, the compound is STI-571 or a blood-brain barrier permeable variant thereof, or a pharmaceutically acceptable salt thereof. In another embodiment, the compound is a mesylate salt of STI-571. In another embodiment, the compound is WGB-BC-15 or a blood-brain barrier permeable variant thereof, or a pharmaceutically acceptable salt thereof. In another embodiment, the compound is any of Compounds 1-5 or a blood-brain barrier permeable variant thereof, or a pharmaceutically acceptable salt thereof.

In one embodiment, the enzymatic activity is a kinase activity. In one embodiment, the compound binds to a kinase enzyme exhibiting an ATP-dependent enzymatic activity. In one embodiment, the compound competes with ATP for binding to an ATP-binding site on the kinase. In another embodiment, the compound binds to a site other than an ATP-binding site on the kinase.

In a specific embodiment, the kinase is a tyrosine kinase. In another embodiment, the tyrosine kinase is Abl kinase, BCR-Abl kinase, ARG kinase, src kinase, c-kit, platelet-derived growth factor receptor.

In a specific embodiment, the kinase is a serine/threonine kinase, a carbohydrate kinase or a lipid kinase.

In another embodiment, the enzymatic activity is activity of a protease (e.g., AAA protease of the kind localized to the inner mitochondrial membrane), phosphatase, or a molecular chaperone molecule (e.g., hsp 60, hsp70, hsp90).

The invention also provides a method of treating, or ameliorating a symptom of, an Aβ-related disorder comprising administering to a subject in need of such treating or ameliorating an amount of an ATP modulator sufficient to reduce Aβ levels in the subject, such that the Aβ-related disorder is treated or a symptom of the Aβ related disorder is ameliorated.

In one embodiment, the Aβ related disorder is Alzheimer's disease. In one embodiment, the subject is a human subject. In another embodiment, In one embodiment, the subject is a subject at risk for a familial form of Alzheimer's disease.

In another embodiment, the ATP-dependent enzymatic activity is lowered.

In another embodiment, the ATP modulator crosses the blood-brain barrier.

In another embodiment, the ATP modulator is administered orally. In another embodiment, the ATP modulator is administered with a NSAID. In another embodiment, the NSAID is sulindac sulfide, flufenamic acid, ibuprofen, flurbiprofen, fenoprofen, mefenamic acid, indomethacin, carprofen, meclofenamic acid.

In another embodiment, the ATP modulator is administered with an antioxidant. In another embodiment, the antioxidant is selected from the group consisting of vitamin E, vitamin C, curcumin, and Gingko biloba.

In another embodiment, the ATP modulator is administered with an acetylcholinesterase inhibitor.

In another embodiment, the ATP modulator is a selective modulator.

In another embodiment, the enzymatic activity is a γ-secretase activity.

In one embodiment, the compound binds a γ-secretase enzyme exhibiting an ATP-dependent enzymatic activity. In another embodiment, the ATP modulator competes with ATP for binding to an ATP binding site.

In one embodiment, the compound is STI-571 or a blood-brain barrier permeable variant thereof, or a pharmaceutically acceptable salt thereof. In another embodiment, the compound is a mesylate salt of STI-571. In another embodiment, the compound is WGB-BC-15 or a blood-brain barrier permeable variant thereof, or a pharmaceutically acceptable salt thereof. In another embodiment, the compound is any of Compounds 1-5 or a blood-brain barrier permeable variant thereof, or a pharmaceutically acceptable salt thereof.

In one embodiment, the enzymatic activity is a kinase activity. In one embodiment, the compound binds to a kinase enzyme exhibiting an ATP-dependent enzymatic activity. In one embodiment, the compound competes with ATP for binding to an ATP-binding site on the kinase. In another embodiment, the compound binds to a site other than an ATP-binding site on the kinase.

In a specific embodiment, the kinase is a tyrosine kinase. In another embodiment, the tyrosine kinase is Abl kinase, BCR-Abl kinase, ARG kinase, src kinase, c-kit, platelet-derived growth factor receptor.

In a specific embodiment, the kinase is a serine/threonine kinase, a carbohydrate kinase or a lipid kinase.

In another embodiment, the enzymatic activity is activity of a protease (e.g., AAA protease of the kind localized to the inner mitochondrial membrane), phosphatase, or a molecular chaperone molecule (e.g., hsp 60, hsp70, hsp90).

The invention also provides a method of treating, or ameliorating a symptom of, an Aβ-related disorder comprising administering to a subject in need of such treating or ameliorating an amount of a compound sufficient to reduce Aβ levels in the subject, such that the Aβ-related disorder is treated or a symptom of the Aβ-related disorder is ameliorated, wherein the compound contains the following pharmacophore:
wherein X is CH—, O, NH or N—CO—.

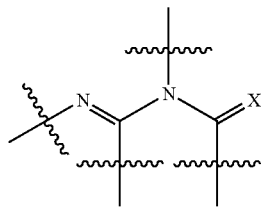

In one embodiment, said pharmacophore containing compound comprises a compound of Figure I or a pharmaceutically acceptable salt thereof:
Figure I

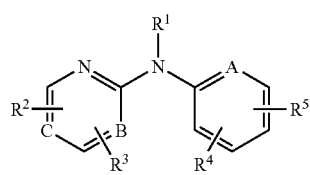

A is CH or N;
B and C are independently CH, N or $N^+$—O—;
$R^1$ is H, $SO_2R^a$, $(C=O)_rO_sR^a$;

$R^2$, $R^3$, $R^4$ and $R^5$ are independently H, OH, CHO, CN, halogen, $(C=O)_rO_s(C_1-C_{10})$alkyl, $(C=O)_rO_s(C_2-C_{10})$alkenyl, $(C=O)_rO_s(C_2-C_{10})$alkynyl, $(C=O)_rO_s$cycloalkyl, $(C=O)_rO_s$cycloalkenyl, $(C=O)_rO_s$cycloalkynyl, $(C=O)_rO_s$heterocycyl, $(C=O)_rO_s$aryl, $(C=O)_rO_s$heteroaryl, $(C=O)_rO_s$perfluoroalkyl or $(C_0-C_6)$alkyl-$NR^bR^c$, wherein said alkykl, alkenyl, alkynyl, cycyloalkyl, cycloalkenyl, cycloalkynyl, heterocycyl, aryl, heteroaryl and perfluoroalkyl is optionally substituted with one or more substituents selected from $R^6$;

$R^6$ is $(C=O)_rO_sNR^aR^b$, $(C=O)_rO_s$aryl, $(C=O)_rO_s$heterocycyl, halogen, OH, oxo, $(C=O)_rO_s(C_1-C_3)$perfluoroalkyl, $(C=O)_rO_s(C_1-C_6)$alkyl, CHO, $CO_2H$, CN, $(C_0-C_6)$alkyl-$NR^bR^c$ or $(C_1-C_6)$alkyl-heterocycyl, wherein said alkyl-heterocycyl is optionally substituted with OH;

$R^a$ is $(C_1-C_6)$alkyl, aryl or heterocycyl; and $R^b$ and $R^c$ independently are H, $(C=O)_rO_s(C_1-C_{10})$alkyl, $SO_2R^a$, $(C=O)_rO_s$heterocycyl, $(C=O)_rO_s$aryl, $(C=O)_rO_s$heteroaryl or $CO_2R^a$, wherein r and s independently are 0 or 1 and said alkyl, heterocycyl, aryl or heteroaryl is optionally substituted with one or more substituents selected from $R^6$.

In another embodiment, A is CH, B is N and C is CH.

In another embodiment, $R^1$ is H.

In another embodiment, $R^2$ is H and $R^3$ is heteroaryl.

In another embodiment, $R^4$ is $(C=O)_rO_s(C_1-C_{10})$alkyl and $R^5$ is $(CO—C_6)$alkyl-$NR^bR^c$.

In another embodiment, $R^3$ is 3-pyridinyl.

In another embodiment, r is 0, s is 0 and $(C_1-C_{10})$alkyl is methyl.

In another embodiment, $(C_0-C_6)$alkyl is a direct bond $(C_0)$, $R^b$ is H and $R^c$ is $(C=O)_rO_s$heteroaryl or $(C=O)_rO_s$heterocycyl.

In another embodiment, $(C=O)_rO_s$heterocycyl is 4-hydroxy-1-piperazino, as illustrated below or a pharmaceutically acceptable salt thereof.

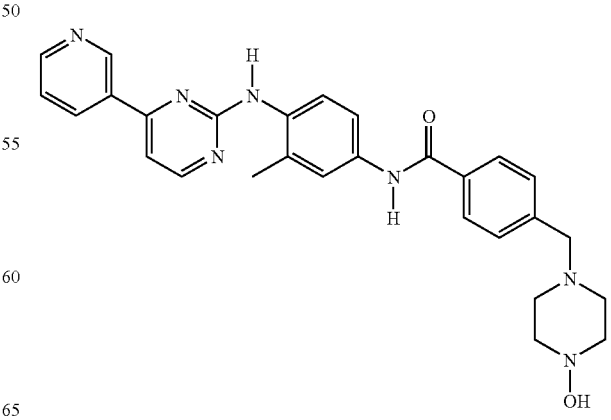

In another embodiment, the pharmacophore containing compound comprises a compound of Figure II or a pharmaceutically acceptable salt thereof:

Figure II

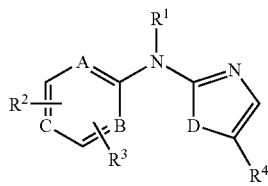

A, B and C are independently CH, N or N$^+$—O—;

D is O, S or N—R$^5$;

R$^1$ is H, SO$_2$R$^a$, (C=O)R$^a$ or CO$_2$R$^a$;

R$^2$, R$^3$ and R$^4$ are independently H, OH, CHO, CN, halogen, (C=O)$_r$O$_s$(C$_1$-C$_{10}$)alkyl, (C=O)$_r$O$_s$(C$_2$-C$_{10}$)alkenyl, (C=O)$_r$O$_s$(C$_2$-C$_{10}$)alkynyl, (C=O)$_r$O$_s$cycloalkyl, (C=O)$_r$O$_s$cycloalkenyl, (C=O)$_r$O$_s$cycloalkynyl, (C=O)$_r$O$_s$heterocycyl, (C=O)$_r$O$_s$aryl, (C=O)$_r$O$_s$heteroaryl, (C=O)$_r$O$_s$perfluoroalkyl or (C$_0$-C$_6$)alkyl-NR$^b$R$^c$, wherein said alkykl, alkenyl, alkynyl, cycyloalkyl, cycloalkenyl, cycloalkynyl, heterocycyl, aryl, heteroaryl and perfluoroalkyl is optionally substituted with one or more substituents selected from R$^6$;

R$^5$ is H, aryl or (C$_1$-C$_6$)alkyl;

R$^6$ is (C=O)$_r$O$_s$NR$^a$R$^b$, (C=O)$_r$O$_s$aryl, (C=O)$_r$O$_s$heterocycyl, halogen, OH, oxo, (C=O)$_r$O$_s$(C$_1$-C$_3$)perfluoroalkyl, (C=O)$_r$O$_s$(C$_1$-C$_6$)alkyl, CHO, CO$_2$H, CN, (C$_0$-C$_6$)alkyl-NR$^b$R$^c$ or (C$_1$-C$_6$)alkyl-heterocycyl;

R$^a$ is (C$_1$-C$_6$)alkyl, aryl or heterocycyl; and

R$^b$ and R$^c$ independently are H, (C=O)$_r$O$_s$(C$_1$-C$_{10}$)alkyl, SO$_2$R$^a$, (C=O)$_r$O$_s$heterocycyl, (C=O)$_r$O$_s$aryl, (C=O)$_r$O$_s$heteroaryl or CO$_2$R$^a$, wherein r and s independently are 0 or 1 and said alkyl, heterocycyl, aryl or heteroaryl is optionally substituted with one or more substituents selected from R$^6$.

In another embodiment, R$^1$ is H.

In another embodiment, R$^2$ is H and R$^3$ is (C$_0$-C$_6$)alkyl-NR$^b$R$^c$.

In another embodiment, R$^4$ is heteroaryl.

In another embodiment, said pharmacophore containing compound, comprises a compound of Figure III or a pharmaceutically acceptable salt thereof:

Figure III

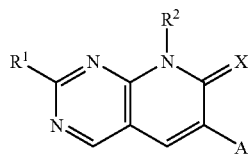

A is aryl or heteroaryl, wherein said aryl or heteroaryl is optionally substituted with one or more substituents selected from R$^3$;

X is NH, N-acyl, O or S;

R$^1$ and R$^2$ are independently H, OH, CHO, CN, halogen, (C=O)$_r$O$_s$(C$_1$-C$_{10}$)alkyl, (C=O)$_r$O$_s$(C$_2$-C$_{10}$)alkenyl, (C=O)$_r$O$_s$(C$_2$-C$_{10}$)alkynyl, (C=O)$_r$O$_s$cycloalkyl, (C=O)$_r$O$_s$cycloalkenyl, (C=O)$_r$O$_s$cycloalkynyl, (C=O)$_r$O$_s$heterocycyl, (C=O)$_r$O$_s$aryl, (C=O)$_r$O$_s$heteroaryl, (C=O)$_r$O$_s$perfluoroalkyl or (C$_0$-C$_6$)alkyl-NR$^a$R$^b$, wherein said alkykl, alkenyl, alkynyl, cycyloalkyl, cycloalkenyl, cycloalkynyl, heterocycyl, aryl, heteroaryl and perfluoroalkyl is optionally substituted with one or more substituents selected from R$^3$;

R$^3$ is (C=O)$_r$O$_s$NR$^a$R$^b$, (C=O)$_r$O$_s$aryl, (C=O)$_r$O$_s$heterocycyl, halogen, OH, oxo, (C=O)$_r$O$_s$(C$_1$-C$_3$)perfluoroalkyl, (C=O)$_r$O$_s$S$_t$(C$_1$-C$_6$)alkyl, CHO, CO$_2$H, CN, (C$_0$-C$_6$)alkyl-NR$^a$R$^b$ or (C$_1$-C$_6$)alkyl-heterocycyl;

R$^a$ and R$^b$ independently are H, (C=O)$_r$O$_s$(C$_1$-C$_{10}$)alkyl, SO$_2$R$^1$, (C=O)$_r$O$_s$heterocycyl, (C=O)$_r$O$_s$aryl, (C=O)$_r$O$_s$heteroaryl or CO$_2$R$^1$, wherein r, s and t independently are 0 or 1 and said alkyl, heterocycyl, aryl or heteroaryl is optionally substituted with one or more substituents selected from R$^3$.

In another embodiment, A is aryl.

In another embodiment, aryl is 2,5-dichlorophenyl.

In another embodiment, R$^1$ is (C$_0$-C$_6$)alkyl-NR$^a$R$^b$ and R$^2$ is (C=O)$_r$O$_s$(C$_1$-C$_{10}$)alkyl.

In another embodiment, (C=O)$_r$O$_s$(C$_1$-C$_{10}$)alkyl is methyl.

In another embodiment, (C$_0$-C$_6$)alkyl-NR$^a$R$^b$ is

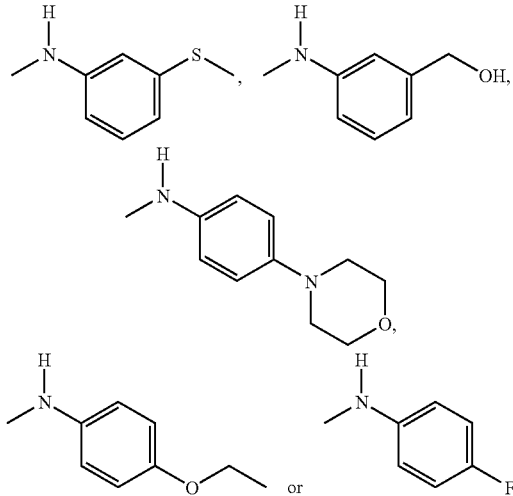

or a pharmaceutically acceptable salt thereof.

In another embodiment, the agent is administered orally.

In one embodiment, the compound is administered with a NSAID. In another embodiment, the NSAID is sulindac sulfide, flufenamic acid, ibuprofen, flurbiprofen, fenoprofen, mefenamic acid, indomethacin, carprofen, meclofenamic acid.

In one embodiment, the compound is administered with an antioxidant. In a specific embodiment, the antioxidant is selected from the group consisting of vitamin E, vitamin C, curcumin, and Gingko biloba.

In another embodiment, the compound is administered with an acetylcholinesterase inhibitor.

3.1. Terminology

As used herein, enzymatic activity of an enzyme, e.g., γ-secretase, is "ATP-dependent" if (i) the activation state (level of activity) of the enzyme is modulated by the binding of ATP to the enzyme; (ii) the activity of the enzyme is modulated by the binding of ATP to a molecule in an enzyme complex that contains the enzyme; (iii) the activity of the enzyme is modulated by the binding of ATP to a molecule that effects the assembly, localization or stability of the enzyme complex; or (iv) the activity of the enzyme is modulated by the binding of ATP to a molecule that affects the activation state (level of activity) of the enzyme complex.

As used herein, the terms "modulate," "modulates," "modulated" or "modulation" shall have their usual meanings, and encompass the meanings of the words "enhance," "promote," "increase," "agonize," "inhibit," "decrease" or "antagonize."

As used herein, an "agonist" is any compound that acts directly or indirectly on a molecule to produce a pharmacological effect, while an "antagonist" is any compound that blocks the stimulation of a pharmacological effect.

As used herein, a "sufficient amount" of a compound, or "an amount of a compound sufficient to . . . " refers to an amount that contains at least the minimum amount necessary to achieve the intended result. Such an amount can routinely be determined by one of skill in the art based on data from studies using methods of analysis such as those disclosed herein. Such data may include, but not be limited to, results from IC50 determinations, as discussed hereinbelow.

As used herein, the term "Aβ-related disorder" or an "Aβ disorder" is a disease (e.g., Alzheimer's disease) or a condition (e.g., senile dementia) that involves an aberration or dysregulation of Aβ levels. An Aβ-related disorder includes, but is not limited to Alzheimer's disease, Down's syndrome and inclusion body myositis.

As used herein, the terms "disorder" and "disease" are used interchangeably to refer to a condition in a subject.

As used herein, a "small organic molecule" is an organic compound (or organic compound complexed with an inorganic compound (e.g., metal)) that generally has a molecular weight of less than about 3 kilodaltons, preferably less than about 1.5 kilodaltons. Preferably, the small organic molecule can be orally administered and/or cross the blood-brain barrier.

As used herein, the term "about" means within 10 to 15%, preferably within 5 to 10%.

As used herein, the term "ATP modulator," refers to a compound that modulates ATP function in a cell. For example, an ATP modulator can be a compound that binds to a molecule normally affected by ATP binding and, by binding to the molecule, modulates, e.g., inhibits, ATP's usual effect on the molecule. Such an ATP modulator can bind the molecule at an ATP-binding site on the molecule or at some other site on the molecule. The ATP modulator can act by competing with ATP for binding to the molecule, e.g., by competing for binding to an ATP-binding site. Preferably the ATP modulator is a selective ATP modulator.

As used herein, the terms "selective ATP modulator" or "selective ATP modulation" refers to a modulator (or modulation) that discriminates among the molecules that affect ATP function in the cell and only modulates a specific individual molecule, or class or subset of the molecules (a "modulatory profile"). For example, a compound may be assayed for activity in inhibiting a collection of various kinases, and is recognized as a selective ATP modulator if it modulates ATP function in a related class of kinases. In one embodiment, a selective ATP modulator is one that exhibits a modulatory profile/identical to or substantially similar to that exhibited by STI-571, a mesylate salt of STI-571, Compound 1 or Compound 2.

As used herein, the terms "treat", "treatment" and "treating" refer to the amelioration of a Aβ-related disorder that results from the administration of one or more compounds that lower Aβ levels exhibited by a cell or tissue. It also refers to the managing of the disorder, or the slowing and/or reversing of the progression of the disorder.

Symptoms of Aβ-related disorders are well known to those of skill in the art. For example, symptoms of Alzheimer's disease are well known in the art and can include, e.g., memory loss, mild cognitive impairment, cognitive decline, severe cognitive impairment and personality changes that result in loss of functional ability, e.g., over the course of a decade. In debilitated states, patients usually exhibit severe impairment, and retain only vegetative neurologic function. Symptoms of Alzheimer's disease can also include certain art-known neuropathological lesions, including intracellular neurofibrillary tangles and extracellular parenchymal and cerebrovascular amyloid.

As used herein, the terms "manage," "managing" and "management" refer to the beneficial effects that a subject derives from a compound, such as a compound that lowers Aβ levels exhibited by a cell or tissue, which does not result in a cure of the disease. In certain embodiments, a subject is administered one or more such agents to "manage" a disorder so as to prevent or slow the progression or worsening of the disorder.

As used herein, the terms "prevent", "preventing" and "prevention" refer to the impedition of the recurrence or onset of an Aβ-related disorder or one or more symptoms of a Aβ-related disorder in a subject.

A used herein, a "protocol" includes dosing schedules and dosing regimens. The protocols herein are methods of use and include prophylactic and therapeutic protocols.

As used herein, the terms "subject" and "patient" are used interchangeably. As used herein, the terms "subject" and "subjects" refer to an animal, preferably a mammal including a non-primate (e.g., a cow, pig, horse, donkey, goat, camel, cat, dog, guinea pig, rat, mouse, sheep) and a primate (e.g., a monkey, such as a cynomolgous monkey, gorilla, chimpanzee, and a human), preferably a human. In one embodiment, the subject is a subject with Alzheimer's disease.

The term "pharmaceutically acceptable" as used herein means a composition, e.g., a carrier, excipient, or salt, approved by a regulatory agency of the Federal or a state government or listed in the U.S. Pharmacopoeia or other generally recognized pharmacopoeia for use in animals, and more particularly, in humans.

4. DESCRIPTION OF THE FIGURES

Figure 6:
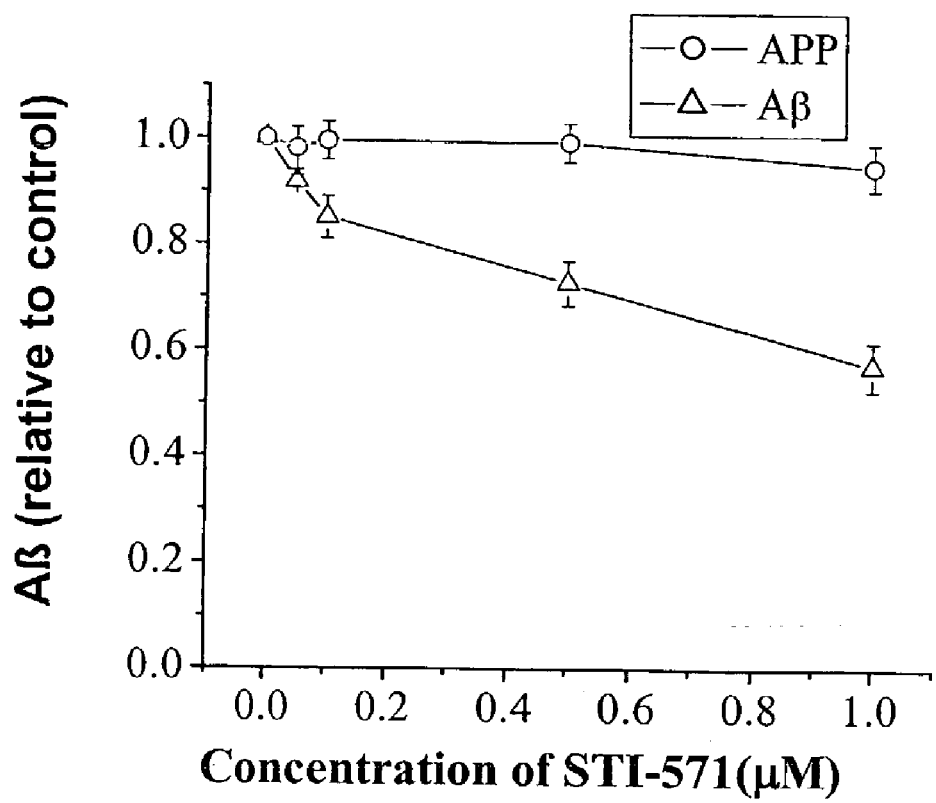

FIG. 6 is a graph of the dose-dependent inhibition by the mesylate salt of STI-571 (imatinib mesylate, GLEEVEC™, Novartis Pharmaceuticals; Calbiochem) of Aβ formation by intact N2a cells expressing the Swedish variant of human APP. The graph also demonstrates that APP levels do not change in response to STI-571 administration.

Figure 7:
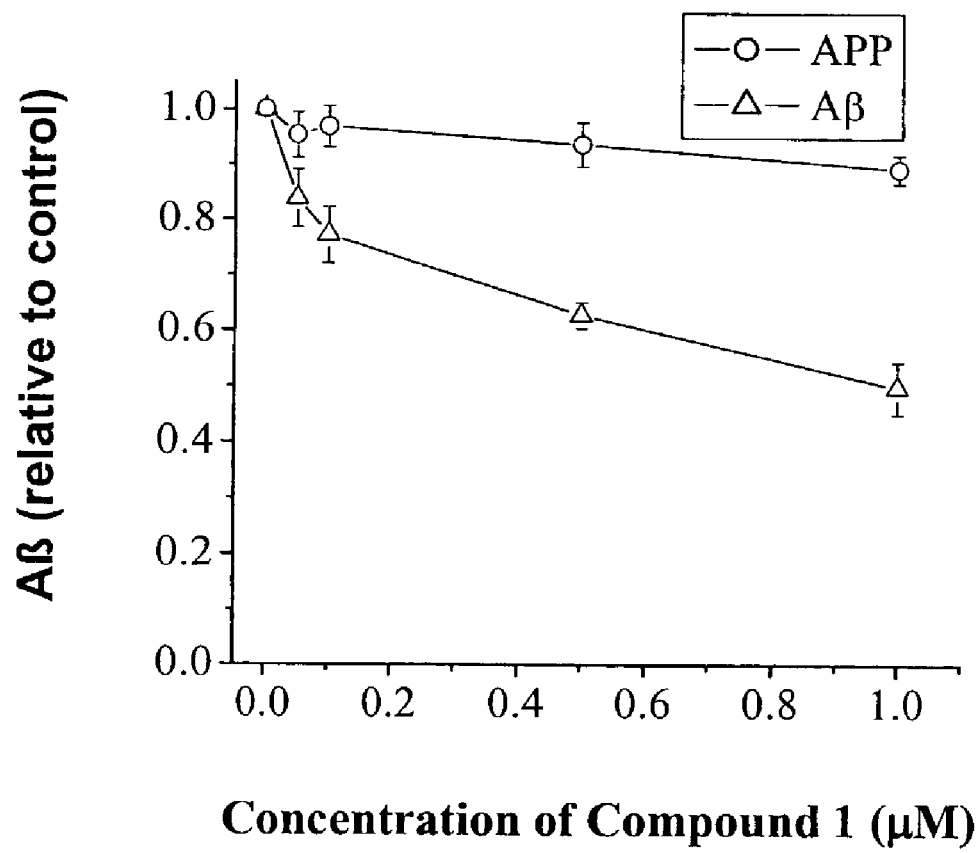

FIG. 7 is a graph of the dose-dependent inhibition by Compound 1 of Aβ formation in intact N2a cells expressing the Swedish variant of human APP. The graph also demonstrates that APP levels do not change in response to STI-571 administration.

Figure 8A:
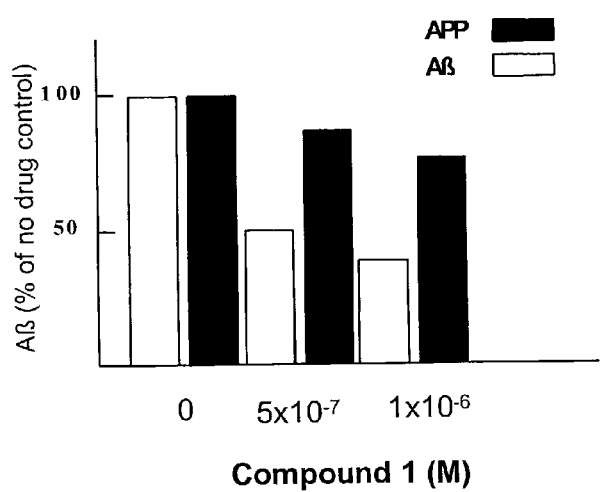
Figure 8B:
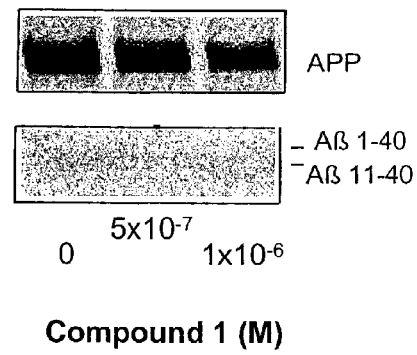

FIGS. 8A-B. FIG. 8A is a bar graph showing the reduction of Aβ produced from primary neuronal cells cultured from rat brain in response to Compound 1. FIG. 8B is an autoradiogram showing the amount of APP produced (top panel) and the amount of Aβ produced at different concentrations of Compound 1 (bottom panel).

Figure 9:
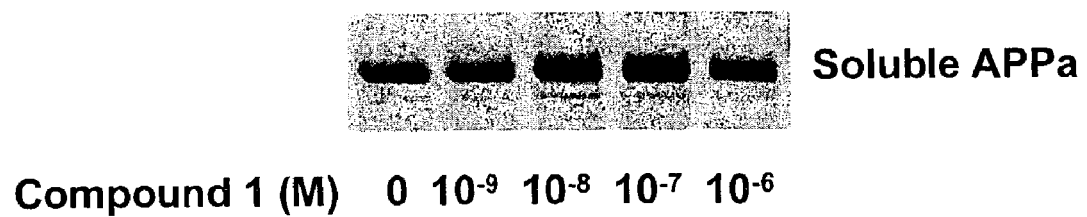

FIG. 9 is an autoradiogram illustrating consistent secretion of soluble APP-α ("APPa") from primary neuronal cells cultured from rat brain in the presence of Compound 1.

Figure 10:
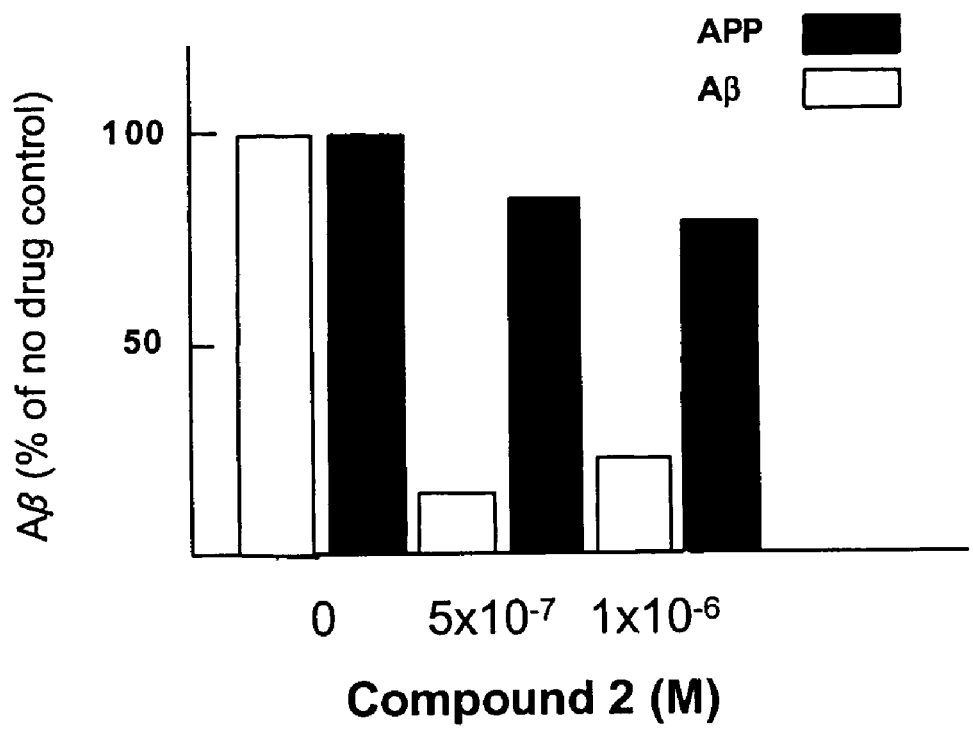

FIG. 10 is a bar graph showing the reduction of Aβ produced from primary neuronal cells cultured from rat brain in response to the presence of Compound 2.

Figure 11:
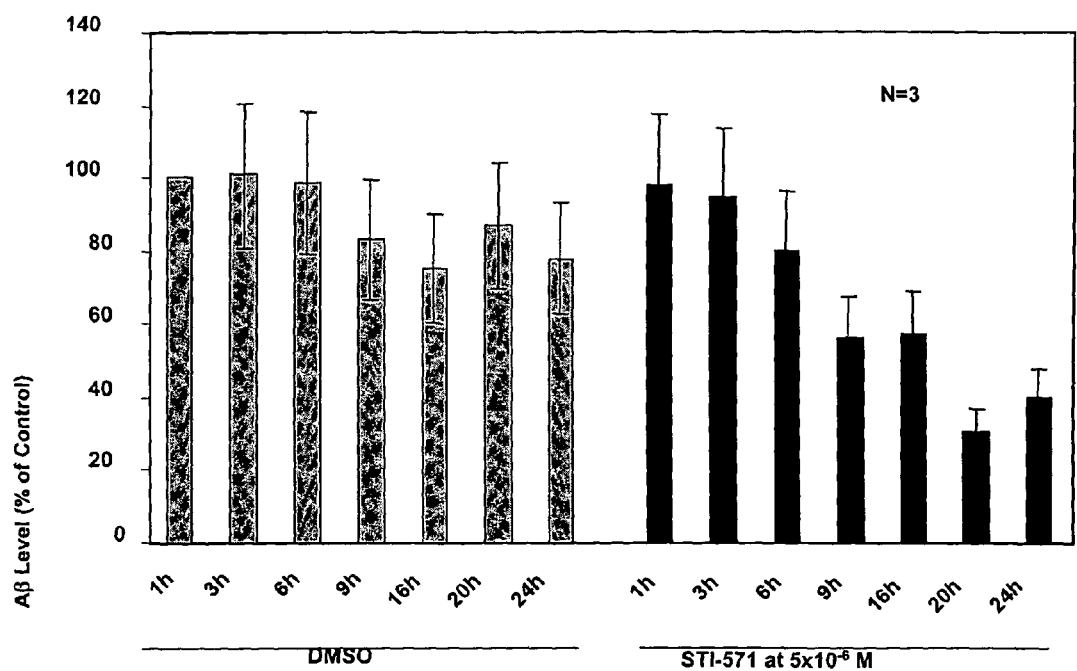

FIG. 11 is a bar graph showing the time course (in hours) of the effect of STI-571 (mesylate salt) on Aβ generation from primary neuronal cells cultured from rat brain.

Figure 12:
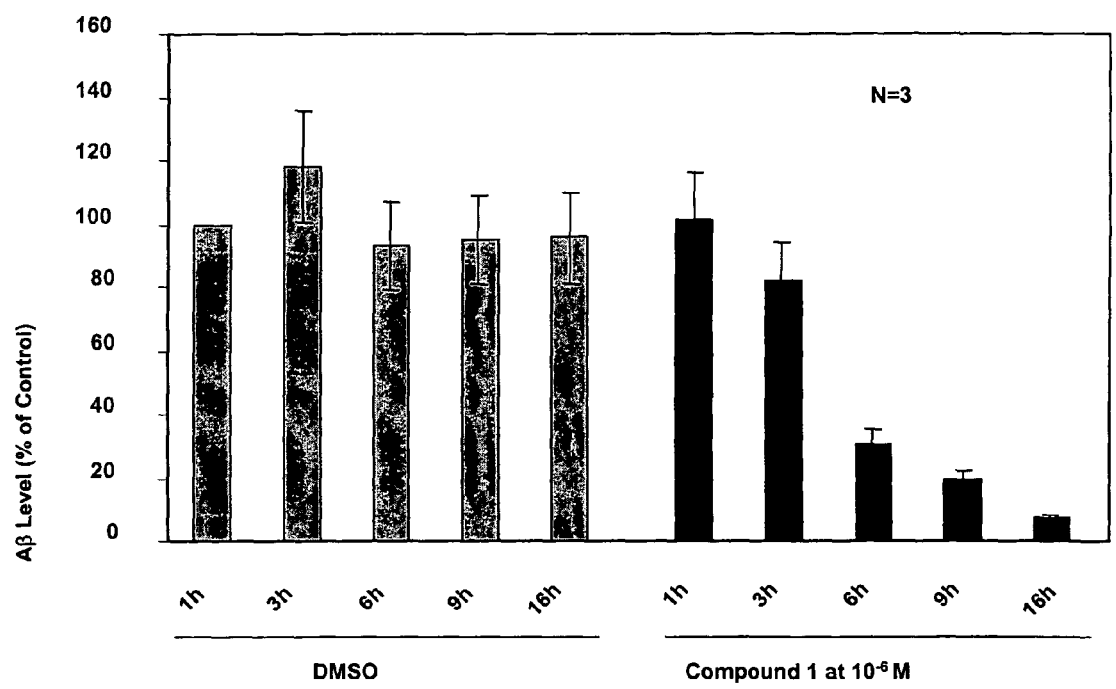

FIG. 12 is a bar graph showing the time course of Compound 1 effect on Aβ generation from primary neuronal cells cultured from rat brain.

Figure 13:
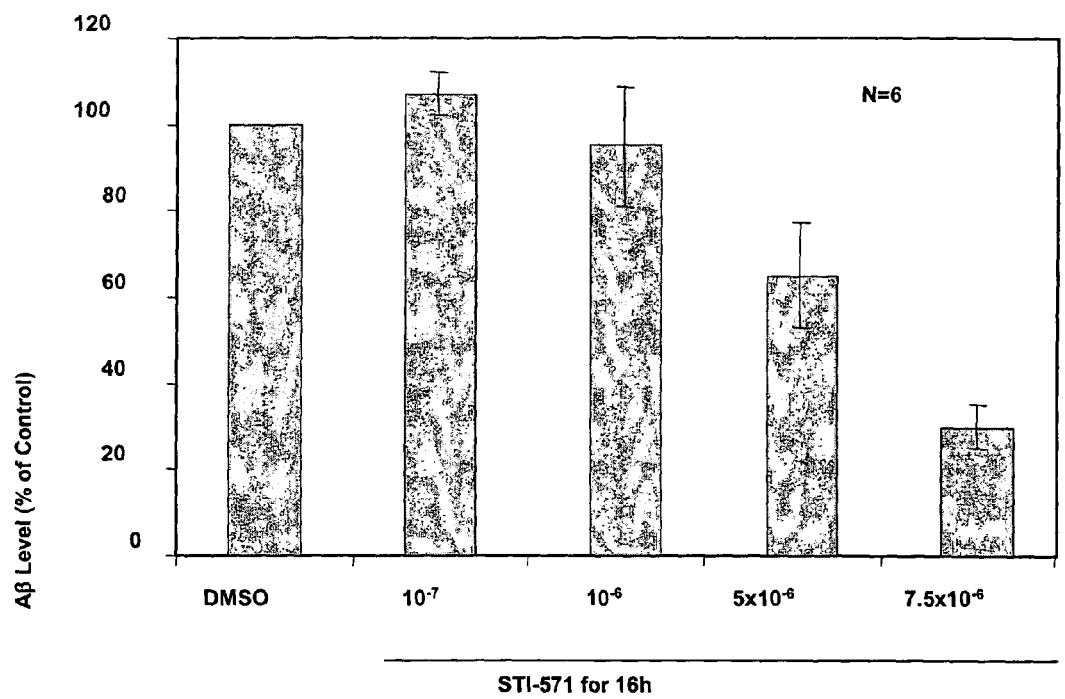

FIG. 13 is a bar graph showing the dose response to STI-571 on Aβ generation from primary neuronal cells cultured from rat brain.

Figure 14:
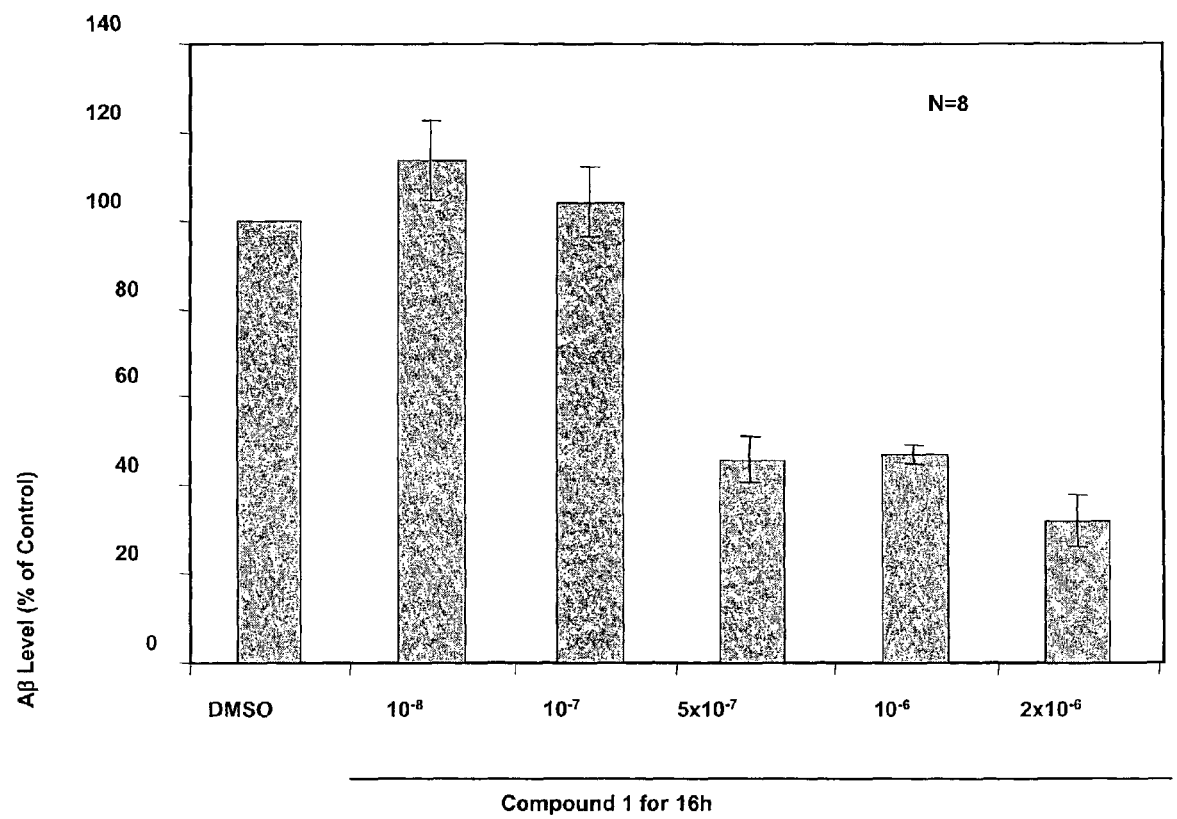

FIG. 14 is a bar graph showing the dose response to Compound 1 on Aβ generation from primary neuronal cells cultured from rat brain. X-axis, DMSO control and Compound 1 concentration (M).

Figure 15A:
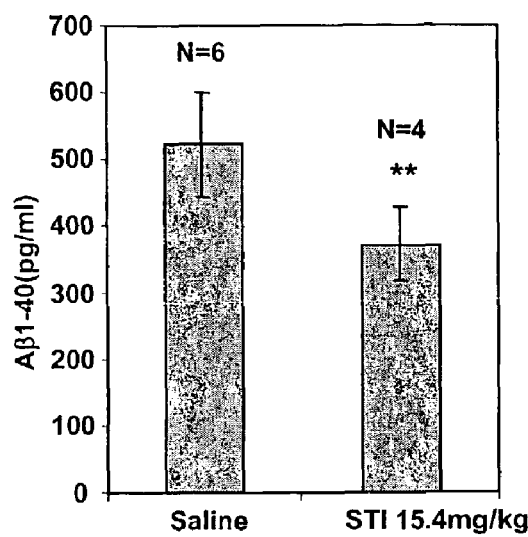
Figure 15B:
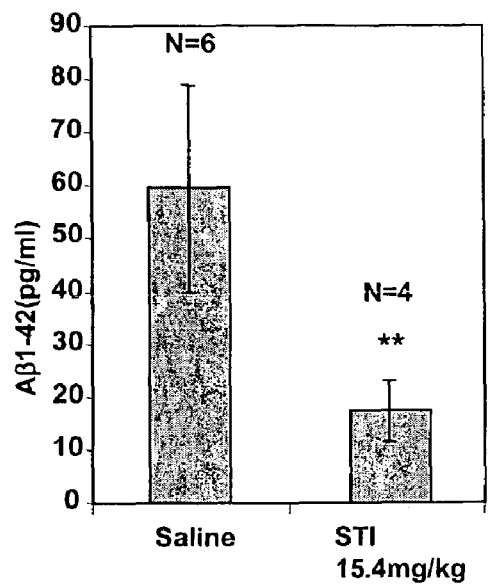
Figure 15C:
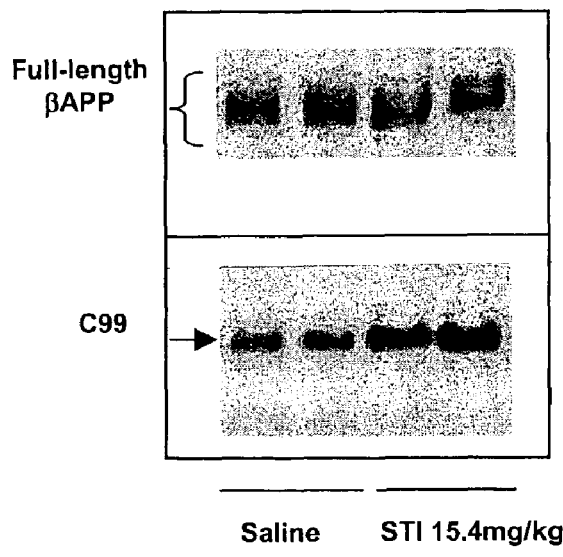
Figure 15D:
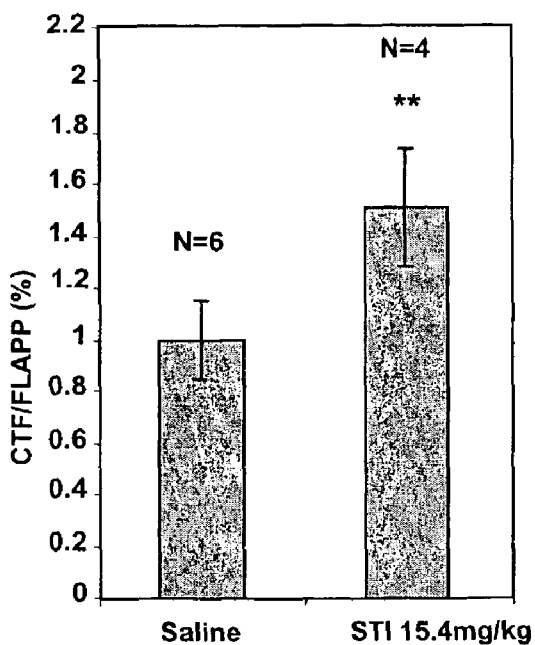

FIGS. 15A-D show the quantitation of STI-571 mesylate salt ("STI")-dependent decreases in Aβ1-40(15A), Aβ 1-42 (15B) and increases in C99 (15C and 15D), in vivo in guinea pig. FIG. 15C also demonstrates that full-length βAPP levels do not change in response to treatment. **, p<0.01; *, 0.01<p<0.05.

Figure 16A:
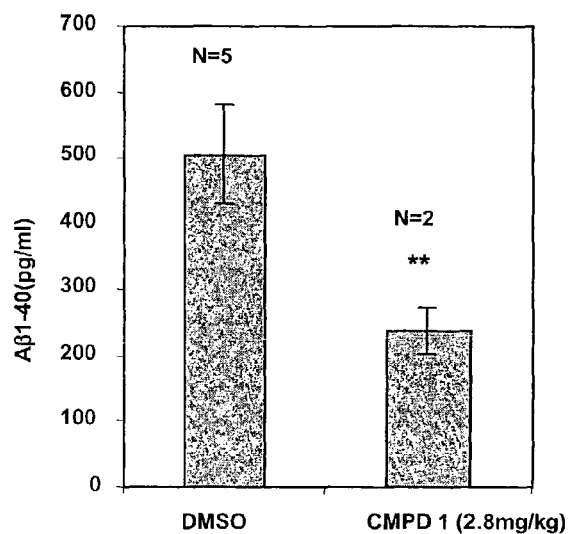
Figure 16B:
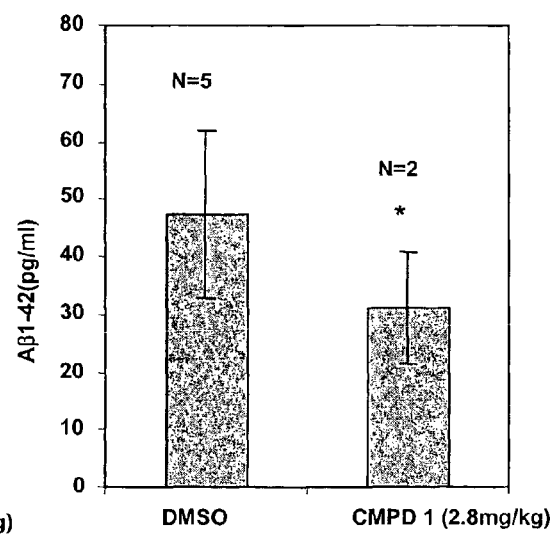
Figure 16C:
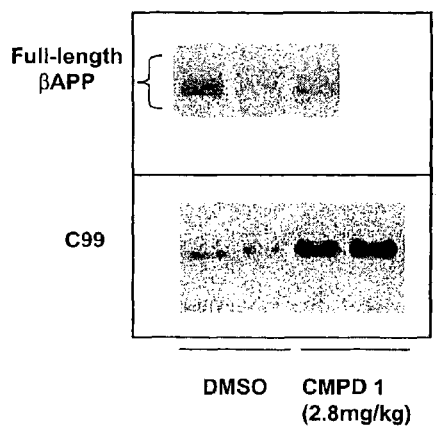
Figure 16D:
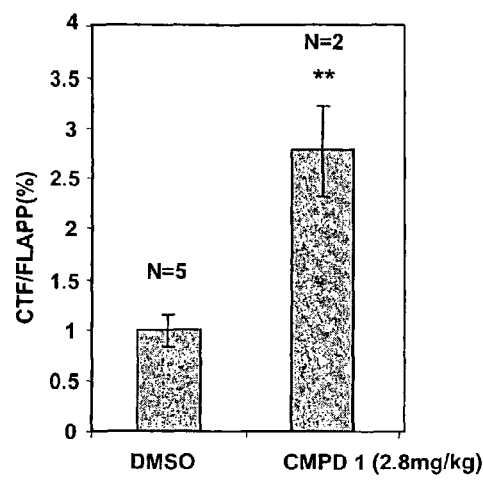

FIGS. 16A-D show the quantitation of Compound 1 ("CMPD 1")-dependent decreases in A1-40(16A), Aβ1-42 (16B) and increases in C99 (16C and 16D), in vivo in guinea pig. FIG. 16C also demonstrates that full-length βAPP levels do not change in response to treatment.*, p<0.01; *, 0.01<p<0.05.

Figure 17:
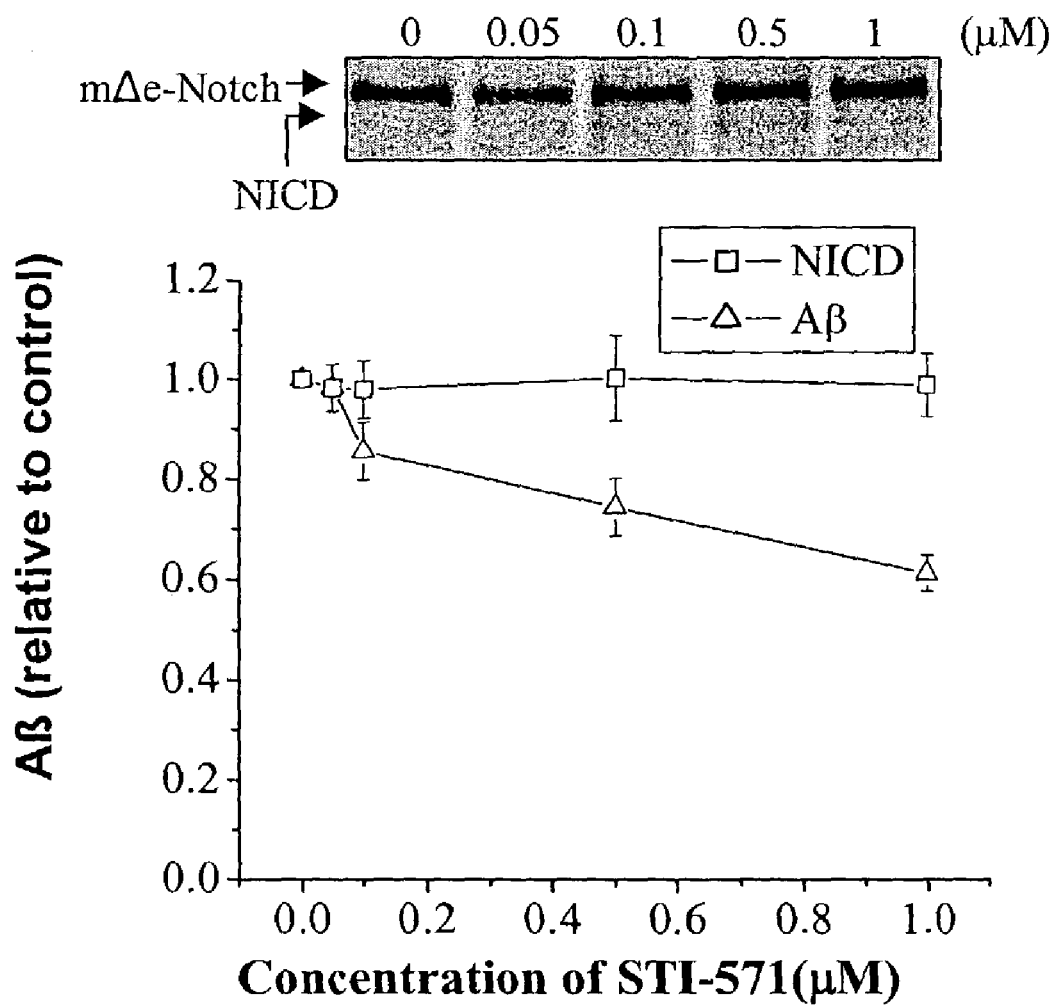

FIG. 17 is a graph and an autoradiogram showing stable levels of Notch cleavage in intact cells treated with STI-571 (mesylate salt). The figure presents results demonstrating that while STI-571 administration reduces Aβ levels in a dose-dependent manner, the level of Notch and Notch cleavage product (Notch intracellular domain, NICD) remains stable.

Figure 18:
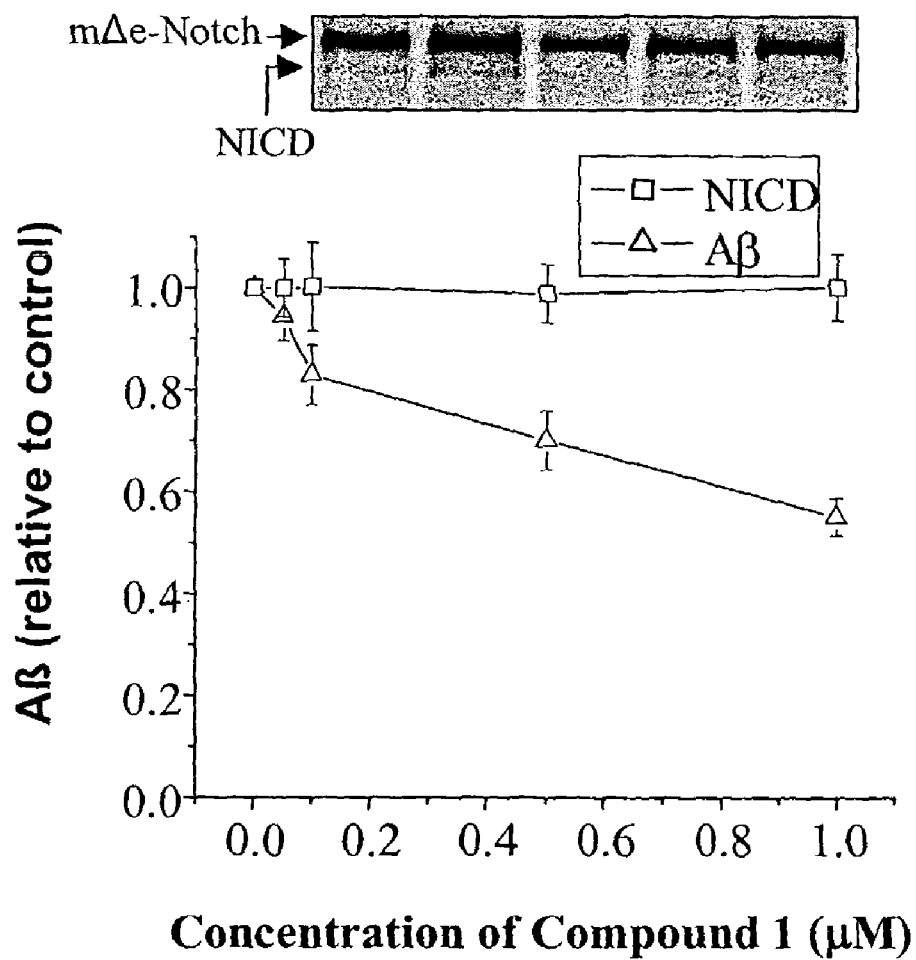

FIG. 18 is a graph showing stable levels of Notch cleavage in intact cells treated with Compound 1.

Figure 19:
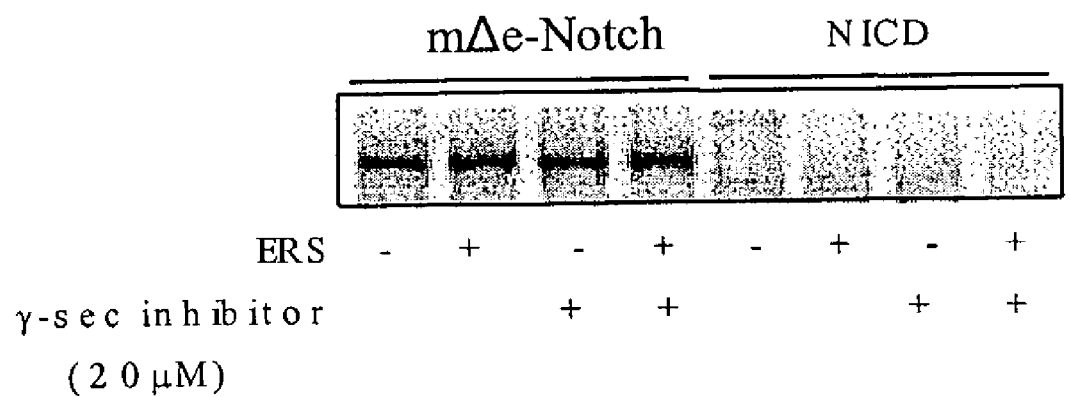

FIG. 19 is an autoradiogram illustrating that a standard γ-secretase inhibitor ("γ-secretase inhibitor"; Calbiochem) inhibits Notch cleavage in a cell-free system derived from mΔe-Notch 1 transfected N2a cells, and that γ-secretase activity is therefore necessary for Notch cleavage in this system. The transfected cells were permeabilized and incubated either with or without a standard ATP energy regenerating system with GTP, and either in the presence or absence of a standard γ-secretase inhibitor ("γ-secretase inhibitor," Calbiochem). γ-sec, γ-secretase. ERS, energy regenerating system. NICD, Notch intracellular domain.

Figure 20:
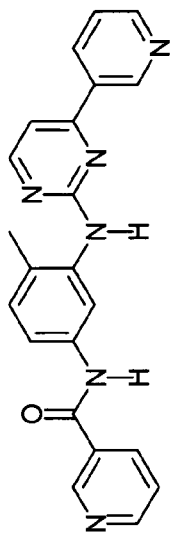
Figure 20:
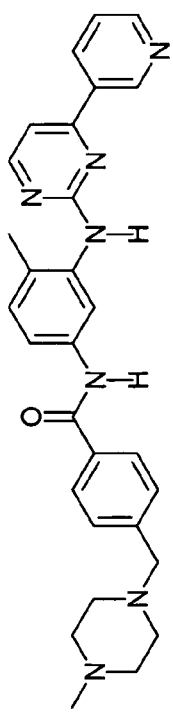
Figure 20:
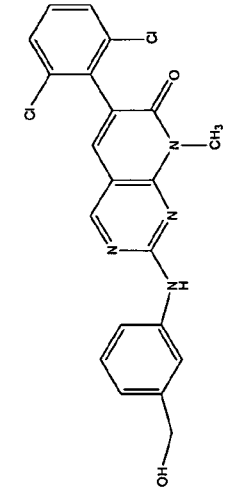
Figure 20:
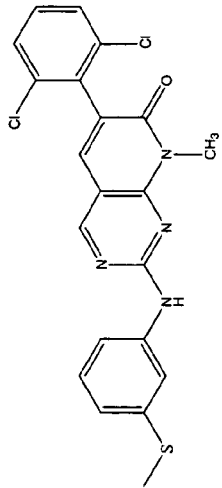

FIG. 20 is a diagram of the chemical structures of ST-571 (known in its mesylate salt form as the active ingredient in GLEEVECT™ capsules), STI-571 variant ("WGB-BC-15"), Compound 1 (PD173955, Moasser et al., 1999, Cancer Research 59: 6145-6152; Wisniewski et al., 2002, Cancer Research 62(15):4244-55), and Compound 2 (PD166326; Wisniewski et al., 2002, Cancer Research 62(15):4244-55).

5. DETAILED DESCRIPTION OF THE INVENTION

For clarity of disclosure, and not by way of limitation, the detailed description of the invention is divided into the subsections set forth below.

5.1. Methods for Modulating Amyloid β Peptide (Aβ) Levels

The invention provides a method for modulating amyloid-β peptide (Aβ) levels exhibited by a cell or tissue comprising contacting said cell or tissue with an amount of a compound sufficient to modulate said Aβ levels, wherein said compound modulates an ATP-dependent enzymatic activity.

A cell or tissue may include, but not be limited to: an excitable cell, e.g., a sensory neuron, motomeuron, or interneuron; a glial cell; a primary culture of cells, e.g., a primary culture of neuronal or glial cells; cell(s) derived from a neuronal or glial cell line; dissociated cell(s); whole cell(s) or intact cell(s); permeabilized cell(s); a broken cell preparation; an isolated and/or purified cell preparation; a cellular extract or purified enzyme preparation; a tissue or organ, e.g., brain, brain structure, brain slice, spinal cord, spinal cord slice, central nervous system, peripheral nervous system, or nerve; tissue slices, and a whole animal. In certain embodiments, the brain structure is cerebral cortex, the hippocampus, or their anatomical and/or functional counterparts in other mammalian species. In certain embodiments, the cell or tissue is an N2a cell, a primary neuronal culture or a hippocampal tissue explant.

In one embodiment, the Aβ levels are lowered. In another embodiment, the Aβ levels are raised. In another embodiment, the Aβ is Aβ40. In another embodiment, the Aβ is Aβ42.

In another embodiment, the modulating results in an increase in the ratio of Aβ40 to Aβ42. In another embodiment, the modulating results in an increase in C99.

In another embodiment, the compound binds an enzyme that exhibits an ATP-dependent enzymatic activity. In another embodiment, the compound binds a molecule that regulates the ATP-enzymatic activity.

In another embodiment, the molecule is a molecule that is allosterically regulated by ATP.

In another embodiment, the compound is an ATP modulator. In another embodiment, the ATP modulator is a selective modulator.

In another embodiment, the ATP modulator competes with ATP for binding to an ATP-binding site. In another embodiment, the ATP-binding site is present on an enzyme that exhibits an ATP-dependent enzymatic activity. In another embodiment, the ATP-binding site is present on a molecule that regulates the ATP-dependent enzymatic activity.

Binding may be measured under any standard art-known physiological conditions, according to methods well known in the art.

In another embodiment, the compound does not affect total cellular levels of β-amyloid precursor product (APP). In another embodiment, the compound does not decrease levels of secreted APP (sAPP). In another embodiment, the compound increases levels of sAPPα. In another embodiment, levels of secreted Aβ are modulated. In another embodiment, the compound does not inhibit Notch-1 cleavage. In another embodiment, the compound does not affect tau phosphorylation.

In another embodiment, the compound crosses the blood-brain barrier.

In another embodiment, the enzymatic activity is a γ-secretase activity. In another embodiment, the compound inhibits γ-secretase activity. In another embodiment, the compound is an ATP modulator. In another embodiment, the ATP modulator is a selective modulator.

In another embodiment, the compound binds a γ-secretase enzyme exhibiting an ATP-dependent enzymatic activity. In another embodiment, the ATP modulator competes with ATP for binding to an ATP binding site.

In another embodiment, the compound is STI-571 or a blood-brain barrier permeable variant thereof, or a pharmaceutically acceptable salt thereof. In another embodiment, the compound is a mesylate salt of STI-571. In another embodiment, the compound is WGB-BC-15 or a blood-brain barrier permeable variant thereof, or a pharmaceutically acceptable salt thereof. In another embodiment, the compound is Compound 1 or a blood-brain barrier permeable variant thereof, or a pharmaceutically acceptable salt thereof. In another embodiment, the compound is Compound 2 or a blood-brain barrier permeable variant thereof, or a pharmaceutically acceptable salt thereof. In another embodiment, the compound is Compound 3 (PD173956; Bauer et al., 2001, Thromb. Haemost. 85(2):331-40, Maschberger et al., 2000, J. Biol. Chem. 275(25):19159-66) or a blood-brain barrier permeable variant thereof, or a pharmaceutically acceptable salt thereof. In another embodiment, the compound is Compound 4 (PD173952; Dorsey et al., 2002, Leukemia 16(9):1589-95) or a blood-brain barrier permeable variant thereof, or a pharmaceutically acceptable salt thereof. In another embodiment, the compound is Compound 5 (PD173958; Dorsey et al., 2002, Leukemia 16(9):1589-95; Joseloffet et al., 2002, J. Biol. Chem. 277(14):12318-23) or a blood-brain barrier permeable variant thereof, or a pharmaceutically acceptable salt thereof.

In another embodiment, the enzymatic activity is a kinase activity. In another embodiment, the compound binds to a kinase enzyme exhibiting an ATP-dependent enzymatic activity. In another embodiment, the compound competes with ATP for binding to an ATP-binding site on the kinase. In another embodiment, the compound binds to a site other than an ATP-binding site on the kinase. In another embodiment, the kinase is a tyrosine kinase. In another embodiment, the tyrosine kinase is Abl kinase, BCR-Abl kinase, ARG kinase, src kinase, c-kit or platelet-derived growth factor receptor. In another embodiment, the kinase is a scrine/threonine kinase, a carbohydrate kinase or a lipid kinase.

In another aspect, the invention provides a method for modulating Aβ levels exhibited by a cell or tissue comprising contacting said cell or tissue with an amount of an ATP modulator sufficient to modulate said Aβ levels.

In one embodiment, the Aβ levels are lowered. In another embodiment, the Aβ levels are raised. In another embodiment, the Aβ is A 40. In another embodiment, the Aβ is Aβ42.

In another embodiment, the modulating results in an increase in the ratio of Aβ40 to Aβ42. In another embodiment, the modulating results in an increase in C99. In another embodiment, the ATP modulator competes with ATP for binding to an ATP-binding site.

In another embodiment, the ATP-binding site is present on an enzyme that exhibits an ATP-dependent enzymatic activity. In another embodiment, the ATP-binding site is present on a molecule that regulates the ATP-dependent enzymatic activity. In another embodiment, the compound does not affect total cellular levels of β-amyloid precursor product (APP). In another embodiment, the compound does not decrease levels of secreted APP (sAPP). In another embodiment, the compound increases levels of sAPPα.

In another embodiment, levels of secreted Aβ are modulated.

In another embodiment, the compound does not inhibit Notch-1 cleavage. In another embodiment, the compound does not affect tau phosphorylation. In another embodiment, the compound crosses the blood-brain barrier. In another embodiment, the enzymatic activity is a γ-secretase activity. In another embodiment, the compound inhibits γ-secretase activity.

In another embodiment, the compound is an ATP modulator. In another embodiment, the ATP modulator is a selective modulator. In another embodiment, the compound binds a γ-secretase enzyme exhibiting an ATP-dependent enzymatic activity.

In another embodiment, the compound is STI-571 or a blood-brain barrier permeable variant thereof, or a pharmaceutically acceptable salt thereof. In another embodiment, the compound is a mesylate salt of STI-571. In another embodiment, the compound is WGB-BC-15 or a blood-brain barrier permeable variant thereof, or a pharmaceutically acceptable salt thereof. In another embodiment, the compound is any of Compounds 1-5 or a blood-brain barrier permeable variant thereof, or a pharmaceutically acceptable salt thereof.

In another embodiment, the enzymatic activity is a kinase activity. In another embodiment, the compound binds to a kinase enzyme exhibiting an ATP-dependent enzymatic activity. In another embodiment, the compound competes with ATP for binding to an ATP-binding site on the kinase. In another embodiment, the compound binds to a site other than an ATP-binding site on the kinase. In another embodiment, the kinase is a tyrosine kinase. In another embodiment, the tyrosine kinase is Abl kinase, BCR-Abl kinase, ARG kinase, src kinase, c-kit or platelet-derived growth factor receptor. In another embodiment, the kinase is a serine/threonine kinase, a carbohydrate kinase or a lipid kinase. In another embodiment, the kinase is a serine/threonine kinase, a carbohydrate kinase or a lipid kinase.

In another embodiment, the compound competes with ATP for binding to a target other than γ-secretase in the metabolic pathway that regulates the cleavage of APP to Aβ by γ-secretase. In specific embodiments, the target is a kinase (or kinase domain), a protease (e.g., an AAA protease of the kind localized to the inner mitochondrial membrane), a phosphatase, or a molecular chaperone molecule (e.g., hsp 60, hsp70, hsp90).

In certain embodiments, γ-secretase activity may reflect assembly, allosteric activation, or stabilization of a protein complex. In certain embodiments, the level of γ-secretase activity is a level of this protein complex, and the level of the protein complex can be determined by measuring the levels of the component proteins in the complex by methods well known in the art, e.g., by immunoblotting.

In another embodiment, the compound inhibits γ-secretase activity either by binding to a site on γ-secretase, or on a component protein of γ-secretase (as in a γ-secretase multi-molecular complex that cam comprise presenilin, nicastrin and APH1), that otherwise can be occupied by ATP (where ATP-binding is necessary for kinase activity or for accelerating γ-secretase activity). According to the invention, such compounds antagonize ATP. Alternatively, in certain embodiments, these compounds may bind to a modulator of γ-secretase activity at an ATP binding site, wherein said modulator is a factor that is necessary for assembly, stability, trafficking or activation of γ-secretase activity and is antagonized by binding of the compound.

In other embodiments, the level of Aβ is modulated via modulation of γ-secretase activity.

In one aspect, the invention provides a method for modulating Aβ levels in a cell or tissue comprising contacting said cell or tissue with an amount of a compound sufficient to modulate said Aβ levels, wherein said compound contains the following pharmacophore:

wherein X is CH—, O, NH or N—CO—.

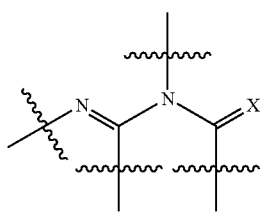

In one embodiment, said pharmacophore containing compound comprises a compound of Figure I or a pharmaceutically acceptable salt thereof:

Figure I

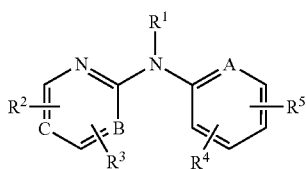

A is CH or N;
B and C are independently CH, N or N$^+$—O—;
$R^1$ is H, $SO_2R^a$, $(C=O)_rO_sR^a$;
$R^2$, $R^3$, $R^4$ and $R^5$ are independently H, OH, CHO, CN, halogen, $(C=O)_rO_s(C_1-C_{10})$alkyl, $(C=O)_rO_s(C_2-C_{10})$alkenyl, $(C=O)_rO_s(C_2-C_{10})$alkynyl, $(C=O)_rO_s$cycloalkyl, $(C=O)_rO_s$cycloalkenyl, $(C=O)_rO_s$cycloalkynyl, $(C=O)_rO_s$heterocycyl, $(C=O)_rO_s$aryl, $(C=O)_rO_s$heteroaryl, $(C=O)_rO_s$perfluoroalkyl or $(C_0-C_6)$alkyl-$NR^bR^c$,
wherein said alkykl, alkenyl, alkynyl, cycyloalkyl, cycloalkenyl, cycloalkynyl, heterocycyl, aryl, heteroaryl and perfluoroalkyl is optionally substituted with one or more substituents selected from $R^6$;

$R^6$ is $(C=O)_rO_sNR^aR^b$, $(C=O)_rO_s$aryl, $(C=O)_rO_s$heterocycyl, halogen, OH, oxo, $(C=O)_rO_s(C_1-C_3)$perfluoroalkyl, $(C=O)_rO_s(C_1-C_6)$alkyl, CHO, $CO_2H$, CN, $(C_0-C_6)$alkyl-$NR^bR^c$ or $(C_1-C_6)$alkyl-heterocycyl,
wherein said alkyl-heterocycyl is optionally substituted with OH;

$R^a$ is $(C_1-C_6)$alkyl, aryl or heterocycyl; and $R^b$ and $R^c$ independently are H, $(C=O)_rO_s(C_1-C_{10})$alkyl, $SO_2R^a$, $(C=O)_rO_s$heterocycyl, $(C=O)_rO_s$aryl, $(C=O)_rO_s$heteroaryl or $CO_2R^a$,
wherein r and s independently are 0 or 1 and said alkyl, heterocycyl, aryl or heteroaryl is optionally substituted with one or more substituents selected from $R^6$.

In another embodiment, A is CH, B is N and C is CH.
In another embodiment, $R^1$ is H.
In another embodiment, $R^2$ is H and $R^3$ is heteroaryl.
In another embodiment, $R^4$ is $(C=O)_rO_s(C_1-C_{10})$alkyl and $R^5$ is $(C_0-C_6)$alkyl-$NR^bR^c$.

In another embodiment, $R^3$ is 3-pyridinyl.
In another embodiment, r is 0, s is 0 and $(C_1-C_{10})$alkyl is methyl.
In another embodiment, $(C_0-C_6)$alkyl is a direct bond $(C_0-C_6)$, $R^b$ is H and $R^c$ is $(C=O)_rO_s$heteroaryl or $(C=O)_rO_s$heterocycyl.

In another embodiment, $(C=O)_rO_s$heterocycyl is 4-hydroxy-1-piperazino, as illustrated below or a pharmaceutically acceptable salt thereof.

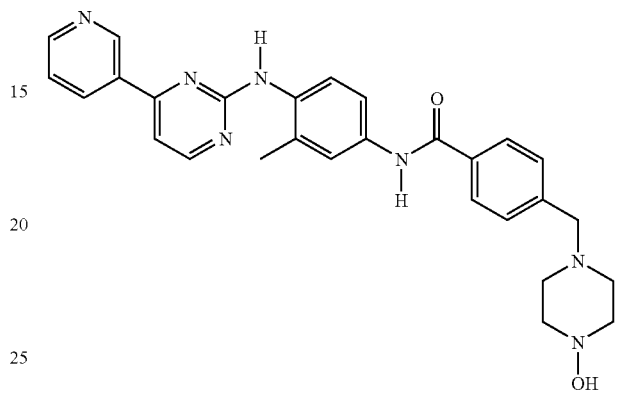

In another embodiment, $(C=O)_rO_s$heteroaryl is 3-pyrindinyl, as illustrated below or a pharmaceutically acceptable salt thereof.

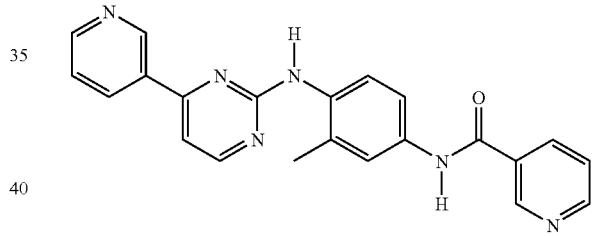

In another embodiment, said pharmacophore containing compound, comprises a compound of Figure II or a pharmaceutically acceptable salt thereof:

Figure II

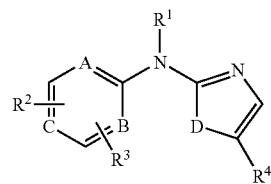

A, B and C are independently CH, N or N$^+$—O—;
D is O, S or N—$R^5$;
$R^1$ is H, $SO_2R^a$, $(C=O)_rR^a$ or $CO_2R^a$;
$R^2$, $R^3$ and $R^4$ are independently H, OH, CHO, CN, halogen, $(C=O)_rO_s(C_1-C_{10})$alkyl, $(C=O)_rO_s(C_2-C_{10})$alkenyl, $(C=O)_rO_s(C_2-C_{10})$alkynyl, $(C=O)_rO_s$cycloalkyl, $(C=O)_rO_s$cycloalkenyl, $(C=O)_rO_s$cycloalkynyl, $(C=O)_rO_s$heterocycyl, $(C=O)_rO_s$aryl, $(C=O)_rO_s$heteroaryl, $(C=O)_rO_s$perfluoroalkyl or $(C_0-C_6)$alkyl-$NR^bR^c$, wherein said alkykl, alkenyl, alkynyl, cycyloalkyl, cycloalkenyl, cycloalkynyl, heterocycyl, aryl, heteroaryl and perfluoroalkyl is optionally substituted with one or more substituents selected from $R^6$;

$R^5$ is H, aryl or $(C_1-C_6)$alkyl;

$R^6$ is $(C=O)_rO_sNR^aR^b$, $(C=O)_rO_s$aryl, $(C=O)_rO_s$heterocycyl, halogen, OH, oxo, $(C=O)_rO_s(C_1-C_3)$perfluoroalkyl, $(C=O)_rO_s(C_1-C_6)$alkyl, CHO, $CO_2H$, CN, $(C_0-C_6)$alkyl-$NR^bR^c$ or $(C_1-C_6)$alkyl-heterocycyl;

$R^a$ is $(C_1-C_6)$alkyl, aryl or heterocycyl; and $R^b$ and $R^c$ independently are H, $(C=O)_rO_s(C_1-C_{10})$alkyl, $SO_2R^a$, $(C=O)_rO_s$heterocycyl, $(C=O)_rO_s$aryl, $(C=O)_rO_s$heteroaryl or $CO_2R$, wherein r and s independently are 0 or 1 and said alkyl, heterocycyl, aryl or heteroaryl is optionally substituted with one or more substituents selected from $R^6$.

In another embodiment, $R^1$ is H.

In another embodiment, $R^2$ is H and $R^3$ is $(CO-C_6)$alkyl-$NR^bR^c$.

In another embodiment, $R^4$ is heteroaryl.

In another embodiment, said pharmacophore containing compound, comprises a compound of Figure III or a pharmaceutically acceptable salt thereof:

Figure III

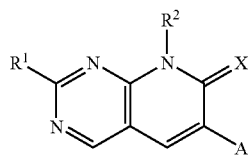

A is aryl or heteroaryl, wherein said aryl or heteroaryl is optionally substituted with one or more substituents selected from $R^3$;

X is NH, N-acyl, O or S;

$R^1$ and $R^2$ are independently H, OH, CHO, CN, halogen, $(C=O)_rO_s(C_1-C_{10})$alkyl, $(C=O)_rO_s(C_2-C_{10})$alkenyl, $(C=O)_rO_s(C_2-C_{10})$alkynyl, $(C=O)_rO_s$cycloalkyl, $(C=O)_rO_s$cycloalkenyl, $(C=O)_rO_s$cycloalkynyl, $(C=O)_rO_s$heterocycyl, $(C=O)_rO_s$aryl, $(C=O)_rO_s$heteroaryl, $(C=O)_rO_s$perfluoroalkyl or $(C_0-C_6)$alkyl-$NR^aR^b$, wherein said alkykl, alkenyl, alkynyl, cycyloalkyl, cycloalkenyl, cycloalkynyl, heterocycyl, aryl, heteroaryl and perfluoroalkyl is optionally substituted with one or more substituents selected from $R^3$;

$R^3$ is $(C=O)_rO_sNR^aR^b$, $(C=O)_rO_s$aryl, $(C=O)_rO_s$heterocycyl, halogen, OH, oxo, $(C=O)_rO_s(C_1-C_3)$perfluoroalkyl, $(C=O)_rO_sS_t(C_1-C_6)$alkyl, CHO, $CO_2H$, CN, $(C_0-C_6)$alkyl-$NR^aR^b$ or $(C_1-C_6)$alkyl-heterocycyl;

$R^a$ and $R^b$ independently are H, $(C=O)_rO_s(C_1-C_{10})$alkyl, $SO_2R^1$, $(C=O)_rO_s$heterocycyl, $(C=O)_rO_s$aryl, $(C=O)_rO_s$heteroaryl or $CO_2R^1$, wherein r, s and t independently are 0 or 1 and said alkyl, heterocycyl, aryl or heteroaryl is optionally substituted with one or more substituents selected from $R^3$.

In another embodiment, A is aryl.

In another embodiment, the aryl is 2,5-dichlorophenyl.

In another embodiment, $R^1$ is $(C_0-C_6)$alkyl-$NR^aR^b$ and $R^2$ is $(C=O)_rO_s(C_1-C_{10})$alkyl.

In another embodiment, $(C=O)_rO_s(C_1-C_{10})$alkyl is methyl.

In another embodiment, $(C_0-C_6)$alkyl-$NR^aR^b$ is

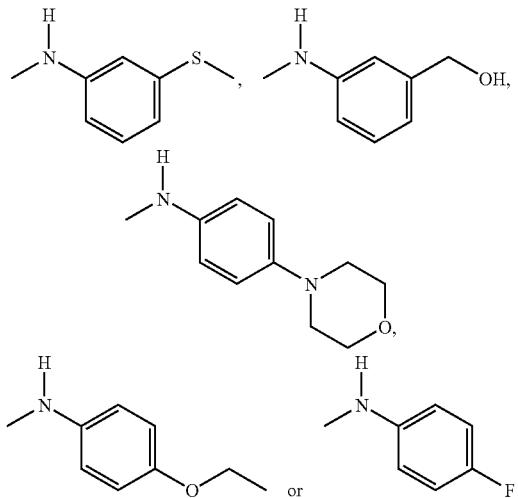

or a pharmaceutically acceptable salt thereof.

In another aspect, the invention provides a pharmaceutical composition useful for modulating Aβ level in a cell or tissue, comprising:

an amount of the compound described hereinabove sufficient to modulate said Aβ level; and a pharmaceutically acceptable excipient or carrier.

In one embodiment, the pharmaceutical composition is useful for modulating Aβ levels exhibited by a cell or tissue.

In another embodiment, the compound is present in an amount sufficient to modulate said Aβ levels.

Compounds according to Figure I may be prepared by various processes known to one of skill in the art. In particular, compounds according to Figure I, wherein A is CH, B is N, C is CH and $R^1$ is H may be prepared by the following process:

a) a compound according to Figure IV

Figure IV

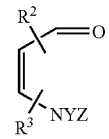

wherein Y and Z constitute $(C_1-C_6)$alkyl groups and $R^2$ and $R^3$ are as above-defined is reacted with a compound according to Figure V

Figure V

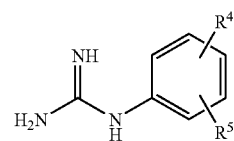

wherein $R^4$ and $R^5$ are as above-defined.

In certain embodiments, the compound is a compound identified by the methods of the invention, wherein the compound modulates γ-secretase activity, e.g., ATP-dependent γ-secretase activity, and wherein modulation of γ-secretase activity results in an alteration in the level of Aβ exhibited by a cell or tissue. γ-secretase activity is well known in the art, and includes cleavage of APP at the γ-secretase cleavage region.

In one embodiment, a method is provided for modulating γ-secretase activity in cells or tissues of interest in vitro.

In another embodiment, γ-secretase activity in cells or tissues of interest is modulated in situ or in vivo. The in vitro, in situ and in vivo applications may include, but are not limited to modulating activity in any of the cells or tissues disclosed hereinabove.

According to the invention, a substance "exhibited by a cell or tissue" encompasses a substance that it produced, sequestered, taken up or released by, the cell or tissue and that either remains within the cell (or tissue), i.e., intracellularly, or is secreted or released by the cell (or tissue) (extracellularly).

5.1.1. Therapeutic Methods

The present invention provides methods for prevention, treatment, e.g., management, of an Aβ-related disorder, or amelioration of a symptom of an Aβ-related disorder such as Alzheimer's disease. It is understood that the methods described herein in the context of treating and/or ameliorating a symptom can also routinely be utilized as part of a prevention protocol.

The invention also provides a method of treating, or ameliorating a symptom of, an Aβ-related disorder comprising administering to a subject in need of such treating or ameliorating an amount of a compound sufficient to reduce Aβ levels in the subject, wherein the compound modulates an ATP-dependent enzymatic activity, such that the Aβ-related disorder is treated or a symptom of the Aβ related disorder is ameliorated.

In one embodiment, the Aβ related disorder is Alzheimer's disease. In another embodiment, progression of the Aβ related disorder is slowed. In another embodiment, progression of the Aβ related disorder is reversed.

In another embodiment, the subject is a human subject. In a specific embodiment, the subject is a subject at risk for a familial form of Alzheimer's disease.

In another embodiment, the ATP-dependent enzymatic activity is lowered. In another embodiment, the compound crosses the blood-brain barrier. In another embodiment, the compound is administered orally. As used herein, this can mean either concurrent or sequential administration.

In another embodiment, the compound is administered with a NSAID. In a specific embodiment, the NSAID is sulindac sulfide, flufenamic acid, ibuprofen, flurbiprofen, fenoprofen, mefenamic acid, indomethacin, carprofen, meclofenamic acid.

In another embodiment, the compound is administered with an antioxidant. In a specific embodiment, the antioxidant is selected from the group consisting of vitamin E, vitamin C, curcumin, and Gingko biloba.

In another embodiment, the compound is administered with an acetylcholinesterase inhibitor.

In another embodiment, the compound is an ATP modulator. In another embodiment, the compound is ATP modulator is a selective modulator.

In another embodiment, the enzymatic activity is a γ-secretase activity. In another embodiment, the compound binds a γ-secretase enzyme exhibiting an ATP-dependent enzymatic activity.

In another embodiment, the ATP modulator competes with ATP for binding to an ATP binding site.

In one embodiment, the compound is STI-571 or a blood-brain barrier permeable variant thereof, or a pharmaceutically acceptable salt thereof. In another embodiment, the compound is a mesylate salt of STI-571. In another embodiment, the compound is WGB-BC-15 or a blood-brain barrier permeable variant thereof, or a pharmaceutically acceptable salt thereof. In another embodiment, the compound is any of Compounds 1-5 or a blood-brain barrier permeable variant thereof, or a pharmaceutically acceptable salt thereof.

In one embodiment, the enzymatic activity is a kinase activity. In one embodiment, the compound binds to a kinase enzyme exhibiting an ATP-dependent enzymatic activity. In one embodiment, the compound competes with ATP for binding to an ATP-binding site on the kinase. In another embodiment, the compound binds to a site other than an ATP-binding site on the kinase.

In a specific embodiment, the kinase is a tyrosine kinase. In another embodiment, the tyrosine kinase is Abl kinase, BCR-Abl kinase, ARG kinase, src kinase, c-kit, platelet-derived growth factor receptor.

In a specific embodiment, the kinase is a serine/threonine kinase, a carbohydrate kinase or a lipid kinase.

In another embodiment, the enzymatic activity is activity of a protease (e.g., AAA protease of the kind localized to the inner mitochondrial membrane), phosphatase, or a molecular chaperone molecule (e.g., hsp 60, hsp70, hsp90).

The invention also provides a method of treating, or ameliorating a symptom of, an Aβ-related disorder comprising administering to a subject in need of such treating or ameliorating an amount of an ATP modulator sufficient to reduce Aβ levels in the subject, such that the Aβ-related disorder is treated or a symptom of the Aβ related disorder is ameliorated.

In one embodiment, the Aβ related disorder is Alzheimer's disease. In one embodiment, the subject is a human subject.

In one embodiment, the subject is a subject at risk for a familial form of Alzheimer's disease.

In another embodiment, the ATP modulator crosses the blood-brain barrier.

In another embodiment, the ATP modulator is administered orally. In another embodiment, the ATP modulator is administered with a NSAID. In another embodiment, the NSAID is sulindac sulfide, flufenamic acid, ibuprofen, flurbiprofen, fenoprofen, mefenamic acid, indomethacin, carprofen, meclofenamic acid.

In another embodiment, the ATP modulator is administered with an antioxidant. In another embodiment, the antioxidant is selected from the group consisting of vitamin E, vitamin C, curcumin, and Gingko biloba.

In another embodiment, the ATP modulator is administered with an acetylcholinesterase inhibitor.

In another embodiment, the ATP modulator is a selective modulator.

In another embodiment, the enzymatic activity is a γ-secretase activity.

In one embodiment, the compound binds a γ-secretase enzyme exhibiting an ATP-dependent enzymatic activity. In another embodiment, the ATP modulator competes with ATP for binding to an ATP binding site.

In one embodiment, the compound is STI-571 or a blood-brain barrier permeable variant thereof, or a pharmaceutically acceptable salt thereof. In another embodiment, the compound is a mesylate salt of STI-571. In another embodiment, the compound is WGB-BC-15 or a blood-brain barrier permeable variant thereof, or a pharmaceutically acceptable salt thereof. In another embodiment, the compound is any of Compounds 1-5 or a blood-brain barrier permeable variant thereof, or a pharmaceutically acceptable salt thereof.

In one embodiment, the enzymatic activity is a kinase activity. In one embodiment, the compound binds to a kinase enzyme exhibiting an ATP-dependent enzymatic activity. In one embodiment, the compound competes with ATP for binding to an ATP-binding site on the kinase. In another embodiment, the compound binds to a site other than an ATP-binding site on the kinase.

In a specific embodiment, the kinase is a tyrosine kinase. In another embodiment, the tyrosine kinase is Abl kinase, BCR-Abl kinase, ARG kinase, src kinase, c-kit, platelet-derived growth factor receptor.

In a specific embodiment, the kinase is a serine/threonine kinase, a carbohydrate kinase or a lipid kinase.

In another embodiment, the enzymatic activity is activity of a protease (e.g., AAA protease of the kind localized to the inner mitochondrial membrane), phosphatase, or a molecular chaperone molecule (e.g., hsp 60, hsp70, hsp90).

The invention also provides a method of treating, or ameliorating a symptom of, an Aβ-related disorder comprising administering to a subject in need of such treating or ameliorating an amount of a compound sufficient to reduce Aβ levels in the subject, such that the Aβ-related disorder is treated or a symptom of the Aβ-related disorder is ameliorated, wherein the compound contains the following pharmacophore:
wherein X is CH—, O, NH or N—CO—.

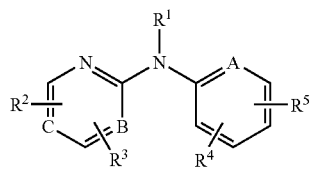

In one embodiment, said pharmacophore containing compound comprises a compound of Figure I or a pharmaceutically acceptable salt thereof:
Figure I

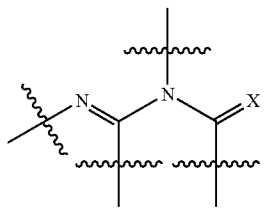

A is CH or N;
B and C are independently CH, N or $N^+$—O—;
$R^1$ is H, $SO_2R^a$, $(C=O)_rO_sR^a$;
$R^2$, $R^3$, $R^4$ and $R^5$ are independently H, OH, CHO, CN, halogen, $(C=O)_rO_s(C_1-C_{10})$alkyl, $(C=O)_rO_s(C_2-C_{10})$alkenyl, $(C=O)_rO_s(C_2-C_{10})$alkynyl, $(C=O)_rO_s$cycloalkyl, $(C=O)_rO_s$cycloalkenyl, $(C=O)_rO_s$cycloalkynyl, $(C=O)_rO_s$heterocycyl, $(C=O)_rO_s$aryl, $(C=O)_rO_s$heteroaryl, $(C=O)_rO_s$perfluoroalkyl or $(C_0-C_6)$alkyl-$NR^bR^c$,
wherein said alkykl, alkenyl, alkynyl, cycyloalkyl, cycloalkenyl, cycloalkynyl, heterocycyl, aryl, heteroaryl and perfluoroalkyl is optionally substituted with one or more substituents selected from $R^6$;

$R^6$ is $(C=O)_rO_sNR^aR^b$, $(C=O)_rO_s$aryl, $(C=O)_rO_s$heterocycyl, halogen, OH, oxo, $(C=O)_rO_s(C_1-C_3)$perfluoroalkyl, $(C=O)_rO_s(C_1-C_6)$alkyl, CHO, $CO_2H$, CN, $(C_0-C_6)$alkyl-$NR^bR^c$ or $(C_1-C_6)$alkyl-heterocycyl,
wherein said alkyl-heterocycyl is optionally substituted with OH;
$R^1$ is $(C_1-C_6)$alkyl, aryl or heterocycyl; and
$R^b$ and $R^c$ independently are H, $(C=O)_rO_s(C_1-C_{10})$alkyl, $SO_2R^a$, $(C=O)_rO_s$heterocycyl, $(C=O)_rO_s$aryl, $(C=O)_rO_s$heteroaryl or $CO_2R^a$,
wherein r and s independently are 0 or 1 and said alkyl, heterocycyl, aryl or heteroaryl is optionally substituted with one or more substituents selected from $R^6$.

In another embodiment, A is CH, B is N and C is CH.
In another embodiment, $R^1$ is H.
In another embodiment, $R^2$ is H and $R^3$ is heteroaryl.
In another embodiment, $R^4$ is $(C=O)_rO_s(C_1-C_{10})$alkyl and $R^5$ is $(C_0-C_6)$alkyl-$NR^bR^c$.
In another embodiment, $R^3$ is 3-pyridinyl.
In another embodiment, r is 0, s is 0 and $(C_1-C_{10})$alkyl is methyl.
In another embodiment, $(C_0-C_6)$alkyl is a direct bond $(C_0)$, $R^b$ is H and $R^c$ is $(C=O)_rO_s$heteroaryl or $(C=O)_rO_s$heterocycyl.
In another embodiment, $(C=O)_rO_s$heterocycyl is 4-hydroxy-1-piperazino, as illustrated below or a pharmaceutically acceptable salt thereof.

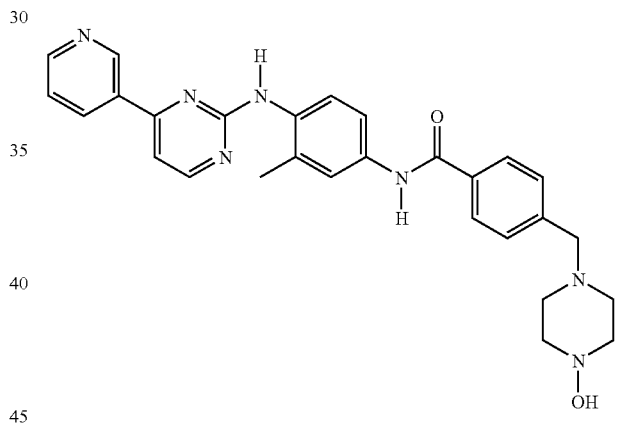

In another embodiment, the pharmacophore containing compound comprises a compound of Figure II or a pharmaceutically acceptable salt thereof:
Figure II

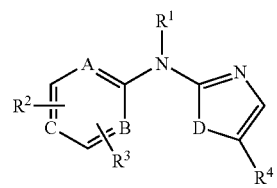

A, B and C are independently CH, N or $N^+$—O—;
D is O, S or N—$R^5$;
$R^1$ is H, $SO_2R^a$, $(C=O)_rR^a$ or $CO_2R^a$;
$R^2$, $R^3$ and $R^4$ are independently H, OH, CHO, CN, halogen, $(C=O)_rO_s(C_1-C_{10})$alkyl, $(C=O)_rO_s(C_2-C_{10})$alkenyl, $(C=O)_rO_s(C_2-C_{10})$alkynyl, $(C=O)_rO_s$cycloalkyl, $(C=O)_rO_s$cycloalkenyl, $(C=O)_r$ $O_s$cycloalkynyl, $(C=O)_rO_s$heterocycyl, $(C=O)_rO_s$aryl, $(C=O)_rO_s$heteroaryl, $(C=O)_rO_s$perfluoroalkyl or $(C_0-C_6)$alkyl-$NR^bR^c$,
wherein said alkykl, alkenyl, alkynyl, cycyloalkyl, cycloalkenyl, cycloalkynyl, heterocycyl, aryl, heteroaryl and perfluoroalkyl is optionally substituted with one or more substituents selected from $R^6$;

$R^5$ is H, aryl or $(C_1-C_6)$alkyl;

$R^6$ is $(C=O)_rO_sNR^aR^b$, $(C=O)_rO_s$aryl, $(C=O)_rO_s$heterocycyl, halogen, OH, oxo, $(C=O)_rO_s(C_1-C_3)$perfluoroalkyl, $(C=O)_rO_s(C_1-C_6)$alkyl, CHO, $CO_2H$, CN, $(C_0-C_6)$alkyl-$NR^bR^c$ or $(C_1-C_6)$alkyl-heterocycyl;

$R^a$ is $(C_1-C_6)$alkyl, aryl or heterocycyl; and $R^b$ and $R^c$ independently are H, $(C=O)_rO_s(C_1-C_{10})$alkyl, $SO_2R^a$, $(C=O)_rO_s$heterocycyl, $(C=O)_rO_s$aryl, $(C=O)_r$ $O_s$heteroaryl or $CO_2R^a$, wherein r and s independently are 0 or 1 and said alkyl, heterocycyl, aryl or heteroaryl is optionally substituted with one or more substituents selected from $R^6$.

In another embodiment, $R^1$ is H.

In another embodiment, $R^2$ is H and $R^3$ is $(C_0-C_6)$alkyl-$NR^bR^c$.

In another embodiment, $R^4$ is heteroaryl.

In another embodiment, said pharmacophore containing compound, comprises a compound of Figure III or a pharmaceutically acceptable salt thereof:

Figure III

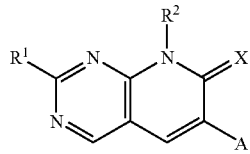

A is aryl or heteroaryl,
wherein said aryl or heteroaryl is optionally substituted with one or more substituents selected from $R^3$;

X is NH, N-acyl, O or S;

$R^1$ and $R^2$ are independently H, OH, CHO, CN, halogen, $(C=O)_rO_s(C_1-C_{10})$alkyl, $(C=O)_rO_s(C2-C_{10})$alkenyl, $(C=O)_rO_s(C2-C_{10})$alkynyl, $(C=O)_rO_s$cycloalkyl, $(C=O)_rO_s$cycloalkenyl, $(C=O)_rO_s$cycloalkynyl, $(C=O)_rO_s$heterocycyl, $(C=O)_rO_s$aryl, $(C=O)_rO_s$heteroaryl, $(C=O)_rO_s$perfluoroalkyl or $(C_0-C_6)$alkyl-$NR^aR^b$, wherein said alkykl, alkenyl, alkynyl, cycyloalkyl, cycloalkenyl, cycloalkynyl, heterocycyl, aryl, heteroaryl and perfluoroalkyl is optionally substituted with one or more substituents selected from $R^3$;

$R^3$ is $(C=O)_rO_sNR^aR^b$, $(C=O)_rO_s$aryl, $(C=O)_rO_s$heterocycyl, halogen, OH, oxo, $(C=O)_rO_s(C_1-C_3)$perfluoroalkyl, $(C=O)_rO_sS_t(C_1-C_6)$alkyl, CHO, $CO_2H$, CN, $(C_0-C_6)$alkyl-$NR^aR^b$ or $(C_1-C_6)$alky-heterocycyl;

$R^a$ and $R^b$ independently are H, $(C=O)_rO_s(C_1-C_{10})$alkyl, $SO_2R^1$, $(C=O)_rO_s$heterocycyl, $(C=O)_rO_s$aryl, $(C=O)_r$ $O_s$heteroaryl or $CO_2R^a$, wherein r, s and t independently are 0 or 1 and said alkyl, heterocycyl, aryl or heteroaryl is optionally substituted with one or more substituents selected from $R^3$.

In another embodiment, A is aryl.

In another embodiment, aryl is 2,5-dichlorophenyl.

In another embodiment, $R^1$ is $(C_0-C_6)$alkyl-$NR^aR^b$ and $R^2$ is $(C=O)_rO_s(C_1-C_{10})$alkyl.

In another embodiment, $(C=O)_rO_s(C_1-C_{10})$alkyl is methyl.

In another embodiment, $(C_0-C_6)$alkyl-$NR^aR^b$ is

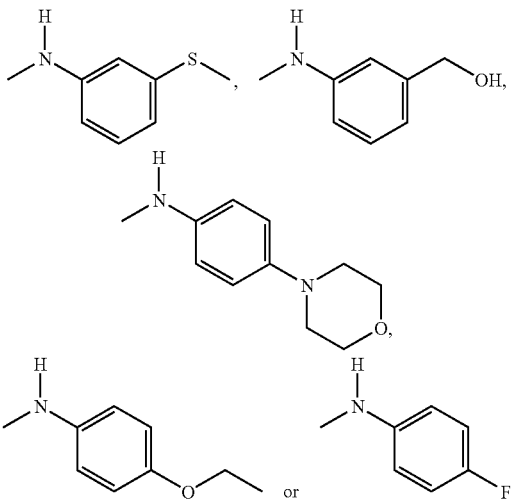

or a pharmaceutically acceptable salt thereof.

In another embodiment, the agent is administered orally.

In one embodiment, the compound is administered with a NSAID. In another embodiment, the NSAID is sulindac sulfide, flufenamic acid, ibuprofen, flurbiprofen, fenoprofen, mefenamic acid, indomethacin, carprofen, meclofenamic acid.

In one embodiment, the compound is administered with an antioxidant. In a specific embodiment, the antioxidant is selected from the group consisting of vitamin E, vitamin C, curcumin, and Gingko biloba.

In another embodiment, the compound is administered with an acetylcholinesterase inhibitor.

5.1.2. Modulating Compounds 5.1.2.1. Compounds That Modulate Aβ Levels

The present invention also provides compositions for modulating Aβ levels exhibited by a cell or tissue, including, but not limited to the following compounds (or agents) disclosed hereinbelow. The invention also provides compositions for modulating the level Aβ via modulation of the activity of γ-secretase, including, but not limited to the following agents, drugs, compounds or small molecules disclosed hereinbelow.

In one embodiment, the invention provides a composition for modulating Aβ level exhibited by a cell or tissue comprising a modulator of ATP-dependent γ-secretase activity and a pharmaceutically acceptable vehicle. In one aspect of this embodiment, the Aβ level is lowered. In another aspect, the Aβ level is raised. In another aspect, the Aβ is Aβ40. In another aspect, the Aβ is Aβ42. In another aspect, the modulator binds to a kinase. In another aspect, the modulator competes with ATP for binding to the ATP-binding site on a kinase. In another aspect, the compound binds to a site other than an ATP-binding site on the kinase. In another aspect, the compound is an ATP modulator. In another aspect, the kinase may be, e.g., Abl kinase, ARG kinase, BCR-Abl kinase, src kinase, c-kit or platelet-derived growth factor receptor. In another aspect, the modulator does not modulate Abl kinase activity. In another aspect, the modulator is an inhibitor of ATP-dependent enzymatic activity. In another aspect, the modulator does not inhibit Notch-1 cleavage. In another aspect, the modulator can cross the blood-brain barrier. In another aspect, the inhibitor is a selective inhibitor. In another aspect, the selective inhibitor is STI-571, WGB-BC-415, Compound 1, Compound 2, Compound 3, Compound 4, Compound 5 or a blood-brain barrier permeable variant thereof.

Among the preferred compounds are those that are ATP modulators.

In certain embodiments, the ATP modulator, such as an ATP inhibitor, may include, but not be limited to, a phenylaminopyrimidine tyrosine kinase inhibitor, e.g., 2-phenylaminopyrimidine, a pyrimidinyl pyridone tyrosine kinase inhibitor, 2-(Purin-9-yl)-tetrahydrofuran-3,4-diol derivatives; pyridoxine and pyridoxal analogues; N-6 heterocyclic 8-modified adenosine derivatives; N-6 heterocyclic 5'-modified adenosine derivatives; allosteric inhibitors of pyruvate kinase; 8-phenylxanthines, 8-cycloalkylxantines or 8-substituted xanthine derivatives; N-6 substituted adenosine-5'-uronamides; purine, pyrrolo[2,3,d]pyrimidine and pyrazolo[3,4,d]pyrimidine nucleoside analogs.

In another embodiment, the compound, e.g., ATP modulator, may include, but not be limited to, the following compounds:

Heterocyclic-hydroxyimino-fluorene nuclei compounds; 3-anilinomethylene oxindoles; 3-(4'-bromobenzylindenyl)-2-indolinone analogues; indeno[1,2,c]-naphthol[1,2,c] and benzo[6,7]cyclohepta[1,2,c]pyrazole derivatives; 3'-epimeric k-252a derivatives; quinazolines; 3-cyano-[1,7], [1,5] and [1,8]-napthyridine analogues; N-[4-(3-chloro-4-fluoro-phenylamino)-7-(3-morpholin4-yl-propoxy)-quinazolin-6-yl]-acrylamide; pyrimidine derivatives; benzimidazoles; bicyclic heteroaromatic compounds; pyrrolopyrimidines; quinoline and quinoxaline derivatives; indolinones; 2-pyrimidineamine derivatives; substituted pyrido[3,2,d]pyrimidines; fused polycyclic 2-aminopyrimidine derivatives; bicyclic 4-aralkylaminopyrimidine derivatives; N-7-heterocycyl pyrrolo[2,3,d]pyrimidines; 3-cyano quinoline derivatives; pyrazole derivatives; pyrimido[5,4,d]pyrimidines; 4-anilinoquinazoline derivatives; 6-aryl napthyridines; N-oxides of amino containing pyrido[2,3,d]pyrimidines; 5-aminopyrazoles; 5,10-dihydropyrimido[4,5,b]quinolin-4(1H)-one; quinolymethylen-oxindole analogues; acrylonitrile-sulfonamide derivatives; 3-(4'-dimethylaminobenzylidenyl)-2-indolines; 3-(2'-alkoxybenzylidenyl)$_2$-indolines; 3-(4'-bromobenzylidenyl)-2-indolines; benzylidene-Z-indoline compounds; 4,6-dianilino-pyrimidine derivatives; substituted indolylmethylene-oxindole analogues; hydrosoluble 3-arylidene-2-oxindole analogues; 3-(2'-halobenzylidenyl)-2-indolinone compounds; 3-heteroaryl-2-indolinone compounds; benzoylethylene derivatives; urea and thiourea-type compounds; benzopyran derivatives; pyrido[2,3,d]pyrimidines; 6-aryl-pyrido[2,3,d]pyrimidines and naphthyridines; substituted 3-arylidene-7-azaoxindole compounds; thienyl compounds; aryl and heteroaryl quinazoline compounds; arylidene and heteroarylidene oxindole derivatives; N-substituted-beta-aryl and beta-heteroaryl-alpha-cyanoacrylamide derivatives; 2-iminochromene derivatives; 4-aminopyrrolo[2,3,d]pyrimidines; 4-aminopyrazolo(3,4,d)pyrimidine derivatives; 4-aminopyrazolo(3,4,d)pyridine derivatives; 3-(cycloalkanoheteroarylidenyl)-2-indolinones; isoxazole-4-carboxamide compounds; 3-(cycloalkanoheteroarylidenyl)-2-indolinones; substituted phenylacrylonitrile compounds; benzylidene-Z-indoline compounds; 3-(2'-halobenzylidenyl)-2-indolinone compounds; benzopyran compounds; or 4-aminopyrimidines; isoxazole compounds. Such compounds can, for example, be utilized as kinase modulators, e.g., inhibitors.

Appropriate compounds can also include, for example, STI-571, mesylate salt of STI-571 (imatinib mesylate, GLEEVEC™, Novartis Pharmaceuticals), and congeners thereof, members of the 2-phenylaminopyrimidine class of compounds, such as Compounds 1-5, as well as compounds that compete for the ATP binding sites of Bcr-Abl, Abl kinase, or c-kit, platelet-derived growth factor receptors (PDGFR), and on any other kinases known or later shown to be inhibited by STI-571, or a related compound, such as the pyridone tyrosine kinase inhibitor class, would be candidates for use in the present invention.

In another embodiment, agents of the invention inhibit γ-secretase activity either by binding to a site on γ-secretase, or on a component protein of γ-secretase.

Still further, compounds that can be used as part of the methods of the invention include, but are not limited to, compounds that contain the following pharmacophore:
wherein X is CH—, O, NH or N—CO—.

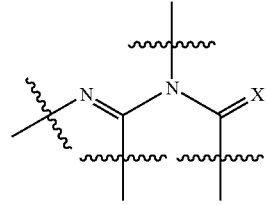

In one embodiment, said pharmacophore containing compound comprises a compound of Figure I or a pharmaceutically acceptable salt thereof:

Figure I

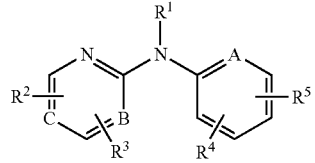

A is CH or N;
B and C are independently CH, N or N$^+$—O—;
$R^1$ is H, SO$_2$R$^a$, (C=O)$_r$O$_s$R$^a$;
$R^2$, $R^3$, $R^4$ and $R^5$ are independently H, OH, CHO, CN, halogen, (C=O)$_r$O$_s$(C$_1$-C$_{10}$)alkyl, (C=O)$_r$O$_s$(C$_2$-C$_{10}$)alkenyl, (C=O)$_r$O$_s$(C$_2$-C$_{10}$)alkynyl, (C=O)$_r$O$_s$cycloalkyl, (C=O)$_r$O$_s$cycloalkenyl, (C=O)$_r$O$_s$cycloalkynyl, (C=O)$_r$O$_s$heterocycyl, (C=O)$_r$O$_s$aryl, (C=O)$_r$O$_s$heteroaryl, (C=O)$_r$O$_s$perfluoroalkyl or (C$_0$-C$_6$)alkyl-NR$^b$R$^c$,
wherein said alkykl, alkenyl, alkynyl, cycyloalkyl, cycloalkenyl, cycloalkynyl, heterocycyl, aryl, heteroaryl and perfluoroalkyl is optionally substituted with one or more substituents selected from $R^6$;
$R^6$ is (C=O)$_r$O$_s$NR$^a$R$^b$, (C=O)$_r$O$_s$aryl, (C=O)$_r$O$_s$heterocycyl, halogen, OH, oxo, (C=O)$_n$O$_s$(C$_1$-C$_3$)perfluoroalkyl, (C=O)$_r$O$_s$(C$_1$-C$_6$)alkyl, CHO, CO$_2$H, CN, (C$_0$-C$_6$)alkyl-NR$^b$R$^c$ or (C$_1$-C$_6$)alkyl-heterocycyl,
wherein said alkyl-heterocycyl is optionally substituted with OH;
$R^a$ is (C$_1$-C$_6$)alkyl, aryl or heterocycyl; and
$R^b$ and $R^c$ independently are H, (C=O)$_r$O$_s$(C$_1$-C$_{10}$)alkyl, SO$_2$R$^a$, (C=O)$_r$O$_s$heterocycyl, (C=O)$_r$O$_s$aryl, (C=O)$_r$O$_s$heteroaryl or CO$_2$R$^a$, wherein r and s independently are 0 or 1 and said alkyl, heterocycyl, aryl or heteroaryl is optionally substituted with one or more substituents selected from $R^6$.

In another embodiment, A is CH, B is N and C is CH.

In another embodiment, $R^1$ is H.

In another embodiment, $R^2$ is H and $R^3$ is heteroaryl.

In another embodiment, $R^4$ is $(C=O)_rO_s(C_1-C_{10})$alkyl and $R^5$ is $(C_0-C_6)$alkyl-$NR^bR^c$.

In another embodiment, $R^3$ is 3-pyridinyl.

In another embodiment, r is 0, s is 0 and $(C_1-C_{10})$alkyl is methyl.

In another embodiment, $(C_0-C_6)$alkyl is a direct bond $(C_0)$, $R^b$ is H and $R^c$ is $(C=O)_rO_s$heteroaryl or $(C=O)_rO_s$heterocycyl.

In another embodiment, $(C=O)_rO_s$heterocycyl is 4-hydroxy-1-piperazino, as illustrated below or a pharmaceutically acceptable salt thereof.

In another embodiment, $(C=O)_rO_s$heteroaryl is 3-pyrindinyl, as illustrated below or a pharmaceutically acceptable salt thereof.

In another embodiment, said pharmacophore containing compound, comprises a compound of Figure II or a pharmaceutically acceptable salt thereof:

Figure II

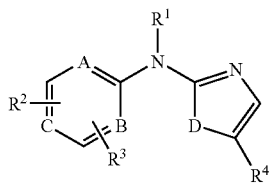

A, B and C are independently CH, N or $N^+$—O—;

D is O, S or N—$R^5$;

$R^1$ is H, $SO_2R^a$, $(C=O)_rR^a$ or $CO_2R^a$;

$R^2$, $R^3$ and $R^4$ are independently H, OH, CHO, CN, halogen, $(C=O)_rO_s(C_1-C_{10})$alkyl, $(C=O)_rO_s(C_2-C_{10})$alkenyl, $(C=O)_rO_s(C_2-C_{10})$alkynyl, $(C=O)_rO_s$cycloalkyl, $(C=O)_rO_s$cycloalkenyl, $(C=O)_rO_s$cycloalkynyl, $(C=O)_rO_s$heterocycyl, $(C=O)_rO_s$aryl, $(C=O)_rO_s$heteroaryl, $(C=O)_rO_s$perfluoroalkyl or $(C_0-C_6)$alkyl-$NR^bR^c$, wherein said alkykl, alkenyl, alkynyl, cycyloalkyl, cycloalkenyl, cycloalkynyl, heterocycyl, aryl, heteroaryl and perfluoroalkyl is optionally substituted with one or more substituents selected from $R^6$;

$R^5$ is H, aryl or $(C_1-C_6)$alkyl;

$R^6$ is $(C=O)_rO_sNR^aR^b$, $(C=O)_rO_s$aryl, $(C=O)_rO_s$heterocycyl, halogen, OH, oxo, $(C=O)_rO_s(C_1-C_3)$perfluoroalkyl, $(C=O)_rO_s(C_1-C_6)$alkyl, CHO, $CO_2H$, CN, $(C_0-C_6)$alkyl-$NR^bR^c$ or $(C_1-C_6)$alkyl-heterocycyl;

$R^a$ is $(C_1-C_6)$alkyl, aryl or heterocycyl; and $R^b$ and $R^c$ independently are H, $(C=O)_rO_s(C_1-C_{10})$alkyl, $SO_2R^a$, $(C=O)_rO_s$heterocycyl, $(C=O)_rO_s$aryl, $(C=O)_r O_s$heteroaryl or $CO_2R^a$, wherein r and s independently are 0 or 1 and said alkyl, heterocycyl, aryl or heteroaryl is optionally substituted with one or more substituents selected from $R^6$.

In another embodiment, $R^1$ is H.

In another embodiment, $R^2$ is H and $R^3$ is $(C_0-C_6)$alkyl-$NR^bR^c$.

In another embodiment, $R^4$ is heteroaryl.

In another embodiment, said pharmacophore containing compound, comprises a compound of Figure III or a pharmaceutically acceptable salt thereof:

Figure III

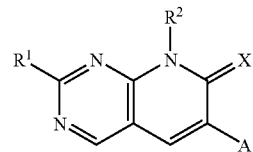

A is aryl or heteroaryl, wherein said aryl or heteroaryl is optionally substituted with one or more substituents selected from $R^3$;

X is NH, N-acyl, O or S;

$R^1$ and $R^2$ are independently H, OH, CHO, CN, halogen, $(C=O)_rO_s(C_1-C_{10})$alkyl, $(C=O)_rO_s(C_2-C_{10})$alkenyl, $(C=O)_rO_s(C_2-C_{10})$alkynyl, $(C=O)_rO_s$cycloalkyl, $(C=O)_rO_s$cycloalkenyl, $(C=O)_rO_s$cycloalkynyl, $(C=O)_rO_s$heterocycyl, $(C=O)_rO_s$aryl, $(C=O)_rO_s$heteroaryl, $(C=O)_rO_s$perfluoroalkyl or $(C_0-C_6)$alkyl-$NR^aR^b$, wherein said alkykl, alkenyl, alkynyl, cycyloalkyl, cycloalkenyl, cycloalkynyl, heterocycyl, aryl, heteroaryl and perfluoroalkyl is optionally substituted with one or more substituents selected from $R^3$;

$R^3$ is $(C=O)_rO_sNR^aR^b$, $(C=O)_rO_s$aryl, $(C=O)_rO_s$heterocycyl, halogen, OH, oxo, $(C=O)_rO_s(C_1-C_3)$perfluoroalkyl, $(C=O)_rO_sS_t(C_1-C_6)$alkyl, CHO, $CO_2H$, CN, $(C_0-C_6)$alkyl-$NR^aR^b$ or $(C_1-C_6)$alkyl-heterocycyl;

$R^a$ and $R^b$ independently are H, $(C=O)_rO_s(C_1-C_{10})$alkyl, $SO_2R^a$, $(C=O)_rO_s$heterocycyl, $(C=O)_rO_s$aryl, $(C=O)_r O_s$heteroaryl or $CO_2R^1$, wherein r, s and t independently are 0 or 1 and said alkyl, heterocycyl, aryl or heteroaryl is optionally substituted with one or more substituents selected from $R^3$.

In another embodiment, A is aryl.

In another embodiment, the aryl is 2,5-dichlorophenyl.

In another embodiment, $R^1$ is $(C_0-C_6)$alkyl-$NR^aR^b$ and $R^2$ is $(C=O)_rO_s(C_1-C_{10})$alkyl.

In another embodiment, $(C=O)_rO_s(C_1-C_{10})$alkyl is methyl.

In another embodiment, $(C_0-C_6)$alkyl-$NR^aR^b$ is

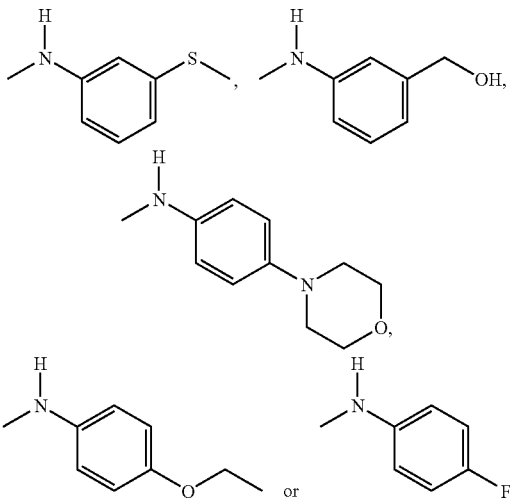

or a pharmaceutically acceptable salt thereof.

Compounds according to Figure I may be prepared by various processes known to one of skill in the art. In particular, compounds according to Figure I, wherein A is CH, B is N, C is CH and $R^1$ is H may be prepared by the following process:

a) a compound according to Figure IV

Figure IV

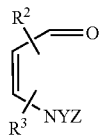

wherein Y and Z constitute $(C_1-C_6)$alkyl groups and $R^2$ and $R^3$ are as above-defined is reacted with a compound according to Figure V

Figure V

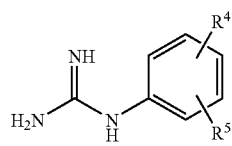

wherein $R^4$ and $R^5$ are as above-defined.

Compounds according to Figure II may be prepared by various processes known to one of skill in the art. In particular, compounds according to Figure II, wherein A is N, B is N, C is CH and $R^1$ is H may be prepared by the following process:

a) a compound according to Figure VI

Figure VI

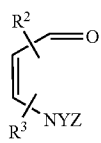

wherein Y and Z constitute $(C_1-C_6)$alkyl groups and $R^2$ and $R^3$ are as above-defined is reacted with a compound according to Figure VII

Figure VII

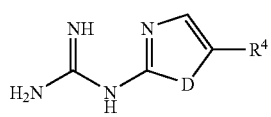

wherein D and $R^4$ are as above-defined.

Compounds according to Figure III may be prepared by various processes known to one of skill in the art. In particular, compounds according to Figure III, wherein X is O may be prepared by the following process:

a) a compound according to Figure VIII

Figure VIII

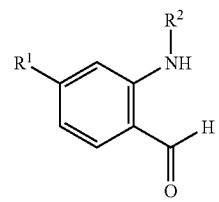

wherein $R^1$ and $R^2$ are as above-defined is reacted under basic conditions with a compound according to Figure IX

Figure IX

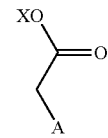

wherein X is a $(C_1-C_6)$alkyl group and A is as above-defined.

In one embodiment, the compounds utilized by the methods of the invention are none of those disclosed in U.S. Pat. No. 5,385,915 (incorporated herein by reference in its entirety), particularly at column 11, lines 13-20.

Candidate compounds may be routinely assayed to determine which are appropriate ATP modulators using standard assays, e.g., Xu et al., 1997, Proc. Natl. Acad. Sci. USA 94: 3748-3752 or Zhang et al., 2001, Biochemistry 40: 5049-5055.

Preferably the compound (or agent) administered in the method of treatment can cross through the blood brain barrier in sufficient quantities and at a sufficient rate so as to allow the treatment of an Aβ-related disorder. In one such embodiment, the compound is administered intravenously. In another embodiment, the compound is administered orally. More preferably the compound can cross the blood brain barrier without a carrier (for methods and routes of administration, see Section 5.1.2.5).

Aβ, however, exists not only in brain tissues and in the central nervous system (CNS), but also outside the brain in peripheral tissues, such as blood and in most organs where Aβ is also produced by the processing of APP. A balance exists between brain Aβ and Aβ outside the brain (DeMattos et al, 2001, Proc. Natl. Acad. Sci. USA 98(15):8850-8855). Reduction of Aβ in the periphery results in a reduction of brain Aβ, presumably by re-partitioning of soluble Aβ. Thus, even compounds that do not cross the blood-brain barrier can be utilized in modulating Aβ levels and preventing or treating an Aβ-related disorder, or a symptom thereof.

5.1.2.2. Pharmaceutical Compositions and Formulations

The present invention provides pharmaceutical compositions of the agents, drugs or compounds of the invention disclosed hereinabove.

In one embodiment, the invention provides a pharmaceutical composition comprising an amount of a compound described hereinabove sufficient to modulate Aβ levels in a cell or tissue, and a pharmaceutically acceptable excipient or carrier.

In another embodiment, the pharmaceutical composition comprising a compound that lowers ATP-dependent Aβ levels in a cell or tissue, a compound selected from the group consisting of: an NSAID, e.g. sulindac sulfide, flufenamic acid, ibuprofen, flurbiprofen, fenoprofen, mefenamic acid, indomethacin, carprofen, meclofenamic acid, an antioxidant, e.g., vitamin E, vitamin C, curcumin, and Gingko biloba, a non-selective COX inhibitor and an acetylcholinesterase inhibitor, and a pharmaceutically acceptable excipient or carrier.

The agent, drug or compound, or their physiologically acceptable salts or solvates, may be formulated for administration for injection, or for oral, topical, nasal, inhalation, insufflation (either through the mouth or the nose) buccal, parenteral, rectal administration or other forms of administration. In certain embodiments, administration is accomplished by intrathecal administration via osmotic pumps, by oral gavage, or by intraperiotoneal injection.

The invention provides pharmaceutical compositions comprising sufficient amounts of an agent(s) of the invention together with pharmaceutically acceptable diluents, preservatives, solubilizers, emulsifiers, adjuvants, excipients and/or carriers. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimerosal, benzyl alcohol) and bulking substances (e.g., lactose, mannitol).

The compositions may also be incorporated into particulate preparations of polymeric compounds such as polylactic acid, polyglycolic acid, etc. or liposomes. Hyaluronic acid may also be used. Biocompatible absorbable polymers may be selected from the group consisting of aliphatic polyesters, copolymers and blends, which include, but are not limited to, homopolymers and copolymers of lactide (which include D-, L-, lactic acid and D-, L- and meso lactide), glycolide (including glycolic acid), epsilon-caprolactone, p-dioxanone (1,4-dioxan-2-one, which is disclosed in U.S. Pat. No. 4,052,988), alkyl substituted derivatives of p-dioxanone (i.e., 6,6-dimethyl-1,4-dioxan-2-one which is disclosed in U.S. Pat. No. 5,703,200), triethylene carbonate (1,3-dioxan-2-one), alkyl substituted derivatives of 1,3-dioxanone (which are disclosed in U.S. Pat. No. 5,412,068), delta-valerolactone, beta-butyrolactone, gamma-butyrolactone, epsilon-decalactone, hydroxybutyrate, hydroxyvalerate, 1,4-dioxepan-2-one (disclosed in U.S. Pat. No. 4,052,988 and its dimer 1,5,8,12-tetraoxacyclotetradecane-7,14 dione), 1,5-dioxepan-2-one, and polymer blends thereof.

Such compositions may influence physical state, stability, rate of in vivo release, and rate of in vivo clearance of the present proteins and derivatives. See, e.g., Remington's Pharmaceutical Sciences, 18th ed., (1990, Mack Publishing Co., Easton, Pa. 18042) pages 1435-1712). The compositions may be prepared in liquid form, or be in dried powder, such as lyophilized form.

Contemplated for use herein are oral solid dosage forms, which are disclosed generally in Remington=s Pharmaceutical Sciences, 18th Ed. 1990 (Mack Publishing Co. Easton Pa. 18042) at Chapter 89. Solid dosage forms include tablets, capsules, pills, troches or lozenges, cachets or pellets. Also, liposomal or proteinoid encapsulation may be used to formulate the present compositions (as, for example, proteinoid microspheres reported U.S. Pat. No. 4,925,673). Liposomal encapsulation may be used and the liposomes may be derivatized with various polymers (e.g., U.S. Pat. No. 5,013,556). A description of possible solid dosage forms for the therapeutic is given by Marshall, K. In: Modern Pharmaceutics Edited by G. S. Banker and C. T. Rhodes Chapter 10, 1979). In general, the formulation will include the agent and inert ingredients (which allow for protection against the stomach environment and release of the biologically active material in the intestine).

To ensure full gastric resistance a coating impermeable to at least pH 5.0 is useful. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L3OD, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings that make the tablet easier to swallow. Capsules may consist of a hard shell (such as gelatin) for delivery of dry therapeutic, i.e., powder; for liquid forms, a soft gelatin shell may be used. The shell material of cachets may be thick starch or other edible paper. For pills, lozenges, molded tablets or tablet triturates, moist massing techniques can be used.

The therapeutic can be included in the formulation as fine multi-particulates in the form of granules or pellets. The formulation of the material for capsule administration can also be as a powder, lightly compressed plugs or even as tablets. The therapeutic can also be prepared by compression.

Colorants and flavoring agents may all be included. For example, the protein (or derivative) may be formulated (such as by liposome or microsphere encapsulation) and then further contained within an edible product, such as a refrigerated beverage containing colorants and flavoring agents.

One may dilute or increase the volume of the therapeutic with an inert material or filler. These diluents or fillers can include carbohydrates, especially mannitol, a-lactose, anhydrous lactose, cellulose (e.g., microcrystalline cellulose), sucrose, calcium hydrogen phosphate modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include, but are not limited to, starch (e.g., potato starch or the commercial disintegrant based on starch, Explotab). Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch (e.g., pregelatinised maize starch) and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) can both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes, talc and silica. Soluble lubricants may also be used such as sodium lauryl sulfate, magnesium lauryl sulfate, polyethylene glycol of various molecular weights, Carbowax 4000 and 6000.

Glidants that can improve the flow properties of the drug during formulation and to aid rearrangement during compression can be added. The glidants can include starch, talc, pyrogenic silica and hydrated silicoaluminate.

To aid dissolution of the therapeutic into the aqueous environment a surfactant can be added as a wetting agent. Surfactants may include anionic detergents such as sodium lauryl sulfate, dioctyl sodium sulfosuccinate and dioctyl sodium sulfonate. Cationic detergents can be used and can include benzalkonium chloride or benzethomium chloride. The list of potential non-ionic detergents that can be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants can be present in the formulation of the protein or derivative either alone or as a mixture in different ratios.

Additives that potentially enhance uptake of the agent are, for example, the fatty acids oleic acid, linoleic acid and linolenic acid.

Controlled release oral formulation may be desirable. The agent can be incorporated into an inert matrix that permits release by either diffusion or leaching mechanisms, e.g., gums. Slowly degenerating matrices may also be incorporated into the formulation. Some enteric coatings also have a delayed release effect.

Another form of a controlled release of this therapeutic is by a method based on the Oros therapeutic system (Alza Corp.), i.e. the drug is enclosed in a semipermeable membrane, which allows water to enter and to push the drug out through a single small opening due to osmotic effects.

Other coatings may be used for the formulation. These include a variety of sugars that can be applied in a coating pan. The therapeutic agent can also be given in a film coated tablet and the materials used in this instance are divided into two groups. The first are the nonenteric materials and include methyl cellulose, ethyl cellulose, hydroxyethyl cellulose, methylhydroxy-ethyl cellulose, hydroxypropyl cellulose, hydroxypropyl-methyl cellulose, sodium carboxy-methyl cellulose, providone and the polyethylene glycols. The second group consists of the enteric materials that are commonly esters of phthalic acid.

A mix of materials can be used to provide the optimum film coating. Film coating may be carried out in a pan-coater or in a fluidized bed or by compression coating.

Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Nasal delivery of the agent is also contemplated. Nasal delivery allows the passage of the protein to the blood stream directly after administering the therapeutic product to the nose, without the necessity for deposition of the product in the lung. Formulations for nasal delivery include those with dextran or cyclodextran.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations disclosed previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device that may contain one or more unit dosage forms containing the active ingredient. The pack may for example comprise metal or plastic foil, such as a blister pack. The pack or dispenser device may be accompanied by instructions for administration.

Other pharmaceutical compositions can be co-administered (sequentially or concurrently) with the pharmaceutical composition of the invention. Co-administration can be accomplished by administration of such other pharmaceutical compositions in the same or in a different pharmaceutical composition as those described above. In one embodiment, an NSAID is co-administered, e.g., sulindac sulfide, flufenamic acid, ibuprofen, flurbiprofen, fenoprofen, mefenamic acid, indomethacin, carprofen or meclofenamic acid. In another embodiment, a non-selective COX inhibitor is co-administered. In another embodiment, a non-specific secretase inhibitor is co-administered. In another embodiment, an antioxidant is co-administered. In specific embodiments, the antioxidant is selected from the group consisting of vitamin E, vitamin C, curcumin, and Gingko biloba. In another embodiment, an acetylcholinesterase inhibitor is co-administered.

5.1.2.3. Articles of Manufacture

The present invention also provides an article of manufacture comprising packaging material and a pharmaceutical composition of the invention contained within the packaging material, said pharmaceutical composition in a form suitable for administration to a subject, preferably a human, or in a format that can be diluted or reconstituted for administration to the subject. In one embodiment, the article of manufacture further comprises printed instructions and/or a label directing the use or administration of the pharmaceutical composition.

In particular, the article of manufacture can comprise packaging material and a pharmaceutical composition comprising a compound that lowers ATP-dependent Aβ levels, and a pharmaceutically acceptable carrier contained within the packaging material, said pharmaceutical composition in a form suitable for administration to a subject. Such an article of manufacture can further comprise printed instructions regarding the use or administration of the pharmaceutical composition. For example, the instructions suggest a dosing regimen for the prevention, treatment, or amelioration of a symptom of an Aβ-related disorder such as for the prevention, treatment, or amelioration of a symptom of Alzheimer's disease. An article of manufacture of the invention can also further comprise a label regarding the use or administration of the pharmaceutical composition. For example, the label can suggest a dosing regimen for the prevention, treatment, or amelioration of a symptom of an Aβ-related disorder such as Alzheimer's disease. In one embodiment, the article of manufacture can further comprises an antioxidant, a non-selective COX inhibitor or an acetylcholinesterase inhibitor.

As with any pharmaceutical product, the packaging material and container of the articles of manufacture of the invention are designed to protect the stability of the product during storage and shipment. More specifically, the invention provides an article of manufacture comprising packaging material, such as a box, bottle, tube, vial, container, sprayer, insufflator, intravenous (i.v.) bag, envelope and the like; and at least one unit dosage form of a pharmaceutical composition of the invention contained within said packaging material.

5.1.2.4. Dosages

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically sufficient dose can be estimated initially from cell culture assays. A dose may be formulated in animal models to achieve a circulating plasma concentration range that includes the IC50 (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

In certain embodiments, treatment can begin at the first signs of mild cognitive impairment in a subject or patient, using standard methods for assessing mild cognitive impairment known in the art. In other embodiments, for example when a subject is at risk for familial Alzheimer's disease, treatment can begin before onset of mild cognitive impairment.

In certain embodiments, a treatment regimen can be used as a prophylactic or preventative measure. For example, in certain embodiments, a treatment regimen is administered to an elderly person, e.g., age 65 or older. In another embodiment, demographic data available in the art may be consulted to determine the average age of onset of Alzheimer's disease in a population of interest.

In a specific embodiment, a pharmaceutical composition of the invention is administered chronically, e.g., daily. In one embodiment, a pharmaceutical composition, e.g., a blood-brain permeable version of the mesylate salt of STI-571 (or its mesylate salt) is administered daily via oral administration, with a minimum of 10 µg/day and a maximum of 800 µg/day administered.

5.1.2.5. Routes of Administration

The component or components of a therapeutic composition of the invention may be introduced parenterally, topically, or transmucosally, e.g., orally, nasally, or rectally, or transdermally. In certain embodiments, administration is parenteral, e.g., via intravenous injection, and also including, but not limited to, intra-arteriole, intramuscular, intradermal, subcutaneous, intraperitoneal, intraventricular, and intracranial administration. In certain embodiments, the component or components of a therapeutic composition of the invention is introduced by intrathecal administration via osmotic pumps (e.g., a refillable osmotic pump), by oral gavage, or by intraperiotoneal injection.

In preferred embodiments of the invention, an agent (or drug or compound) can cross and more preferably, readily pass through the blood-brain barrier, which permits, e.g., oral, parenteral or intravenous administration. Alternatively, the agent can be modified or otherwise altered so that it can cross or be transported across the blood brain barrier. Many strategies known in the art are available for molecules crossing the blood-brain barrier, including but not limited to, increasing the hydrophobic nature of a molecule; introducing the molecule as a conjugate to a carrier, such as transferring, targeted to a receptor in the blood-brain barrier, or to docosahexaenoic acid etc.

In a specific embodiment, the agent is delivered orally and can readily pass through the blood-brain barrier.

In another embodiment, an agent of the present invention is administered via the standard procedure of drilling a small hole in the skull to administer the agent.

In other embodiments, the molecule can be administered intracranially or intraventricularly. In another embodiment, osmotic disruption of the blood-brain barrier can be used to effect delivery of agent to the brain (Nilayer et al., 1995, Proc. Natl. Acad. Sci. USA 92:9829-9833). In yet another embodiment, an agent can be administered in a liposome targeted to the blood-brain barrier. Administration of pharmaceutical agents in liposomes is known (see Langer, 1990, Science 249:1527-1533; Treat et al., 1989, in Liposomes in the Therapy of infectious Disease and Cancer, Lopez-Berestein and Fidler (eds.), Liss, New York, pp. 317-327 and 353-365). All of such methods are envisioned in the present invention.

The rate and extent of entry of a compound into the brain are generally considered to be determined by partition coefficient, ionization constant(s), and molecular size. The octanol water system, for example, has received particular attention, and Hansch and coworkers have suggested that a partition coefficient in this system of about 100 is optimal for entry into the central nervous system (CNS) (Giave and Hansch, 1972, J. Pharm. Sci. 61:589; Hansch et al., 1987, J. Pharm. Sci. 76:663). The octanol-water partition system provides a qualitative indication of the capability of a compound to cross the blood-brain barrier. Other factors, besides the octanol-water partition can be manipulated to influence the propensity to cross the blood-brain barrier. For example, decreasing over-all hydrogen binding ability of a compound can be used to facilitate a compound's crossing of the blood-brain barrier. Further, methodology as used by Begley et al. can be used and includes: (1) measuring the brain uptake index (BUI) with the equation for a tritiated agent compound:

$$BUI=[(brain\ ^3H/brain\ ^{14}C)/(injectate\ ^3H/injectate\ ^{14}C)]\times 100$$

where the $^{14}C$ reference compound is $^{14}C$ butanol or an analogous solvent; (2) Brain perfusion studies; (3) Intravenous bolus injection studies; and (4) Studies with cultured cerebral capillary endothelium.

In another embodiment used to reduce systemic side effects, the therapeutic compound is delivered in a vesicle, in particular a liposome (see Langer, 1990, Science 249:1527-1533; Treat et al., 1989, in Liposomes in the Therapy of Infectious Disease and Cancer, Lopez-Berestein and Fidler (eds.), Liss: New York, pp. 317-327 and 353-365).

In another embodiment, the therapeutic compound can be delivered in a controlled release system. For example, the agent may be administered using intravenous infusion, an implantable osmotic pump, a transdermal patch, liposomes, or other modes of administration. In one embodiment, a pump may be used (see Langer, 1990, Science 249:1527-1533; Sefton, 1987, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used (see Medical Applications of Controlled Release, Langer and Wise (eds.), 1974, $CR^c$ Press: Boca Raton, Fla.; Controlled Drug Bioavailability, Drug Product Design and Performance, Smolen and Ball (eds.), 1984, Wiley: New York; Ranger and Peppas, 1983, J. Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105). In yet another embodiment, a controlled release system can be placed in proximity of the therapeutic target, i.e., the brain, thus requiring only a fraction of the systemic dose (see, e.g., Goodson, 1984, in Medical Applications of Controlled Release, supra, vol. 2, pp. 115-138). Other controlled release systems are discussed in the review by Langer (1990, Science 249:1527-1533).

5.2. Methods for Screening for Compounds that Modulate Aβ Levels

The present invention provides, in vivo, in situ, and in vitro, methods of identifying an agent, drug or compound for modulating Aβ levels exhibited by a cell or tissue. In certain embodiments, the agent has the ability to either stimulate or inhibit Aβ levels through modulation of the activity of γ-secretase. In one embodiment, the γ-secretase activity is ATP-dependent γ-secretase activity.

In one aspect, the method comprises identifying an agent to be tested for an ability to treat a disorder, including, but not limited to, an Aβ-related disorder. Such methods can be used alone or in conjunction with each other.

In certain embodiments, the invention provides methods of identifying an agent, drug or compound that modulate ATP-dependent Aβ peptide production and/or levels of Aβ in cells and tissues.

In certain embodiments, the invention provides methods of identifying an agent, drug or compound for modulating γ-secretase activity based on the determination of γ-secretase activity both before and after treatment of an ATP-dependent Aβ generating system with the compound to be tested. Such a system can be established from either broken cells (Xu et al., 1997, Proc. Natl. Acad. Sci. USA 94: 3748-3752) or isolated membranes (Zhang et al., 2001, Biochemistry 40: 5049-5055).

The invention also provides method of identifying a compound that modulates Aβ levels exhibited by a cell or tissue comprising:
(a) determining a first level of γ-secretase activity in said cell or tissue;
(b) contacting said cell or tissue with a test compound; and
(c) determining a second level of γ-secretase activity in said cell or tissue,
wherein a difference in said first level and said second level of γ-secretase activity is indicative of the ability of said test compound to modulate Aβ levels.

In one embodiment, the difference in γ-secretase activity is indicative of the ability of said test compound to modulate the Aβ levels. In another embodiment, Aβ levels are modulated. In another embodiment, the γ-secretase activity is an ATP-dependent enzymatic activity. In another embodiment, the γ-secretase activity is production of Aβ.

The invention also provides a method of identifying a compound that modulates Aβ levels exhibited by a cell or tissue comprising:
(a) contacting said cell or tissue with a test compound; and
(b) determining a level of activity of γ-secretase in said cell or tissue;
wherein a difference in said level and a control level of γ-secretase activity in a comparable cell or tissue not contacted with the test compound is indicative of the ability of said test compound to modulate Aβ levels.

In one embodiment, the difference in γ-secretase activity is indicative of the ability of said test compound to modulate the AD levels. In another embodiment, Aβ levels are modulated. In another embodiment, the γ-secretase activity is an ATP-dependent enzymatic activity. In another embodiment, the γ-secretase activity is production of Aβ.

The invention also provides a method for identifying an agent to be tested for an ability to treat an Aβ-related disorder in a patient in need of such treatment comprising:
(a) contacting in a cell or tissue γ-secretase with a potential agent; and
(b) detecting the amount of γ-secretase activity
wherein the agent is identified if a decrease in γ-secretase activity is detected in the presence of the potential agent and wherein the agent modulates Aβ levels.

In one embodiment, the ability to treat the Aβ-related disorder is tested. In another embodiment, the γ-secretase activity is an ATP-dependent enzymatic activity. In another embodiment, the γ-secretase activity is production of Aβ.

In another aspect, the invention provides a method for identifying an agent to be tested for an ability to modulate Aβ levels exhibited by a cell or tissue comprising:
(a) determining a first level of γ-secretase activity in said cell or tissue;
(b) contacting said cell or tissue with a potential agent; and
(c) determining a second level of γ-secretase activity in said cell or tissue,
wherein a difference in said first level and said second level of γ-secretase activity is indicative of the ability of said potential agent to modulate Aβ levels. In one embodiment, the method comprises the additional step of:

(d) determining whether the Aβ levels are modulated.

In another embodiment, the γ-secretase activity is an ATP-dependent enzymatic activity. In another embodiment, the γ-secretase activity is production of Aβ.

The invention also provides a method for identifying an agent to be tested for an ability to modulate Aβ levels exhibited by a cell or tissue comprising:
 (a) contacting said cell or tissue with a potential agent; and
 (b) determining a level of γ-secretase activity in said cell or tissue;
wherein a difference in said level and a control level of γ-secretase activity in a comparable cell or tissue not contacted with the test compound is indicative of the ability of said potential agent to modulate Aβ levels.

In one embodiment, the method comprises the additional step of:
 (c) determining whether the Aβ levels are modulated.

In another embodiment, the γ-secretase activity is an ATP-dependent enzymatic activity.

In another embodiment, the γ-secretase activity is production of Aβ.

The invention also provides a method for selecting a potential therapeutic agent for use in the treatment of an Aβ-related disorder comprising:
 (a) administering a potential therapeutic agent to an animal;
 (b) measuring the response of said animal to said potential therapeutic agent;
 (c) comparing the response of said animal with that of a control animal to which the potential therapeutic agent has not been administered; and
 (d) selecting a potential therapeutic agent based on the difference in responses observed between said animal and said control animal,
wherein the potential therapeutic agent modulates ATP-dependent γ-secretase activity.

In one embodiment, the animal is a guinea pig. In another embodiment, the disorder is Alzheimer's disease.

The invention also provides a method for selecting a potential therapeutic agent for use in the treatment of an Aβ-related disorder comprising:
 (a) administering a potential therapeutic agent to an animal;
 (b) measuring the response of said animal to administration of an agent that modulates activity of γ-secretase;
 (c) comparing the response of said animal with that of a control animal to which the potential therapeutic agent has not been administered; and
 (d) selecting a potential therapeutic agent based on the difference in responses observed between said animal and said control animal,
wherein the potential therapeutic agent modulates ATP-dependent γ-secretase activity.

In one embodiment, the animal is a guinea pig. In another embodiment, the disorder is Alzheimer's disease.

The invention also provides a method for selecting a potential therapeutic agent for use in the treatment of an Aβ-related disorder comprising:
 (a) administering a potential therapeutic agent to an animal;
 (b) measuring the response of said animal, wherein the response is selected from the group consisting of:
  (i) exhibition of behavior in a Morris water maze; and
  (i) exhibition of behavior in a Y-maze
 (c) comparing the response of said animal with that of a control animal to which the potential therapeutic agent has not been administered; and
 (d) selecting a potential therapeutic agent based on the difference in responses observed between said animal and said control animal,
wherein the potential therapeutic agent modulates Aβ levels.

In one embodiment, the animal is a guinea pig. In another embodiment, the disorder is Alzheimer's disease.

The invention also provides a method for preventing, delaying or reversing the progression of an Aβ-related disorder comprising:
 (a) identifying a mammal in need of prevention, delay, or reversal of the progression of the disorder; and
 (b) administering to said mammal an amount of an agent sufficient to modulate ATP-dependent γ-secretase activity,
wherein Aβ levels are modulated.

In one embodiment, the agent inhibits or decreases ATP-dependent γ-secretase activity.

In another embodiment, the mammal is human. In another embodiment, the disorder is Alzheimer's disease.

In another embodiment, the agent promotes or increases ATP-dependent γ-secretase activity.

In another embodiment, the agent is administered orally.

In another embodiment, the agent is administered with a NSAID. In specific embodiment, the NSAID is sulindac sulfide, flufenamic acid, ibuprofen, flurbiprofen, fenoprofen, mefenamic acid, indomethacin, carprofen, meclofenamic acid.

In another embodiment, the agent is administered with an antioxidant. In another embodiment, the antioxidant is selected from the group consisting of vitamin E, vitamin C, curcumin, and Gingko biloba.

In another embodiment, the agent the agent is administered with an acetylcholinesterase inhibitor.

According to the invention, a "control" level means a separate baseline level exhibited by a comparable cell or tissue not contacted with a test compound or a level that is exhibited by a cell or tissue prior to contacting it with a test compound. A control level can return to a known standard reference level.

As would be clearly understood by a person of ordinary skill in the art, any and/or all of the embodiments disclosed herein for identifying an agent, drug or compound that can modulate Aβ levels, including such procedures that incorporate rational drug design, as disclosed herein, can be combined to form additional drug screens and assays, all of which are contemplated by the present invention.

According to the methods of the invention, γ-secretase activity and/or Aβ level may be determined both before and after treatment of cells or tissues with a test compound.

One of skill would understand that according to the invention, once a compound is identified as capable of producing, e.g., γ-secretase activity and/or Aβ level similar to those produced by known ameliorative compounds, the compound may be used to treat an Aβ-related disorder. Such conditions would include, but not be limited to, Alzheimer's disease, Down's syndrome and inclusion body myositis. In the context of the present invention, the compounds identified would be administered as a sufficient dose or amount which can be determined by one of skill in the art based on data from studies such as presented in this specification. Such data would include, but not be limited to, results from IC50 determinations.

To determine whether a modulator is a selective ATP modulator, the skilled artisan would determine, using methods well known in the art, whether a candidate modulator discriminates among the molecules that affect ATP function in a cell of interest, and whether it only modulates a specific individual molecule, or class or subset of the molecules. For example, a compound may be assayed for activity in inhibiting a collection of various kinases, and would be recognized as a selective ATP modulator if it modulates ATP function in a related class of kinases. In certain embodiments, a battery of standard kinase assays is run to determine whether a modulator only modulates ATP function of a specific subset or class of kinases. In a specific embodiment, a standard luciferase (ATP-dependency) assay can be used. In certain embodiments, a non-specific ATP modulator will modulate luciferase production in the assay, whereas a specific inhibitor will not.

In other embodiments, a selective ATP modulator does not affect tau phosphorylation (see, e.g., U.S. Pat. No. 5,955,444) or Notch cleavage (see Section 10).

In one embodiment, the selectivity profile of the ATP modulator is similar or identical to that of STI-571 (or its mesylate salt, GLEEVEC™), STI-571 variant WGB-BC-15 or any of Compounds 1-5.

In certain embodiments, the modulator modulates an ATP-dependent cellular process, as disclosed herein. In other embodiments, however, it is contemplated that the modulator may modulate other energy-dependent (e.g., GTP-dependent) processes that utilize sources of energy other than ATP (e.g., GTP).

The present invention also provides in vivo methods of identifying agents that can modulate the level of Aβ via modulation of γ-secretase activity. Such methods can be employed alone or in conjunction with in vitro and in situ methods as disclosed herein.

According to the invention, in one embodiment of the invention, the skilled artisan would administer a modulator of Aβ levels, e.g., an ATP modulator or an inhibitor of γ-secretase activity, based on results of screening for levels of Aβ peptides produced in the presence and absence of the inhibitor. Such screening of compounds is routine to one of skill in the art (Durkin et al., 1999, J. Biol. Chem. 274 (29): 20499-20504; Petanceska and Gandy, 1999, J. Neurochem. 73: 2316-2320; De Strooper et al., 1999, Nature 398: 518-522; Vandermeerena et al., 2001, Neuroscience Letters 315: 145-148). Any compound identified as having selective γ-secretase inhibitory activity or to selectively inhibit Aβ production would be administered, e.g., in a pharmaceutically acceptable vehicle, to an animal, e.g., a human.

One such in vivo method comprises administering the agent to a non-human mammal. The amount (and/or rate) of activation of γ-secretase is then determined. An agent is identified as capable of modulating the level of Aβ, via modulation of γ-secretase activity, when the amount (and/or rate) of γ-secretase activation is increased or decreased in the presence of the agent relative to in the absence of the agent. In a specific embodiment, the γ-secretase activity is ATP-dependent γ-secretase activity. In one embodiment, the non-human mammal is a rodent, e.g., a wild-type guinea pig. In other embodiments, the non-human mammal is an animal model for a disease or disorder. Such animal models are disclosed herein.

In another embodiment, an experimental animal is used to ascertain the effect of a potential agent on a disorder, including but not limited to an Aβ-related disorder. A potential modulator that ameliorates the disorder can then be selected.

For example, in certain embodiments, a learning and/or memory behavioral response of an animal can be determined in the presence and absence of the agent. In specific embodiment, learning and/or memory behavioral response of the animal, e.g., a transgenic mouse such as a Tg2576 mouse. The Tg2576 transgenic mouse expresses human APP 695, develops the neuropathological signs of Alzheimer's disease, including amyloid plaques, and exhibits learning and memory deficits (Hsiao et al., 1996, Science 274, 99-102; U.S. Pat. No. 5,877,399). Another useful model is a transgenic mouse expressing human APP and a familial Alzheimer's disease gene ("human APP-Swedish") (Borchelt et al., 1996, Neuron 17:1005-1013). The learning and/or memory behavioral response of such an animal model can be measured using standard methods, e.g., a Y-maze or a Morris water maze (see, e.g., U.S. Pat. No. 5,877,399).

Methods of testing a potential therapeutic agent (e.g., a candidate drug, potential modulator, etc.) in animals or animal models are well known in the art. Thus potential therapeutic agents can be used to treat whole animals. The potential modulators can be administered by a variety of ways including topically, orally, subcutaneously, or intraperitoneally (such as by intraperitoneal injection) depending on the proposed use. Optimal dose will be empirically defined.

The potential efficacy of these compounds in relieving pathological symptoms of a disorder, including but not limited to, an Aβ-related disorder, can be assessed in animal models for disease. For example, in one embodiment, the animal model is a Tg2576, a transgenic mouse that expresses human APP 695. The Tg2576 mouse develops the neuropathological signs of Alzheimer's disease, including amyloid plaques, and exhibits learning and memory deficits (Hsiao et al., 1996, Science 274, 99-102; U.S. Pat. No. 5,877,399). Another useful model is a transgenic mouse expressing human APP and a familial Alzheimer's disease gene ("human APP-Swedish") (Borchelt et al., 1996, Neuron 17:1005-1013).

In certain embodiments of the invention, modulation of Aβ 1-40 levels is screened for. Aβ 1-40 is the major product of catabolism of APP by β-secretase and γ-secretase enzyme activities. The amino acid sequence of Aβ 1-40 corresponds to residues 597-636 of the 695 amino acid isotype of human APP:

```
                                        [SEQ ID NO: 1]
    Asp Ala Glu Phe Arg His Asp Ser Gly Tyr
    1

Glu Val His His Gln Lys Leu Val Phe Phe
    21

Ala Glu Asp Val Gly Ser Asn Lys Gly Ala
    31

Ile Ile Gly Leu Met Val Gly Gly Val Val.
```

In other embodiments, modulation of Aβ 1-42 level is screened for. Aβ 1-42 is a minor product of APP catabolism, typically produced at 10% the level of Aβ 1-40, that aggregates into fibrillar forms very rapidly. The amino acid sequence of Aβ 1-42 corresponds to residues 597-638 of human APP:

```
                                        [SEQ ID NO: 2]
    Asp Ala Glu Phe Arg His Asp Ser Gly Tyr
    11

Glu Val His His Gln Lys Leu Val Phe Phe
    21

Ala Glu Asp Val Gly Ser Asn Lys Gly Ala
    31

Ile Ile Gly Leu Met Val Gly Gly Val Val Ile Ala.
```

Models such as these can be used to assess the efficacy of any potential therapeutic agents as disclosed hereinbelow.

Generally, at least two groups of animals are used in the assay, with at least one group being a control group in which the administration vehicle is administered without the potential therapeutic agent.

Another aspect of the invention is a method for selecting a therapeutic agent for potential use in the treatment of disorder, including but not limited to an Aβ-related disorder, which comprises administering a suspected therapeutic agent to an animal model, and measuring and/or determining the putative therapeutic agent's effect on any of the phenotypic characteristics of the animal model, which may be believed to be related to said disorder.

Potential therapeutic agents are selected on the basis of whether there is a statistical significance between a test response and a normal (i.e., naive or control) response. Potential therapeutic agents are selected that show a statistically significant change in the characteristic measured/determined. In a preferred embodiment, the response of a control (or vehicle-treated) animal in the presence of a therapeutic agent is characteristically different from the response of a control (or vehicle-treated) animal to which the agent has not been administered.

A still further aspect of the invention is a method for selecting a therapeutic agent for possible use in the treatment of a disorder, including but not limited to an Aβ-related disorder, which comprises administering a suspected therapeutic agent to an animal model for a disorder and measuring and/or determining the putative therapeutic agent's effect on any of the phenotypic characteristics outlined above which may be believed to be related to said disorder.

In other embodiments, the agent is administered along with an antagonist. The amount (and/or rate) of modulation of γ-secretase activity is then determined. Since the administration of e.g., an antagonist, in the absence of the agent, should result in an increase in γ-secretase activity, an agent is identified as capable of modulating the activity of γ-secretase when the amount (and/or rate) of activation is significantly increased or decreased in the presence of the agent relative to in the absence of the agent.

In other embodiments, the agent is administered along with a nucleoside triphosphate. The amount (and/or rate) of modulation of γ-secretase activity is then determined. Since the administration of a nucleoside triphosphate, in the absence of the agent should result in a increase in γ-secretase activity, an agent is identified as capable of modulating the activity of γ-secretase when the amount (and/or rate) of activation is significantly increased or decreased in the presence of the agent relative to in the absence of the agent.

In certain embodiments, combinatorial libraries of chemical compounds, based on different structural skeletons (e.g., purines), as well as unrelated naturally occurring compounds, can be tested as drug candidates. In a preferred embodiment of this type, the assay is performed using high throughput technology with automated robotic technology as disclosed herein. Positive results ("hits") represent either the reduced or increased activity of γ-secretase, as compared to the control reactions (in which the drug candidate is not included in the assay).

Once a drug candidate is selected, structural variants of the drug candidate can be tested. These compounds can also be scrutinized and modified with parameters such as membrane permeability, specificity of effects, and toxicity. The selected (e.g., the most potent) compounds of this secondary screening can then be evaluated in situ and in animal models (see Section 9) to determine whether the selected compounds alter the activity of γ-secretase, and/or induce predicted behavioral alterations with minimal to no side-effects. Such behavioral abnormalities may include, but not be limited to, testing locomotor activity or learning and memory, as disclosed herein (see also, e.g., U.S. Pat. No. 5,877,399; and Kosten et al., J. Pharmacol., Exp. Ther. 269:137-144 (1994). In specific embodiments, methods for testing for learning and memory commonly known in the art, e.g., a Y-maze or a Morris water test can be used (see, e.g., U.S. Pat. No. 5,877,399).

These tests can be then be followed by human trials in clinical studies. Alternatively, in certain embodiments, human trials in clinical studies can be performed without animal testing. Compounds affecting targets other than γ-secretase can also be similarly screened, using alternative targets exemplified below.

Alternatively, modulators (e.g., activators or inhibitors) of γ-secretase activity can be obtained by screening, e.g., a random peptide library produced by recombinant bacteriophage (see, e.g., Scott and Smith, Science 249:386-390 (1990); Cwirla et al., 1990, Proc. Natl. Acad. Sci. USA 87:6378-6382; and Devlin et al., 1990, Science 249:404-406) or a chemical library. Using the "phage method" very large libraries can be constructed (106-108 chemical entities). A second approach may be to use chemical methods, of which the Geysen method (Geysen et al., 1986, Molecular Immunology 23:709-715; Geysen et al., 1987, J. Immunologic Method 102:259-274) and the method of Fodor et al. (1991, Science 251:767-773) are examples. Furka et al. (1988, 14th international Congress of Biochemistry, Volume 5, Abstract FR:013; Furka, 1991, Int. J. Peptide Protein Res. 37:487-493), Houghton (U.S. Pat. No. 4,631,211) and Rutter et al. (U.S. Pat. No. 5,010,175) disclose methods to produce a mixture of peptides. Such peptides can be tested as potential modulators of γ-secretase activity.

In another aspect, synthetic libraries (Needels et al., 1993, Proc. Natl. Acad. Sci. USA 90:10700-4; Ohlmeyer et al., 1993, Proc. Natl. Acad. Sci. USA 90:10922-10926; Lam et al., International Patent Publication No. WO 92/00252; Kocis et al., International Patent Publication No. WO 94/28028), and the like can be used to screen for modulators of γ-secretase activation, according to the present invention. Once a potential modulator is identified, chemical analogues can be either selected from a library of chemicals as are commercially available (e.g., from Chembridge Corporation, San Diego, Calif. or Evotec OAI, Abingdon, UK), or alternatively synthesized de novo. The prospective agent (drug) can be placed into any standard assay to test its effect on the activity of γ-secretase activation. A drug is then selected that modulates the activity of γ-secretase activation.

The present invention also contemplates screens for small molecules, analogs thereof, as well as screens for natural modulators of γ-secretase, such as those molecules that bind to and inhibit or activate, e.g., γ-secretase in vivo. Alternatively, natural products libraries can be screened using assays of the invention for molecules that modulate e.g., γ-secretase activity.

In another aspect of the present invention, a potential modulator can be assayed for its ability to modulate the level of Aβ, either independently, or subsequent to, a binding assay as disclosed herein. Such assays are known in the art. Thus, according to the methods of the invention, a modulator of γ-secretase activity that modulates the level of Aβ is then selected In another embodiment, a potential modulator can be added to a cultured cell line or tissue explant. Samples of the cells or tissues can be treated with various concentrations of a potential modulator and the samples can then be analyzed for Aβ levels. Potential modulators of Aβ levels can also be tested for example, on intact neurons in situ. The effects of these compounds can be tested by empirically defining the optimal concentration and time of incubation.

The present invention also includes compositions identified by the methods described herein. One of skill in the art would understand that once identified as capable of modulating Aβ levels in the method of the present invention, the compound of the invention could be used therapeutically to modulate Aβ levels in neuronal cells in order to treat conditions in which Aβ levels may be involved.

One of skill will understand that once identified as capable of modulating γ-secretase activity in the methods of the present invention, the compound may be used therapeutically to modulate γ-secretase activity in cells, e.g., neurons, in order to treat conditions in which γ-secretase activity may be involved. Such conditions include, but are not limited to, an Aβ-related disorder.

The present invention further provides methods for performing rational drug design to develop drugs that can modulate activity of γ-secretase and thereby ameliorate a disorder, including but not limited to an Aβ-related disorder. Such rational drug design can be performed using compounds that have been identified as inhibitors (or activators) of γ-secretase as a starting point. Thus, the present invention provides screens and assays to allow more specific inhibitors (or activators) to be identified. Such methods of rational drug design are well-known in the art. In a specific embodiment, the rational drug design methods disclosed in U.S. patent application Ser. No. 09/419,379, by Bibb et al., entitled "Methods of Identifying Agents That Regulate Phosphorylation/Dephosphorylation in Dopamine Signaling," filed Oct. 15, 1999, and Ser. No. 09/687,959, by Bibb et al., entitled "Methods of Identifying Agents That Regulate Phosphorylation/Dephosphorylation in Dopamine Signaling," filed Oct. 13, 2000, incorporated herein by reference in their entireties, are used.

Indeed, potential modulators can be examined through the use of computer modeling using a docking program such as GRAM, DOCK, or AUTODOCK (Dunbrack et al., 1997, Folding & Design 2:27-42), to identify compounds as potential modulators of an ATP-dependent enzymatic activity, e.g., ATP modulators such as those that modulate γ-secretase. These modulators can then be tested for their effect. In one embodiment, this procedure can include computer fitting of potential modulators to the γ-secretase complex to ascertain how well the shape and the chemical structure of the potential modulator will bind to γ-secretase (see, e.g., Bugg et al., 1993, Scientific American 269(6):92-98; West et al., 1995, TIPS, 16:67-74). Computer programs can also be employed to estimate the attraction, repulsion, and steric hindrance of the subunits with a modulator/inhibitor. Generally the tighter the fit, the lower the steric hindrances, and the greater the attractive forces, the more potent the potential modulator since these properties are consistent with a tighter binding constant. Furthermore, the more specificity in the design of a potential drug the more likely that the drug will not interact as well with other proteins. This will minimize potential side-effects due to unwanted interactions with other proteins.

Initially, in one embodiment, compounds known to bind to γ-secretase on any molecule that regulates γ-secretase activity or affects an enzyme complex that contain γ-secretase can be systematically modified by computer modeling programs until one or more promising potential analogs are identified. In addition systematic modification of selected analogs can then be systematically modified by computer modeling programs until one or more potential analogs are identified. Such analyses are well known to those of skill in the art and have been shown to be effective in the development of, e.g., HIV protease inhibitors (see, e.g., Lam et al., 1994, Science 263:

380-384; Wlodawer et al., 1993, Ann. Rev. Biochem. 62:543-585; Appelt, 1993, Perspectives in Drug Discovery and Design 1:23-48; Erickson, 1993, Perspectives in Drug Discovery and Design 1: 109-128).

Any of the potential agents or targets for the potential agents (e.g., γ-secretase, Aβ, kinases, ATP) can be labeled. Suitable labels include enzymes (e.g., alkaline phosphatase or horseradish peroxidase), fluorophores (e.g., fluorescein isothiocyanate (FITC), phycoerythrin (PE), Texas red (TR), rhodamine, free or chelated lanthamide series salts, especially Eu3+, to name a few fluorophores), chromophores, radioisotopes, chelating agents, dyes, colloidal gold, latex particles, ligands (e.g., biotin), chemiluminescent agents, magnetic beads or magnetic resonance imaging labels. When a control marker is employed, the same or different labels may be used for the receptor and control marker.

In embodiments wherein a radioactive label, such as the isotopes $^{3}$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re is used, standard counting procedures known in the art may be utilized.

In embodiments wherein the label is an enzyme, detection may be accomplished by any of the presently utilized colorimetric, spectrophotometric, fluorospectrophotometric, amperometric or gasometric techniques known in the art.

A direct label is an example of a label that can be used according to the methods of the present invention. A direct label is an entity that, in its natural state, is readily visible, either to the naked eye (for example, by visual inspection through a compound or dissecting light microscope), or with the aid of an optical filter and/or applied stimulation, e.g., U.V. light to promote fluorescence. Examples of colored labels that can be used according to the methods of the present invention, include metallic sol particles, for example, gold sol particles such as those disclosed by Leuvering (U.S. Pat. No. 4,313,734); dye sol particles such as disclosed by Gribnau et al. (U.S. Pat. No. 4,373,932) and May et al. (WO 88/08534); dyed latex such as disclosed by May et al. (WO 88/08534), Snyder (EP-A 0280 559 and 0 281 327); or dyes encapsulated in liposomes as disclosed by Campbell et al. (U.S. Pat. No. 4,703,017).

Other direct labels include a radionucleotide, a luminescent moiety, or a fluorescent moiety including, but not limited, to, e.g., a modified/fusion chimera of green fluorescent protein (as disclosed in U.S. Pat. No. 5,625,048, issued Apr. 29, 1997, and WO 97/26333, published Jul. 24, 1997, each of which is incorporated herein by reference in its entirety).

In addition to these direct labeling devices, indirect labels comprising enzymes can also be used according to the present invention. Various types of enzyme-linked immunoassays are well known in the art, for example, enzyme-linked immunoassays using alkaline phosphatase, horseradish peroxidase, lysozyme, glucose-6-phosphate dehydrogenase, lactate dehydrogenase, or urease. These and other similar assays are well known in the art and are disclosed, e.g., in Engvall (1980, "Enzyme Immunoassay ELISA and EMIT," in Methods in Enzymology, 70: 419-439) and in U.S. Pat. No. 4,857,453.

In certain embodiments, proteins can be labeled by metabolic labeling. Metabolic labeling occurs during in vitro incubation of the cells that express the protein in the presence of culture medium supplemented with a metabolic label, such as [$^{35}$S]-methionine or [$^{32}$P]-orthophosphate. In addition to metabolic (or biosynthetic) labeling with [Cl$_{2}$]-methionine, the invention further contemplates labeling with [$^{14}$C]-amino acids and [$^{3}$H]-amino acids (with the tritium substituted at non-labile positions) (see, e.g., U.S. patent application Ser. No. 09/419,379, by Bibb et al., entitled "Methods of Identifying Agents That Regulate Phosphorylation/Dephosphorylation in Dopamine Signaling," filed Oct. 15, 1999, and Ser. No. 09/687,959, by Bibb et al., entitled "Methods of Identifying Agents That Regulate Phosphorylation/Dephosphorylation in Dopamine Signaling," filed Oct. 13, 2000, incorporated herein by reference in their entireties).

5.2.1. Assays for γ-Secretase Activity

According to the methods of the invention, modulators (e.g., inhibitors or activators) of γ-secretase, can be detected and isolated using methods commonly known in the art, and/or identified by direct assay of isolated enzyme. Such assays are well known to those of skill in the art.

In one embodiment, the methods of Roberts et al. (U.S. Patent Application 20020025540, published Feb. 28, 2002, entitled "Isolation of functionally active gamma-secretase protein complex and methods for detection of activity and inhibitors thereof") are used.

In another embodiment, the methods of Zhang et al. (2001, Biochemistry 40: 5049-5055) are used.

In another embodiment, γ-secretase activity may be assayed according to the methods known in the art, e.g., the methods of De Strooper et al., 1999, Nature 398: 518-522.; Hsiao et al., 1996, Science 274: 99-102.; Li et al., 2000, Proc. Natl. Acad. Sci. USA 97: 6138-6143.; Lichtenthaler et al., 1999, FEBS Lett. 453: 288-292; McLendon et al., 2000; FASEB J. 14: 2383-2386; or Seiffert et al., 2000, Brain. Res. Mol. Brain Res. 84: 115-126.

In another embodiment, γ-secretase activity may be assayed according to the methods that assay for cleavage of proteins other than APP or APP-like proteins. For example, proteolytic cleavage of the Notch protein, which is a single transmembrane domain cell surface receptor that mediates many cell fate decisions in vertebrates and invertebrates (Artavanis-Tsakonas et al., 1996, Science 268:225-232; Kopan and Turner, 1996, Curr. Opin. Neurobiol. 6:594-601; Weinmaster, 1997, Mol. Cell. Neurosci. 9:91-102) may be assayed using the methods of Ray et al. (1999, J. Biol. Chem. 274: 36801-36807) or Schroeter et al. (1998, Nature 393:382-386), which are incorporated herein by reference in their entireties.

γ-secretase may be immunoprecipitated from brain homogenate using standard methods, using, e.g., a commercial antibody directed against γ-secretase.

In yet another embodiment, γ-secretase activity is assayed according to the methods disclosed hereinbelow, e.g. in Example 4.

5.2.2. Assays for Aβ Levels

Aβ levels may be determined according to any method known in the art. In one embodiment, Aβ levels are determined according to the methods of Xu et al. (1997, Proc. Natl. Acad. Sci. USA 94: 3748-3752).

In other embodiments, Aβ levels are determined according to the methods disclosed hereinbelow, e.g., in Examples 1, 2 or 3.

In another embodiment, Aβ peptide may be assayed for, e.g., in a brain homogenate, using a sandwich ELISA (e.g., Biosource International, Camarillo, Calif.) according the manufacturer's recommendations.

5.2.3. Animal Models

In vivo animal models of APP processing into Aβ and of Aβ-related disorders such as Alzheimer's disease are well known to those of skill in the art. Such animal models can, for example, be used to further screen compounds identified via the methods presented herein. Alternatively, such models can be used to routinely validate compounds for efficacy in use in the modulation, prevention, treatment, and symptom amelioration methods of the present invention.

In one embodiment, the wild-type guinea pig is used as an animal model. For example, wild-type guinea pigs may be used as models for APP processing into Aβ, for Aβ production and/or accumulation of Aβ in brain. They are known to produce Aβ peptides that are immunologically identical to human Aβ. Therefore, the guinea pigs provide, for example, a model in which to examine perturbations in APP metabolism with and without drug treatment.

In other embodiments, a mouse model of Alzheimer's disease is used, e.g., a transgenic mouse expressing human APP-Swedish (see, e.g., Borchelt et al., 1996, Neuron 17:1005-1013), which exhibits neuropathological symptoms similar to those of Alzheimer's disease patients. Moreover, a rat model of Alzheimer's disease can be used. In another embodiment, a transgenic mouse model of Alzheimer's disease can be used, e.g., the Tg2576 transgenic mouse (U.S. Pat. No. 5,877, 399). Such an animal model may be used to screen for compounds useful in the treatment of Alzheimer's disease due to its exhibition of, e.g., an altered level of human Aβ.

Models such as these can also be used to assess the efficacy of any potential therapeutic agents as disclosed hereinbelow. Generally, at least two groups of animals are used in the assay, with at least one group being a control group in which the administration vehicle is administered without the potential therapeutic agent.

According to the invention, animal models may be employed that have, in certain embodiments, an altered physiological regulation of the nervous system such that the animal or tissues derived from it can be utilized for screening of potential therapeutic agents and/or therapeutic regimens that act at the level of γ-secretase activity, especially at the level of competing (directly or indirectly) with ATP for activation of γ-secretase. Drugs that can reverse any of the defects exhibited by such an animal model act at some point in the catabolic pathway underlying the cleavage of APP to Aβ, and are thus of potential use therapeutically. Additionally, since some defects occur at the behavioral level, the alteration or modulation of these behavioral defects can have a high predictive value for therapeutic use in modification of such behaviors.

According to the methods of the invention, animal models thus can be used, as screening tools to elucidate the mechanisms of APP cleavage to Aβ involved in both normal and diseased patient populations. For example, an animal model can thus be utilized to assess the response to a variety of potential therapeutic strategies and therapeutic agents that can thus be used in the treatment of patients suffering from a variety of neurological diseases and disturbances.

Using animal models, various small molecule drugs can be screened for potentially advantageous effects, including enhanced potency as well as minimization of side effects. Typical candidates for such screening may be obtained from any of several commercially available drug libraries.

Specific disorders for which an animal model can be utilized include, but are not limited to, an Aβ-related disorders, as disclosed herein. By measuring various characteristics in an animal model in response to administration of endogenous or exogenous agents, and comparing these characteristics to those in an animal treated with a potential therapeutic agent, an assessment of the utility of the potential therapeutic agent in the prevention and/or treatment of a particular disorder or disease state can be made. For instance, the potential therapeutic agent can be administered to an animal model for a particular Aβ-related disorder, and the Aβ level in a control animal (e.g., an animal administered vehicle) can then provide an indication of the value of the potential therapeutic agent.

Another aspect of the invention is a method for selecting a therapeutic agent for possible use in the treatment of a disorder, including but not limited to, an Aβ-related disorder, which comprises administering a suspected therapeutic agent to an animal model, and measuring and/or determining the putative therapeutic agent's effect on any phenotypic characteristics which may be believed to be related to said disorder.

In one embodiment of this aspect of the invention, a suspected therapeutic agent is administered to an animal model, e.g., an animal model for an Aβ-related disorder, and the Aβ level is measured for the animal model, wherein the normal Aβ level of the animal model in the absence of a therapeutic agent is characteristically different than that of control (e.g., wild-type) animals. The potential therapeutic agents are selected on the basis of whether there is a statistical significance between a test characteristic, e.g., a test Aβ level and a normal characteristic, e.g., a normal Aβ level. Potential therapeutic agents are selected that show a statistically significant change in the characteristic that is measured or determined. In a preferred embodiment, the test characteristic of the animal model in the absence of a therapeutic agent is different than that of control (e.g., wild-type) animals to which the potential therapeutic has not been administered.

Yet another aspect of the present invention is a method for selecting a therapeutic agent for possible use in the treatment of Alzheimer's disease which comprises administering a suspected therapeutic agent to an animal model, e.g., an animal model for Alzheimer's disease, and measuring and/or determining the putative therapeutic agent's effect on any of the phenotypic characteristics which may be believed to be related to Alzheimer's disease.

The following experimental examples are offered by way of illustration and not by way of limitation.

6. EXAMPLE 1

Production of Aβ is ATP-Dependent

The working example presented herein demonstrates that production of Aβ is ATP-dependent, and presents data indicating that p-secretase activity is at least partially ATP-independent, while optimal γ-secretase activity requires ATP.

6.1. Materials and Methods

Whole N2a cells doubly transfected with the human Swedish APP mutation and the presenilin-1 (PS 1) mutant, ΔE9, were $^{5}$S-pulse-labeled before permeabilization and chased at 20° C. to localize newly synthesized, $^{35}$S-labeled APP to the Golgi apparatus, a major location for APP and the predominant site of Aβ production. Cells were then permeabilized according to the methods of Xu et al. (1997, Proc. Natl. Acad. Sci. USA 94: 3748-3752), depleted of cytosol and incubated at 37° C. either with an ATP regenerating system or with apyrase to hydrolyze residual ATP and other nucleotide triphosphates, and Aβ production was assayed. The effect of adding an ATP-regenerating system to a cell-free assay system for Aβ generation was quantitated according to the methods of Xu et al. (1997, Proc. Natl. Acad. Sci. USA 94: 3748-3752).

For the assay of isolated γ-secretase activity, membranes were isolated from N2a cells expressing a recombinant γ-secretase substrate, C99, according to the methods of Zhang et al. (2001, Biochemistry 40: 5049-5055). Accumulation of human C99 (also known as β C-terminal fragment or βCTF) in this system results from expression of the transgene and not from endogenous BACE (β-secretase) cleavage of mouse APP; furthermore, the use of human specific anti-Aβ antibody does not effectively resolve the small amount of endogenous mouse Aβ produced under the experimental conditions, thus, allowing measurement of only Aβ produced from the action of γ-secretase on the human C99. Also, to determine whether ATP was primarily responsible for stimulating γ-secretase activity, the previous energy regenerating system was substituted with one designed to sustain concentrations of ATP alone but not GTP. Aβ release from isolated membranes was determined by ELISA (Biosource International, Camarillo, Calif.).

6.2. Results

Studies were performed to examine possible energy requirements of Aβ production. Aβ production was reconstituted in a cell-free system consisting of permeabilized cells, the cytosol of which had been washed away, leaving intracellular membranes and organelles intact.

To identify steps in the APP processing pathway that might require ATP, accumulation of APP metabolites was studied using $^{35}$S pulse labeling in a cell-free system consisting of N2a cells doubly transfected with the human Swedish APP mutation and the presenilin-1 (PS 1) mutant, ΔE9. Both mutations result in familial forms of Alzheimer's disease characterized by a higher Aβ42/Aβ40 ratio (Borchelt et al., 1996, Neuron 17:1005-1013). This cell line has been shown to produce large amounts of Aβ peptides and of C99, a product of β-secretase cleavage of APP and an immediate precursor of Aβ. The responses of both β-secretase and γ-secretase activities to ATP depletion were measured and compared.

Figure 1:
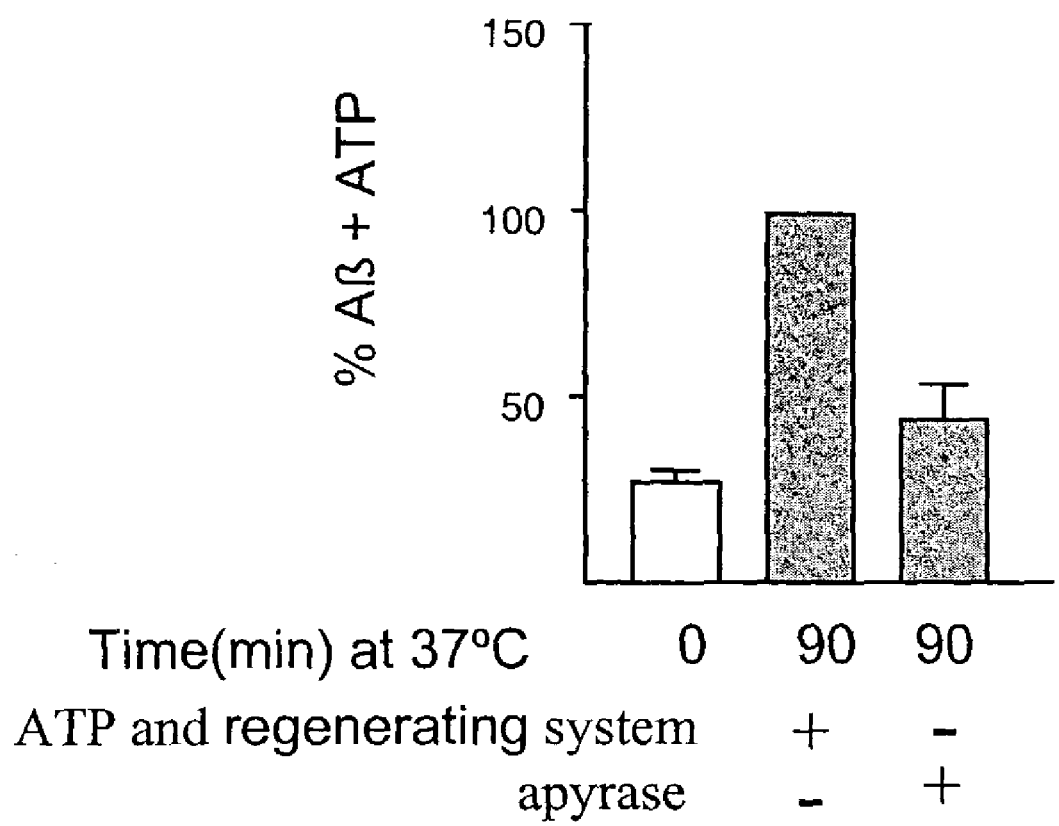
FIG. 1 is a bar graph quantitating the effect of adding an ATP-regenerating system to a cell-free assay system for Aβ generation. The system is derived from mouse N2a cells expressing both the Swedish variant of human APP and the presenilin-1 (PS1) mutation.
Figure 2:
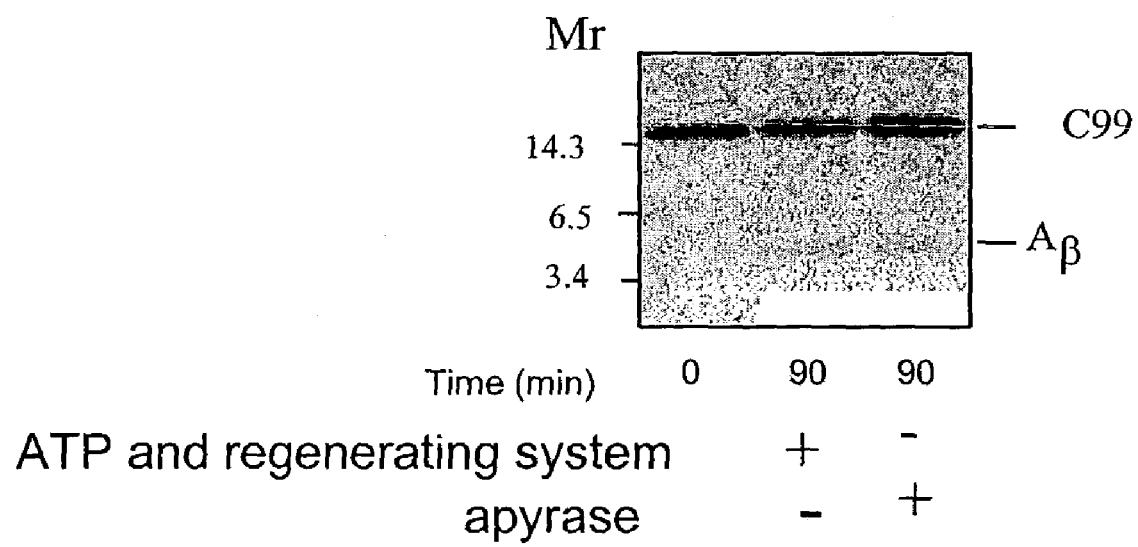
FIG. 2 is an autoradiogram showing that the β-secretase cleavage product, C99 (also known as βCTF), accumulates in an ATP-depleted cell free system.

ATP stimulated Aβ production above the initial level of Aβ that had accumulated during the 20° C. chase. The results of these experiments, showing radiolabeled Aβ production from precursor accumulated in the Golgi apparatus, are shown in FIG. 1. In particular, the energy regenerating system resulted in a three-fold increase in Aβ production compared to apyrase treated samples (FIG. 1) and concomitantly, a two-thirds decrease in C99 (also known as β C-terminal fragment or βCTF) (FIG. 2).

A much smaller quantity of Aβ was produced in the absence of ATP, demonstrating that production of Aβ is ATP-dependent.

By contrast, C99 production from APP was increased in the absence of ATP, indicating that the activity of β-secretase is at least partially ATP-independent. This result also indicates that the increase in C99 likely results from a decrease in γ-secretase activity, that allows for accumulation of the Aβ precursor. This is evident in the autoradiogram shown in FIG. 2.

Virtually, identical results were achieved when apyrase was left out and samples were incubated in the absence of the energy regenerating system (data not shown).

These results indicate that, in the context of Aβ production, optimal γ-secretase activity requires nucleotide triphosphates and that substantial β site APP cleaving enzyme (also known as β-secretase or "BACE") activity still occurs in their absence.

Figure 3:
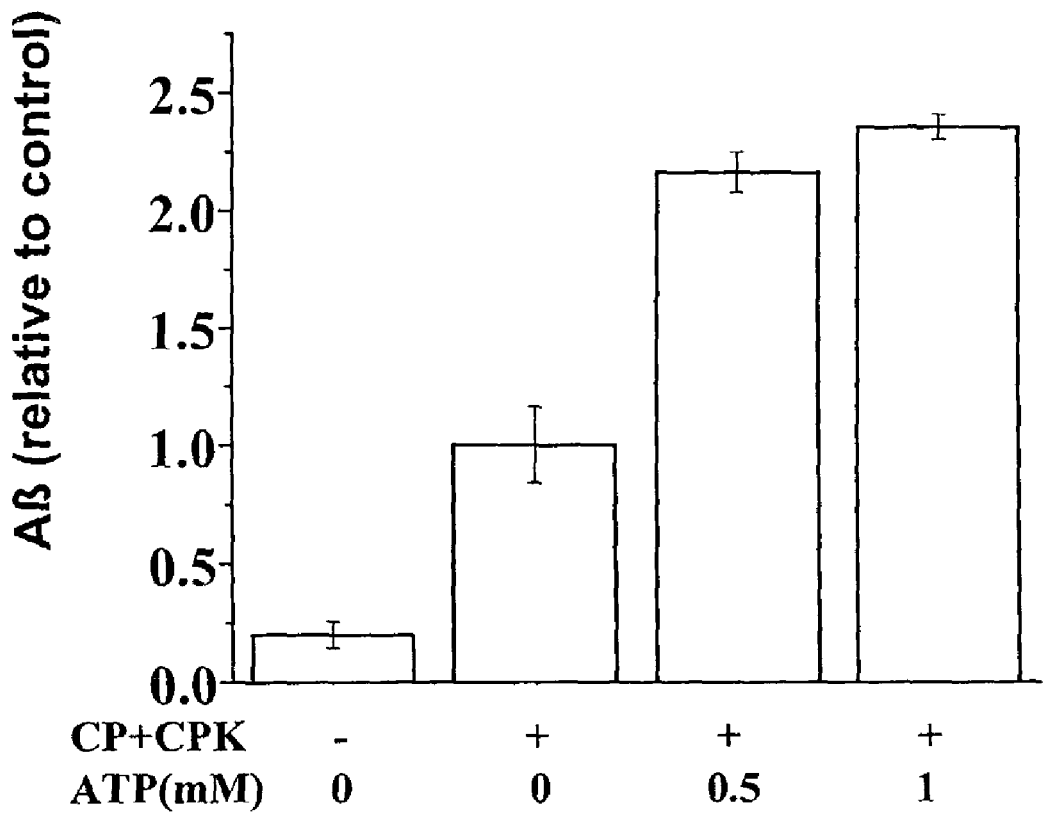
FIG. 3 is a bar graph showing strong ATP-dependence of C99 cleavage to Aβ in isolated membranes.
Figure 4:
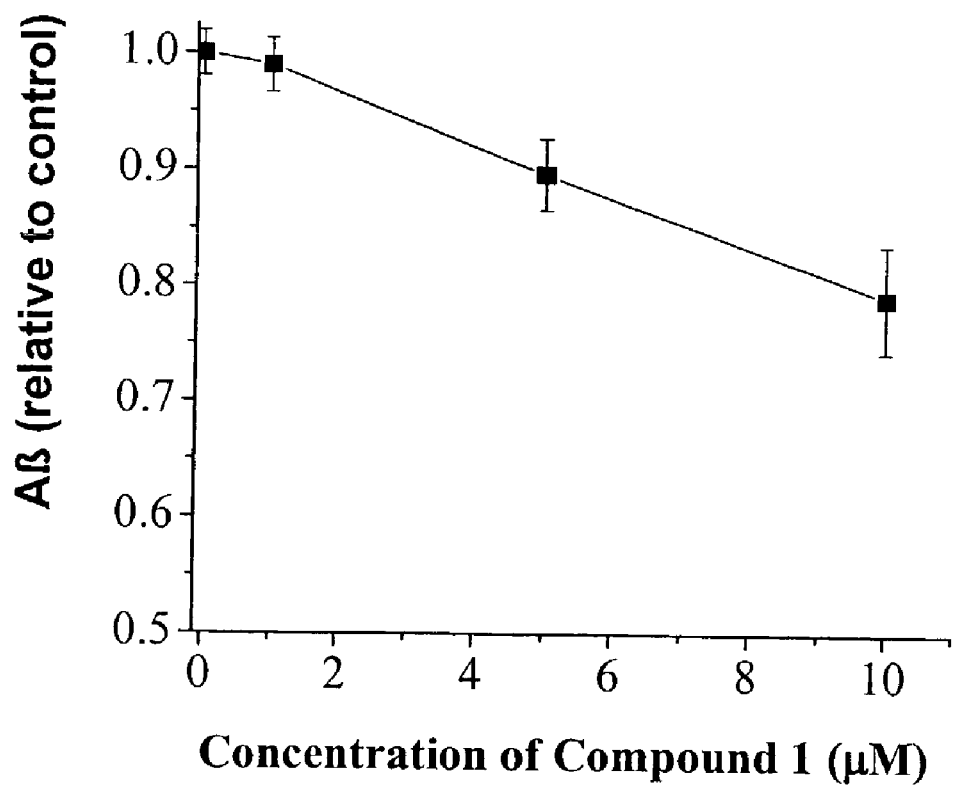
FIG. 4 is a graph of the dose-response for reduction of Aβ levels in isolated membranes by Compound 1.

In order to test whether isolated γ-secretase activity is ATP-dependent, an assay of isolated γ-secretase activity was performed. Generation of Aβ in the isolated γ-secretase assay was strongly stimulated by addition of ATP and a regenerating system (Xu et al., 1997, Proc. Natl. Acad. Sci. USA 94: 3748-3752) (FIG. 3). A dose-dependent decrease in Aβ generation was observed upon addition of Compound 1 (see below) to these membranes (FIG. 4).

In summary, the results presented herein demonstrate that production of Aβ is ATP-dependent. The results further indicate that β-secretase activity is at least partially ATP-independent, and optimal γ-secretase activity requires ATP.

7. EXAMPLE 2

Modulation of Aβ Levels

The working example presented herein demonstrates the successful use of compounds to modulate, in particular lower, Aβ levels.

7.1. Materials and Methods

N2a cells transfected with the human Swedish APP mutation, and with either normal human presenilin 1 or ΔE9 mutant presenilin 1 (PS1), were used for assays of compound effect on Aβ generation.

Media was added with compound concentration of 0, $10^{-9}$, $10^{-8}$, $10^{-7}$ and $10^{-6}$ M; cells were incubated overnight at 37° C. The next day, cells were incubated with $^{35}$S-methionine and $^{35}$S-cysteine for four hours in the presence of the compound as above.

Media and cells were separately harvested and subjected to immunoprecipitation with antibody 4G8 (Senetek, Napa, Calif.), which recognizes an epitope corresponding to residues 17-28 of Aβ. Antibody 4G8 immunoprecipitates Aβ from media, and Aβ plus full-length APP from cells. After removal of antibody 4G8 and bound Aβ from media, the supernatant was reacted with 22C11 (Chemicon International), an antibody that immunoprecipitates sAPPβ and sAPPα. Immunoprecipitates were subjected to PAGE and resolved by autoradiography according to standard methods. APP metabolites were compared by densitometry according to standard methods.

In other experiments, immunoprecipitation followed by Western blot analysis was carried out on unlabeled (no radioactive label) N2a cells, using standard methods and using 6E10 (Senetek, Napa, Calif.) or 22C11 antibodies for detection.

Mass spectrometry was carried out on media from N2a cells to detect Aβ40 and Aβ42 peptides using the Ciphergen-ProteinChip System (Ciphergen Biosystems Inc., Fremont, Calif.), which is based on Seldi and time-of-flight mass spectrometry, using standard protocols as set out by the manufacturer. The experimental procedures were the same as those disclosed above for immunoprecipitation/Western blotting, without metabolic labeling. Unlike immunoprecipitation/Western blotting, media did not contain sodium lauryl sulfate (SDS) but did contain Triton X-100 detergent. Aliquots of detergent treated media were contacted to a metal chip that was previously contacted with an antibody, such as 6E10. The antibody binds human APP metabolites, including Aβ, in the applied sample. Detection of bound antigen followed a laser pulse that dissociated antigen from antibody.

Aβ peptides were resolved graphically as peaks of various heights, situated on an x-axis denoting molecular mass. Thus, Aβ40 and Aβ42 were resolved separately at approximately 4333 and 4519 daltons, respectively. The relative heights or areas under the peaks in a given spectrum denoted the relative concentrations of the detected species. Peaks corresponding to the same species, as conveyed by molecular mass, were compared among different spectra, reflecting different samples, to measure relative quantities of Aβ among a set of samples.

These immunoprecipitation experiments were repeated using a minimal treatment time, 1 hour instead of overnight.

7.2. Results

Compounds were tested for an ability to modulate Aβ levels. In particular, STI-571, a member of the phenyl aminopyrimidine class of pharmacophores was tested. Specifically, the mesylate salt of STI-571 (also known as GLEEVEC™, Novartis; see FIG. 20) was tested. STI-571 is an ATP competitor known to target the ATP binding site on BCR-Abl tyrosine kinase, and also to inhibit Abl, c-kit and platelet-derived growth factor receptor (PDGFR). An STI-571 variant, WGB-BC-15 (see FIG. 20), was also tested. In addition, Compounds 1 and 2 (see FIG. 20), members of the pyrimidinyl pyridone tyrosine kinase inhibitor class of molecules, were tested.

At concentrations in the range of $1 \times 10^{-6}$ M, STI-571 exhibited an IC50 (that is, inhibited total levels of Aβ by 50%) in N2a cells expressing APP and either normal human presenilin 1 or ΔE9 mutant presenilin 1. WGB-BC-15 also inhibited levels of secreted Aβ. Compound 1 inhibited total Aβ levels as well, with an IC50 of less than $10^{-6}$ M.

Intracellular levels of Aβ also decreased in the presence of the compounds. These results were derived from immunoprecipitation/Western blot analysis and corroborated by results of studies on APP incorporation of $^{35}$S-methionine.

Levels of sAPPα and sAPPβ, two of the major secreted metabolites of APP, were not inhibited by these compounds. Levels of sAPPα increased at higher concentrations of the compounds. These results demonstrate that the reduction observed in secreted Aβ levels was not due to some non-specific deleterious affect on the cells' protein secretion ability.

Figure 5:
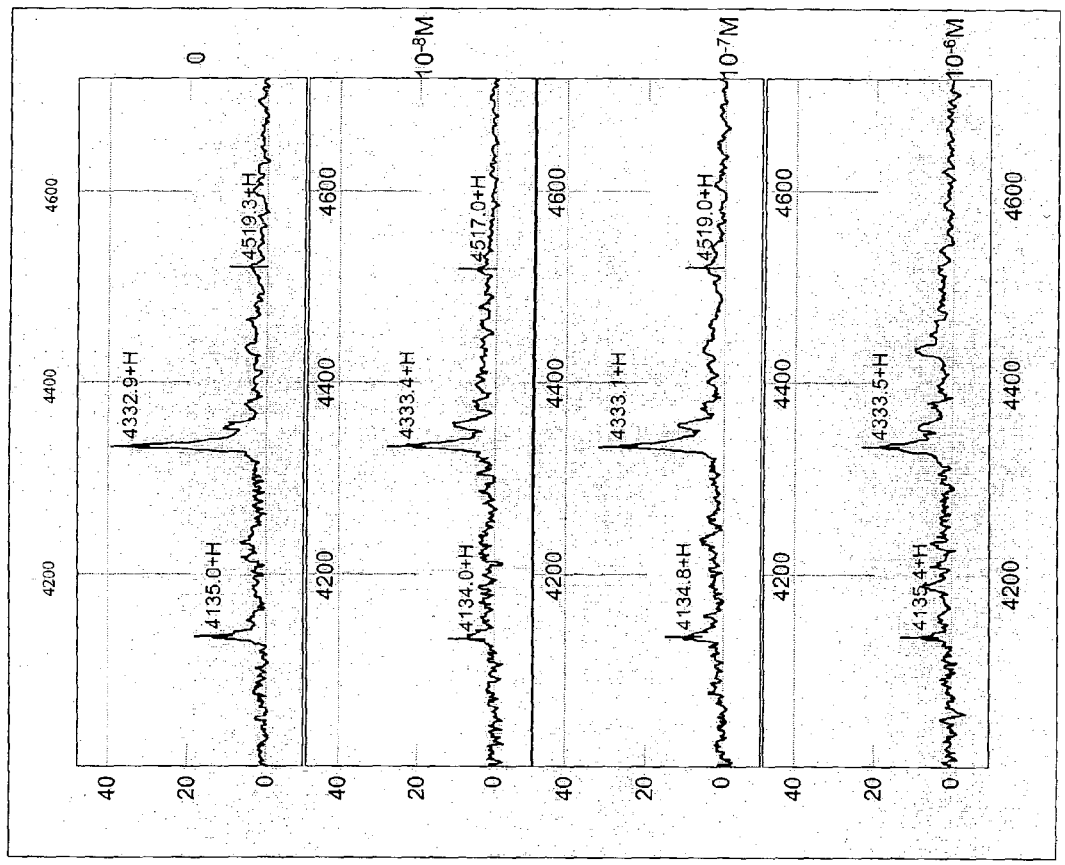
FIG. 5 is a mass spectrographic profile of peptides immunoprecipitated from the supernatant of N2a cells, expressing both the Swedish variant of human APP and the presenilin-1 (PS 1) mutation, with anti-Aβ antibody 6E 10 (Senetek, Napa, Calif.), showing decreased Aβ40 ("Aβ 1-40") and Aβ42 ("Aβ1-42") in the presence of Compound 1. Y-axis, concentration of Compound 1 (M).

Mass spectrometry was carried out according to standard methods, by which Aβ40 and Aβ42 were clearly resolved, revealing that levels of both species were dramatically reduced in the presence of Compound 1 (FIG. 5).

FIGS. 6 and 7 illustrate the dose-dependent decrease in Aβ observed after just one hour of treatment of $^{35}$S labeled N2a cells expressing the human APP-Swedish transgene with STI-571 or Compound 1, respectively.

8. EXAMPLE 3

Modulation of Aβ Levels in Primary Neuronal Cell Cultures

This example demonstrates that STI-571, Compound 1 and Compound 2 inhibit production of Aβ peptides in normal rat primary neuronal cell cultures. These result correlate well with the in vivo results described below (see Section 9).

8.1. Materials and Methods

Cultures of rat embryonic cortical neurons were established from day 18 pregnant SD rats using standard techniques (Gasparini et al., 2001, J. Neurosci. 21(8):2561-2570). After several days of culture, new media was added along with STI-571, Compound 1 or Compound 2 at concentrations of 0, $10^{-9}$, $10^{-8}$, $10^{-7}$ $2 \times 10^{-6}$ and $10^{-6}$ M; cells were incubated overnight at 37° C.

The next day, cells were labeled with $^{35}$S-methionine and cysteine for four hours in the presence of compounds as above. Media and cells were then harvested and subjected to immunoprecipitation with antibody 4G8, to detect Aβ and APP. The media was serially immunoprecipitated first with antibody 4G8 and then antibody 22C11, for detection of secreted Aβ, sAPPβ and sAPPα. Immunoprecipitates were subjected to PAGE and resolved by autoradiography; APP metabolites were compared by densitometry.

8.2. Results

Results similar to those obtained in Example 2 were obtained in these experiments with rat cortical neurons exposed to Compound 1. Compound 1 reduced levels of Aβ in both media (FIG. 8A) and cells. The predominant Aβ peptide produced by the neurons was Aβ11-40, which is characteristic of rat primary neurons (FIG. 8B). Total sAPP was not reduced significantly nor was total cellular APP (FIG. 9), indicating that the compound was not cytotoxic nor did it non-specifically inhibit cellular secretion. Similar results were obtained with related Compound 2 (FIG. 10).

The time course and dose response of primary cortical neuronal cultures to STI-571 and Compound 1 were studied in more detail in a second set of experiments similar to those described above. Significant reductions in Aβ were observed in as little as 6 hours (FIGS. 11 and 12) and 5 μM STI-571 (FIG. 13) or 0.5 μM Compound 1 (FIG. 14).

9. EXAMPLE 4

Modulation of Aβ Levels in an Animal Model of Aβ Production

The working example presented herein demonstrates the successful reduction of levels of brain Aβ40 and Aβ42 in wild-type guinea pigs, an animal model of Aβ production. Wild-type guinea pigs are an art-accepted model for normal Aβ production and are known to produce Aβ peptides that are immunologically identical to human Aβ. Therefore, wild-type guinea pigs provide an animal model for examining perturbations in APP metabolism with and without drug treatment, and, as such also represent an animal model for a physiological hallmark of Alzheimer's disease.

9.1. Materials and Methods

Osmotic minipumps containing 200 μl compound STI-571 (50 mM in saline buffer, final concentration of 15.4 mg/kg) were implanted intrathecally in 300-350 g guinea pigs. Two hundred microliters of Compound 1 (10 mM, final 2.8 mg/kg) in 100% DMSO was placed in a small catheter attached to the minipump.

Compounds were tested for an ability to modulate Aβ levels. In particular, STI-571, a member of the phenyl aminopyrimidine class of pharmacophores was tested. Specifically, the mesylate salt of STI-571 (also known as GLEEVEC™, Novartis) was tested. STI-571 is an ATP competitor known to target the ATP binding site on BCR-Abl tyrosine kinase, and also to inhibit Abl, c-kit and platelet-derived growth factor receptor (PDGFR). An STI-571 variant, WGB-BC-15 (see FIG. 20), was also tested. In addition, Compounds 1 and 2 (see FIG. 20), members of the pyrimidinyl pyridone tyrosine kinase inhibitor class of molecules, were tested.

After 7 days of treatment, animals were sacrificed, and their brains homogenized in 25 mM Tris 7.5, 50 mM NaCl, 1 mM DTT, 5 mM EDTA, 1 mM EGTA, and 1× protease inhibitor cocktail (Complete™, Boehringer Biochemicals). Aliquots of brain homogenate were assayed for Aβ peptide by using a sandwich ELISA according the manufacturer's recommendations (Biosource International, Camarillo, Calif.) and for C99 by immunoprecipitation and Western blot analysis using standard methods.

9.2. Results

Levels of brain Aβ40 and Aβ42 were reduced (FIGS. 15A and 15B), and C99 increased (FIGS. 15C and 15D), in animals treated with 15.4 mg/kg STI-571. Similar changes were seen with 2.8 mg/kg Compound 1 (FIGS. 16A-D). Animals appeared healthy and active at these doses of compound.

These data demonstrate that in vivo, STI-571 and Compound 1 inhibit production of Aβ peptides. Further, because the amounts of C99 rose significantly, the compounds represent putative γ-secretase inhibitors, as the reduction in Aβ levels is likely due to the specific cleavage of C99.

10. EXAMPLE 5

Administration of STI-571 or Compound 1 Does not Inhibit the Cleavage of Notch A major concern related to the use of γ-secretase inhibitors is their potential for inhibition of cell signaling through the Notch cell surface receptor. Notch receptors function in a variety of cell fate decisions in the developing nervous system and function in adult life in the immune system. Thus, it is generally preferred that the Aβ inhibition not significantly inhibit cleavage of Notch. This working example demonstrates that administration of STI-571 or Compound 1 to cultured cells at levels that strongly inhibit Aβ formation does not affect Notch cleavage. As such, these compounds represent selective inhibitors of γ-secretase activity.

10.1. Materials and Methods

N2a cells were transfected with a constitutively active truncated form of Notch, mouse "deleted-extracellular" Notch (mΔe-Notch), which supplies a direct substrate for γ-secretase (De Strooper et al., 1999, Nature 398: 518-522).

10.2. Results

At levels of STI-571 (FIG. 17) or Compound 1 (FIG. 18) that strongly inhibit Aβ-formation, cleavage of mΔe-Notch to form Notch intracellular domain (NICD) was unaffected.

11. EXAMPLE 6

STI-571 and Compound 1 Inhibit Production of Aβ by Inhibition of ARG Kinase but not ABL Kinase Abl tyrosine kinases are known targets of STI-571 (Okuda et al., 2001, Blood 97(8): 2440-2448). Abl kinase is a known target of Compound 1. To determine whether Abl kinase is required for Aβ production and whether the effects of the inhibitors STI-571 and Compound 1 on Aβ production result from inhibition of Abl kinase, the experiments described herein were conducted. The results presented in this working example demonstrate that STI-571 and Compound 1 inhibit production of Aβ whether or not Abl kinase is present.

11.1. Materials and Methods

Abl knockout (Abl−/−) 3T3 mouse fibroblasts and wild-type 3T3 mouse fibroblasts (see Liu et al., 1996, Nature 384(6606):273-6) were grown separately and to confluence in 100 mm Corning tissue culture plates. These fibroblast cell lines are permanent cell lines. Several plates were exposed to either 5 μM or 10 μM STI-571 dissolved in water, or to no STI-571. Several other plates were exposed to either 0.5 μM or 1.0 μM Compound 1 (dissolved in DMSO) or to DMSO without Compound 1.

For the above-described cell cultures, each of the drugs or control solvents was added to a standard culture medium (DMEM+10% FBS+pen/strep) at a dilution of 1:1000 and cultures were then incubated at 37° C. for 2 hours. The contacting of cell cultures and incubation with inhibitors and solvent, as described above, constituted "pretreatment" of cells.

The first culture medium was then removed and the cell cultures were rinsed with a second culture medium lacking methionine, cysteine and glutamate. The cell cultures were incubated with this culture medium for 30 minutes (to stimulate subsequent uptake of amino acids). Then the second culture medium was exchanged for fresh first culture medium containing $^{35}$S-labeled methionine and cysteine (NEN Express label 50 µl/ml) and unlabeled glutamine (final concentration 2 mM) and with inhibitors as described above, and incubated for 4 hours at 37° C.

Media was collected and immunoprecipitated with 4G8 mouse monoclonal antibody (Senetek, Napa, Calif.) to detect Aβ peptides and resolved by PAGE and autoradiography, according to standard methods (as described hereinabove). Cells were dissolved in 3% SDS, diluted in immunoprecipitation buffer containing 1% Triton X-100 and immunoprecipitated with 369 rabbit polyclonal antiserum (produced according to standard methods) to detect APP and resolved by PAGE and autoradiography.

11.2. Results

Both wild-type 3T3 fibroblasts and Abl −/−3T3 fibroblasts produced similar quantities of Aβ peptide and p3 peptide (both products of γ-secretase activity) compared to the quantities of APP produced by each cell line (quantities of APP were also similar in both cell lines). This demonstrates that Abl kinase is not necessary for Aβ production or for γ-secretase activity.

Furthermore, both STI-571 and Compound 1 inhibited Aβ production in both the 3T3 fibroblast and Abl −/−3T3 fibroblast cells lines to similar degrees, and this inhibition was also similar to the degree of inhibition of Aβ production achieved by the inhibitors in N2a cells. This indicates that the target of the inhibitors, responsible for Aβ inhibition, was intact, whether or not Abl kinase was present.

12. EXAMPLE 7

Mechanism of Action of γ-Secretase Activity

It was previously noted (in FIGS. 17 and 18) that Notch-I cleavage is not inhibited by the inhibitors STI-571 and Compound 1. Significantly, Notch cleavage is known to be catalyzed by γ-secretase activity. Thus γ-secretase inhibitors that inhibit Aβ production but not Notch cleavage (i.e., selective γ-secretase inhibitors) may be used as therapeutic agents because they potentially produce fewer side effects that could injure the immune system, as well as other Notch dependent systems.

This working example demonstrates that Notch-1 cleavage is not energy or ATP-dependent, or differentially affected by the presence (versus the absence) of ATP. Thus, without wishing to be bound by any particular theory, ATP modulators, such as inhibitors that compete with ATP for binding to protein targets, do not inhibit Notch cleavage and will not be cytotoxic or affect cellular or developmental processes regulated by the Notch protein.

12.1. Materials and Methods

A cell-free system derived from mΔe-Notch 1 transfected N2a cells (Leem et al., 2002, Neurobiol Dis. 11(1):64-82) was created according to the methods described in Example 1 (see also, Xu et al., 1997, Proc. Natl. Acad. Sci. USA 94: 3748-3752). The cells were pulse-labeled with radioactivity and chased at 20° C. for 2 hours to accumulate labeled Notch in the trans Golgi network (TGN). The cells were then incubated at 37° C. for 20 to 25 minutes to synchronize localization of mΔe-Notch 1 to the cell surface (considered the primary site for Notch 1 cleavage). The cells were then permeabilized and incubated either with or without a standard ATP energy regenerating system with GTP (Xu et al., 1997, Proc. Natl. Acad. Sci. USA 94: 3748-3752). Samples were incubated, under the same conditions, either with or without a standard γ-secretase inhibitor (Calbiochem).

To measure mΔe Notch-1 and Notch intracellular domain (NICD, the product of Notch cleavage), permeabilized cells were sedimented and both sedimented cells and supernatant were immunoprecipitated with anti-myc antibody according to standard methods to detect Notch and NICD (both were labeled with myc tags).

12.2. Results

NICD was found in the supernatant because the cells are permeabilized and hence NICD, which would otherwise be in the cytosol, could be retrieved by sedimenting the permeabilized cells, thus separating them from the supernatant. Furthermore, the standard γ-secretase inhibitor inhibited Notch cleavage as expected (FIG. 19), showing that γ-secretase activity is necessary for Notch cleavage in this system.

It was previously shown, in Section 10, that at levels of STI-571 (FIG. 17) or Compound 1 (FIG. 18) that strongly inhibit Aβ formation, cleavage of mΔe-Notch to form Notch intracellular domain (NICD) was unaffected. In the present example, it was demonstrated that Notch is cleaved equally effectively in the presence or absence of a standard γ-secretase inhibitor, and in the presence or absence of ATP. Thus Notch cleavage is not ATP-dependent.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All references cited herein are incorporated herein by reference in their entireties and for all purposes to the same extent as if each individual publication, patent or patent application was specifically and individually indicated to be incorporated by reference in its entirety for all purposes.

The citation of any publication is for its disclosure prior to the filing date and should not be construed as an admission that the present invention is not entitled to antedate such publication by virtue of prior invention.

What is claimed is:

1. A method for reducing amyloid-β peptide (Aβ) plaque in a cell or tissue which produces Aβ plaque, comprising contacting said cell or tissue with an amount of a compound sufficient to decrease Aβ levels in said cell or tissue, wherein said compound modulates an ATP-dependent enzymatic activity wherein said compound is WGB-BC-15, as illustrated below

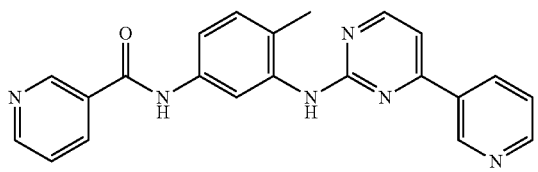

or a pharmaceutically acceptable salt thereof.

2. The method of claim 1 wherein the Aβ plaque is neuritic plaque.

3. The method of claim 1 wherein the Aβ comprises metabolites of β-amyloid precursor protein.

4. The method of claim 1 wherein the Aβ is Aβ42.

5. The method of claim 1 wherein the compound increases levels of sAPPα.

6. The method of claim 1 wherein the compound does not inhibit Notch-1 cleavage.

7. The method of claim 1 wherein the enzymatic activity is a γ-secretase activity.

8. The method of claim 1 wherein the enzymatic activity is a kinase activity.

9. The method of claim 8 wherein the kinase is a tyrosine kinase.

10. The method of claim 9 wherein the tyrosine kinase is Abl kinase, BCR-Abl kinase, ARG kinase, src kinase, c-kit or platelet-derived growth factor receptor.

11. The method of claim 9 wherein the kinase is a serine/threonine kinase, a carbohydrate kinase or a lipid kinase.

12. A method for reducing Aβ plaque levels in a cell or tissue which produces Aβ plaque, comprising contacting said cell or tissue with an amount of an ATP modulator sufficient to decrease Aβ levels in said cell or tissue wherein said compound is WGB-BC-15, as illustrated below

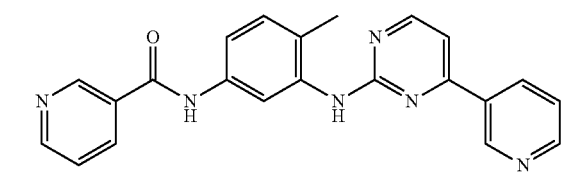

or a pharmaceutically acceptable salt thereof.

* * * * *

SEQUENCE LISTING

<160> NUMBER OF SEQ ID NOS: 2

<210> SEQ ID NO 1
<211> LENGTH: 40
<212> TYPE: PRT
<213> ORGANISM: Homo sapiens

<400> SEQUENCE: 1

Asp Ala Glu Phe Arg His Asp Ser Gly Tyr Glu Val His His Gln Lys
1               5                   10                  15

```
Leu Val Phe Phe Ala Glu Asp Val Gly Ser Asn Lys Gly Ala Ile Ile
            20                  25                  30

Gly Leu Met Val Gly Gly Val Val
            35              40

<210> SEQ ID NO 2
<211> LENGTH: 42
<212> TYPE: PRT
<213> ORGANISM: Homo sapiens

<400> SEQUENCE: 2

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
            35              40
```